US009476060B2

(12) United States Patent
Vainstein et al.

(10) Patent No.: US 9,476,060 B2
(45) Date of Patent: *Oct. 25, 2016

(54) GENERATING GENOTYPIC VARIATIONS IN PLANT GENOMES BY GAMETE INFECTION

(75) Inventors: Alexander Vainstein, Rechovot (IL); Amir Zuker, Nes Ziona (IL)

(73) Assignees: Danziger Innovations Ltd., Moshav Mishmar HaShiva (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 940 days.

This patent is subject to a terminal disclaimer.

(21) Appl. No.: 13/502,532

(22) PCT Filed: Oct. 21, 2010

(86) PCT No.: PCT/IL2010/000874
§ 371 (c)(1),
(2), (4) Date: Apr. 18, 2012

(87) PCT Pub. No.: WO2011/048600
PCT Pub. Date: Apr. 28, 2011

(65) Prior Publication Data
US 2012/0210461 A1 Aug. 16, 2012

Related U.S. Application Data

(60) Provisional application No. 61/272,684, filed on Oct. 21, 2009.

(51) Int. Cl.
*C12N 15/82* (2006.01)

(52) U.S. Cl.
CPC ................... *C12N 15/8279* (2013.01)

(58) Field of Classification Search
None
See application file for complete search history.

(56) References Cited

U.S. PATENT DOCUMENTS

| | | | |
|---|---|---|---|
| 5,316,931 A | 5/1994 | Donson et al. | |
| 5,530,191 A | 6/1996 | Maliga | |
| 5,811,653 A | 9/1998 | Turpen | |
| 6,300,133 B1 | 10/2001 | Lindbo et al. | |
| 6,610,545 B2 | 8/2003 | Dujon et al. | |
| 6,911,575 B1 | 6/2005 | Baszczynski et al. | |
| 7,229,829 B2 | 6/2007 | Dinesh Kumar et al. | |
| 7,309,605 B1 | 12/2007 | Dujon et al. | |
| 8,791,324 B2 * | 7/2014 | Vainstein ........... | C12N 15/8203 435/320.1 |
| 2003/0182684 A1 | 9/2003 | Dinesh Kumar et al. | |
| 2005/0009012 A1 | 1/2005 | Holzberg et al. | |
| 2005/0026157 A1 | 2/2005 | Baltimore et al. | |
| 2006/0292682 A1 | 12/2006 | Hawkins et al. | |
| 2007/0134796 A1 | 6/2007 | Holmes et al. | |
| 2008/0182332 A1 * | 7/2008 | Cai ................... | C12N 15/8243 435/468 |
| 2014/0273235 A1 | 9/2014 | Voytas et al. | |
| 2014/0331360 A1 | 11/2014 | Vainstein et al. | |

FOREIGN PATENT DOCUMENTS

| | | |
|---|---|---|
| IL | 208819 | 7/2013 |
| WO | WO 2009/110695 | 0/2009 |
| WO | WO 2015/189693 | 0/2015 |
| WO | WO 2007/137788 | 12/2007 |
| WO | WO 2007/139982 | 12/2007 |
| WO | WO 2008/148559 | 12/2008 |
| WO | WO 2011/048600 | 4/2011 |

OTHER PUBLICATIONS

Isalan 2012 (Nature Methods 9: p. 32-34).*
Zhang et al 2013 (Plant Methods 9:28 p. 1-13).*
Feng et al. "Efficient Genome Editing in Plants Using A CRISPR/CAS System", Cell Research, 23: 1229-1232, Published Online Aug. 20, 2013.
Jiang et al. "Demonstration of CRISPR/Cas9/SgRNA-Mediated Targeted Gene Modification in Arabidopsis, Tobacco, Sorghum and Rice", Nucleic Acid Research, 41(20): e188-1-e188-12, Published Online Sep. 2, 2013.
Li et al. "Multiplex and Homologous Recombination-Mediated Genome Editing in Arabidopsis and Nicotiana Benthamiana Using Guide RNA and Cas9", Nature Biotechnology, 31(8): 688-691, Aug. 2013.
Mao et al. "Application of the CRISPR-Cas System for Efficient Genome Engineering in Plants", Molecular Plant, 6(6): 2008-2011, Advance Access Publication Aug. 12, 2013.
Miao et al. "Targeted Mutagenesis in Rice Using CRISPR-Cas System", Cell Research, 23: 1233-1236, Published Online Sep. 3, 2013.
Nekrasov et al. "Targeted Mutagenesis in the Model Plant Nicotiana Benthamiana Using Cas9 RNA-Guided Endonuclease", Nature Biotechnology, 31(8): 691-693, Aug. 2013.
Shan et al. "Targeted Genome Modification of Crop Plants Using CRISPR-Cas System", Nature Biotechnology, 31(8): 686-688, Aug. 2013.
Xie et al. "RNA-Guided Genome Editing in Plants Using A CRISPR-Cas System", Molecular Plant, 6(6): 1975-1983, Advance Access Publication Aug. 17, 2013.
Communication Pursuant to Article 94(3) EPC Dated Feb. 4, 2014 From the European Patent Office Re. Application No. 09734624.1.
Office Action Dated Jan. 13, 2014 From the State Intellectual Property Office of the People's Republic of China Re. Application No. 200980123518.1 and Its Translation Into English.

(Continued)

*Primary Examiner* — Brent Page
*Assistant Examiner* — Matthew Keogh

(57) ABSTRACT

A method of generating genotypic variation in a genome of a plant is disclosed. The method comprising introducing into a gamete or a gamete producing tissue of the plant at least one viral expression vector encoding at least one chimeric nuclease which comprises a DNA binding domain, a nuclease and a localization signal to a DNA-containing organelle, wherein the DNA binding domain mediates specific targeting of the nuclease to the genome of the plant, wherein the introducing is performed such that the gamete or gamete producing tissue expresses the chimeric nuclease but not all plant tissues express the chimeric nuclease, thereby generating genotypic variation in the genome of the plant.

14 Claims, 45 Drawing Sheets
(34 of 45 Drawing Sheet(s) Filed in Color)

(56) References Cited

OTHER PUBLICATIONS

Notice of Allowance Dated Mar. 10, 2014 From the US Patent and Trademark Office Re. U.S. Appl. No. 12/988,636.
Official Action Dated Nov. 30, 2012 From the US Patent and Trademark Office Re. U.S. Appl. No. 12/988,636.
Goulden et al. "Pea Early Browning Virus (Isolate TPA56) RNA2 Complete Sequence, Encoding Coat Protein, 9kDa Protein and 23kDa Protein", GenBank FASTA, GenBank: X78455.1, GenBank Accession No. X78455, Aug. 30, 1995.
Goulden et al. "The Complete Nucleotide Sequence of PEBV RNA2 Reveals the Presence of a Novel Open reading Frame and Provides Insights Into the Structure of Tobraviral Subgenomic Promoters", Nucleic Acids Research, EMBL Accession No. X51828, 18(15); 4507-4512, 1990.
Advisory Action Before the Filing of an Appeal Brief Dated Apr. 8, 2013 From the US Patent and Trademark Office Re. U.S. Appl. No. 12/988,636.
Translation of Office Action Dated Mar. 26, 2013 From the State Intellectual Property Office of the People's Republic of China Re. Application No. 200980123518.1.
Translation of Search Report Dated Mar. 25, 2013 From the State Intellectual Property Office of the People's Republic of China Re. Application No. 200980123518.1.
Hernandez et al. "Tobacco Rattle Virus Genes for Coat Protein, 28.7 kDa & 32.8 kDa Proteins, Genomic RNA", GenBank NCBI [Online], GenBank: 236974.2, GenBank Accession No. 236974, Oct. 21, 2003.
Communication Pursuant to Rules 70(2) and 70a(2) EPC Dated Nov. 7, 2011 From the European Patent Office Re. Application No. 09734624.1.
Examination Report Dated Feb. 22, 2012 From the Intellectual Property Office of New Zealand Re. Application No. 588767.
Examination Report Dated Mar. 28, 2011 From the Intellectual Property Office of New Zealand Re. Application No. 588767.
International Preliminary Report on Patentability Dated Nov. 4, 2010 From the International Bureau of WIPO Re. Application No. PCT/IL2009/000432.
International Search Report and the Written Opinion Dated Jun. 2, 2010 From the International Searching Authority Re. Application No. PCT/IL09/00432.
International Search Report and the Written Opinion Dated Mar. 25, 2011 From the International Searching Authority Re. Application No. PCT/IL2010/000874.
Official Action Dated Mar. 27, 2012 From the US Patent and Trademark Office Re. U.S. Appl. No. 12/988,636.
Requisition-Sequence Listing Dated Mar. 6, 2012 From the Canadian Intellectual Property Office Re. Application No. 2,721,372.
Response Dated Dec. 20, 2011 to Examination Report of Mar. 28, 2011 From the Intellectual Property Office of New Zealand Re. Application No. 588767.
Restriction Official Action Dated Dec. 21, 2011 From the US Patent and Trademark Office Re. U.S. Appl. No. 12/988,636.
Supplementary European Search Report and the European Search Opinion Dated Oct. 19, 2011 From the European Patent Office Re. Application No. 09734624.1.
Beumer et al. "Efficient Gene Targeting in *Drosophila* With Zinc-Finger Nucleases", Genetics, 172(4): 2391-2403, 2006.
Chapman et al. "Potato Virus X as a Vector for Gene Expression in Plants", The Plant Journal, 2(4): 549-557, 1992.
Dolja et al. "Isolation and Stability of Histidine-Tagged Proteins Produced in Plants Via Potyvirus Gene Vectors", Virology, 252(1): 269-274, 1998.
Dolja et al. "Tagging of Plant Potyvirus Replication and Movement by Insertion of ?-Glucuronidase Into the Viral Polyprotein", Proc. Natl. Acad. Sci. USA, 89: 10208-10212, 1992.
Donson et al. "Systemic Expression of a Bacterial Gene by a Tobacco Mosaic Virus-Based Vector", Proc. Natl. Acad. Sci. USA, 88(16): 7204-7208, 1991.

Gallie et al. "The 5'-Leader Sequence of Tobacco Mosaic Virus RNA Enhances the Expression of Foreign Gene Transcripts in Vitro and in Vivo", Nucleic Acids Research, 15(8): 3257-3273, 1987.
Gleba et al. "Engineering Viral Expression Vectors for Plants: the 'Full Virus' and the 'Deconstructed Virus' Strategies", Current Opinion in Plant Biology, 7: 182188, 2004.
Greenboim-Wainberg et al. "Cross Talk Between Gibberellin and Cytokinin: The Arabidopsis GA Response Inhibitor Spindly Plays a Positive Role in Cytokinin Signaling", Plant Cell, XP002623000, 17(1): 92-102, Jan. 2005.
Lloyd et al. "Targeted Mutagenesis Using Zinc-Finger Nucleases in Arabidopsis", Proc. Natl. Acad. Sci. USA, PNAS, XP055008257, 102(6): 2232-2237, Feb. 8, 2005.
MacFarlane et al. "Efficient Expression of Foreign Proteins in Roots From Tobravirus Vectors", Virology, XP004436150, 267(1): 29-35, Feb. 1, 2000.
Marton et al. "Nontransgenic Genome Modification in Plant Cells", Plant Physiology, 154: 1079-1087, Nov. 2010.
Moehle et al. "Targeted Gene Addition Into a Special Occasion in the Human Genome Using Designed Zinc Finger Nucleases", Proc. Natl. Acad. Sci. USA 104: 3055-3060, 2007.
Papworth et al. "Designer Zinc-Finger Proteins and Their Applications", Gene, XP005282076, 366(1): 27-38, Jan. 17, 2006. Para [06.3], Fig.4.
Pogue "Making an Ally From an Enemy: Plant Virology and the New Agriculture", Annual Reviews in Phytopathology, 40: 45-74, 2002.
Puchta et al. "Two Different But Related Mechanisms Are Used in Plants for the Repair of Genomic Double-Strand Breaks by Homologous Recombination", Proc. Natl. Acad. Sci. USA 93(10): 5055-5060, 1996.
Salomon et al. "Capture of Genomic and T-DNA Sequences During Double-Strand Break Repair in Somatic Plant Cells", The EMBO Journal, 17(20): 6086-6095, 1998.
Tzfira et al. "Agrobacterium T-DNA Integration: Molecules and Models", Trends in Genetics, 20(8): 375-383, 2004.
Tzfira et al. "Site-Specific Integration of Agrobacterium Tumefaciens T-DNA Via Double-Stranded Intermediate", Plant Physiology, 133(3): 1011-1023, 2003.
International Preliminary Report on Patentability Dated May 3, 2012 From the International Bureau of WIPO Re. Application No. PCT/IL2010/000874.
Official Action Dated May 1, 2015 From the US Patent and Trademark Office Re. U.S. Appl. No. 14/341,999.
Office Action Dated Jun. 4, 2012 From the Israel Patent Office Re. Application No. 208819 and Its Translation Into English.
Translation of Office Action Dated Jul. 23, 2013 From the State Intellectual Property Office of the People's Republic of China Re. Application No. 200980123518.1.
Office Action Dated Oct. 22, 2014 From the Israel Patent Office Re. Application No. 225584 and Its Translation Into English.
Official Action Dated Nov. 4, 2014 From the US Patent and Trademark Office Re. U.S. Appl. No. 14/341,999.
Vassilakos et al. "Tobravirus 2b Protein Acts in Trans to Facilitate Transmission by Nematodes", Virology, 279: 478-487, 2001.
Vellios et al "Irnrnunogold Localization of Tobravirus 2b Nematode Transmission Helper Protein Associated With Virus Particles", Virology, 300: 118-124, 2002.
Gao et al. "Self-Processing of Ribozyme-Flanked RNAs Into Guide RNAs in Vitro and in Vivo for CRISPR-Mediated Genome Editing", Journal of Integrative Plant Biology, 56(4): 343-349, Apr. 2014.
Communication Pursuant to Article 94(3) EPC Dated Mar. 12, 2013 From the European Patent Office Re. Application No. 09734624.1.
Gleba et al. "Viral Vectors for the Expression of Proteins in Plants", Current Opinion in Biotechnology, 18: 134-141, 2007.
Examination Report Dated Oct. 14, 2015 From the Government of India, Patent Office, Intellectual Property Building Re. Application No. 2235/MUMNP/2010.
Liu et al. "Tobacco Rattle Virus RNA2-Based VIGS Vector pTRV2, Complete Sequence", Database NCBI [Online], GenBank Accession No. AF406991.1, Database Accession No. AF406991, Nov. 13, 2003.

(56) References Cited

OTHER PUBLICATIONS

Liu et al. "Tobacco Rattle Virus Segment RNA1, Complete Sequence", Database NCBI [Online], GenBank Accession No. AF406990.1, Database Accession No. AF406990, Jun. 11, 2002.
International Search Report and the Written Opinion Dated Feb. 16, 2016 From the International Searching Authority Re. Application No. PCT/IL2015/051150.
Gao et al. "Specific and Heritable Gene Editing in Arabidopsis", Proc. Natl. Acad. Sci. USA, PNAS, 111(12): 4357-4358, Mar. 25, 2014. P.4357, Last Para, P.4358, Middle Col., First Pam.
Senthil-Kumar et al. "Tobacco Rattle Virus-Based Virus-Induced Gene Silencing in Nicotiana Benthamiana", Nature Protocols, 9(7): 1549-1562, Published Online Jun. 5, 2014. Abstract, P.1550, Last Para-P.1551, First Para, Suppl. Fig. 1.
Official Action Dated Apr. 28, 2016 From the US Patent and Trademark Office Re. U.S. Appl. No. 14/341,999.
Office Action Dated Mar. 29, 2016 From the Israel Patent Office Re. Application No. 225584 and Its Translation Into English.
European Search Report and the European Search Opinion Dated Aug. 7, 2015 From the European Patent Office Re. Application No. 15165891.1.
Office Action Dated Aug. 13, 2015 From the Israel Patent Office Re. Application No. 225584.
Translation Dated Aug. 30, 2015 of Office Action Dated Aug. 13, 2015 From the Israel Patent Office Re. Application No. 225584.
Canto et al. "A Cucumber Mosaic Virus (CMV) RNA 1 Transgene Mediates Suppression of the Homologous Viral RNA 1 Constitutively and prevents CMV Entry Into the Phloem", Journal of Virology, XP002558409, 75(19): 9114-9120, Oct. 2001. Fig.2, P.9115, 1-h Col., Para 5.
Carette et al. "Cowpea Mosaic Virus 32- and 60-Kilodalton Replication Proteins Target and Change the Morphology of Endoplasmic Reticulum Membranes", Journal of Virology, XP055205027, 76(12): 6293-6301, Jun. 15, 2002. Fig.1.
Liu et al. "Functional Replacement of the Tobacco Rattle Virus Cysteine-Rich Protein by Pathogenicity Proteins From Unrelated Plant Viruses", Virology, XP002222989, 298: 232-239, Jul. 5, 2002. Fig.1.
Ratcliff et al. "Gene Silencing Without Dna: RNA-Mediated Cross-Protection Between Viruses", The Plant Cell, XP000827858, 11: 1207-1215, Jul. 1999. Fig.1, P.1208, r-h Col.
Official Action Dated Sep. 21, 2015 From the US Patent and Trademark Office Re. U.S. Appl. No. 14/341,999.
Gleba et al. "Engineering Viral Expression Vectors for Plants: The 'Full Virus' and the 'Deconstructed Virus' Strategies", Current Opinion in Plant Biology 7:182-188, 2004.

\* cited by examiner

FIG. 1A

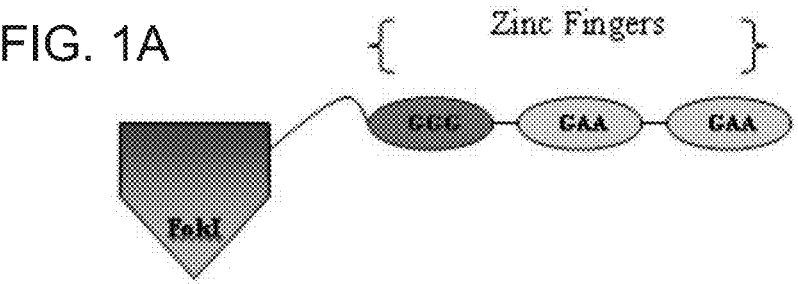

FIG. 1B

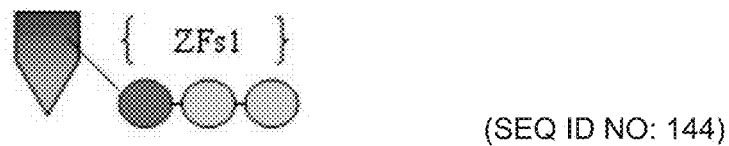

(SEQ ID NO: 144)

NNNNNNGGTGGAAAGNNNNGGGGAAGAA NNNNNNNN
NNNNNNCCACCTTTCNNNNCCCCTTCTTNNNNNNNN

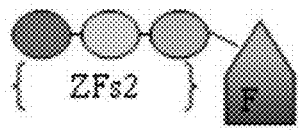

FIG. 1C (SEQ ID NO: 144)

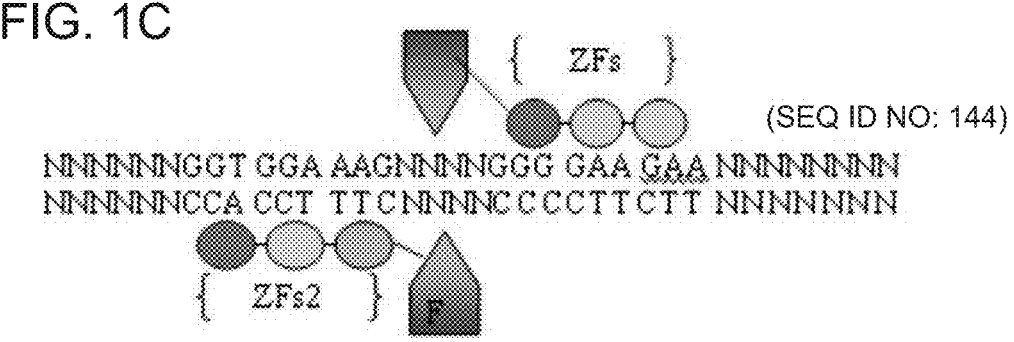

NNNNNNGGT GGA AGNNNNGGG GAA GAA NNNNNNNN
NNNNNNCCA CCT TTCNNNNCCC CTT CTT NNNNNNN

FIG. 1D (SEQ ID NO: 144)

NNNNNNGGTGGAAAGNN / NNGGGGAAGAA NNNNNNNN
NNNNNNCCACCTTTCNN / NNCCCCTTCTTNNNNNNNN 

FIG. 1E

NNNNNNGGTGGAAAGNNXXXNNGGGGAAGAA NNNNNNNN
NNNNNNCCACCTTTCNNXXXNNCCCCTTCTTNNNNNNNN (SEQ ID NO: 145)

```
                                                        1         10        20        30        40        50  54
(SEQ ID NO: 51)                                         |---------+---------+---------+---------+---------+----|
TaV-T2A                                                 GAGGGCAGGGGAAGTCTTCTAACATGCGGGGACGTGGAGGAAAATCCCGGCCCC
pTRV-T2A                                                GAAGGAAGAGGATCTCTTCTTACTTGTGGTGATGTTGAAGAGAATCCTGGACCA
(SEQ ID NO: 52)

GAATTCGGACACATGTGCCAAATGGATAGAGTGGAATCCTCCTACTTTGGGGCGG
AATCCTCCTACCCTCAATATGATGCGAGGAGCGGAATCCTCCTACTCCTA
GGGCGGAATCCTCATACCCTCAATATGTCAAGGAGCGGAATCCTCCTA
CTCCTAGGGTGGAATCCTCCTCAATATGATGCAAGGAGTGGAATC
CTCCTCCCTCATTATGATGCAAGGAGCAGAATCCTCTGCTCCTAGGAC
GGAATCCTCTTACCCTCAATATGATGTAAGGAGCGGAATATAAAGTTGAGGCGAAATAC
GAGGGGGAAATCCTCCTGCTGCTGCAATATCATAATATAAAGTTGAGGCGAAATAC
TCCTATAATCATAATATGCGGTATGATACAATAACAACCCTCACCGGTGCGGGACCCT
TATCGGTTGCCAAAGTATATGTCAAGCTCAGAACCAGAGTACAATGCT
CAGATGCTCAATATAATACCAACAACAGGACATAACATATATAATACAAT
ATAAATCCAAAGCTAAGGCGTAATGAGTACGCCTATCGGTAGCTACACAC
GTAAGGAACACGTGGTAGAATATCCACAAGGCCAAGGCCTCAACAACGCTTTG
TGGATATAATCACTTACCTTATTCCAAACGATCCCACTGCTACTCAACAACGCTTTG
TCCTTTGGGTTCACTGCCAAACGATCCCCATTCATCCTAGAACAATTC
ATATCAAATAAGGCTAAAGGCTTCATTCTTACATCCTAGAACAATTC
GGGTAGGAACCCAACACCCATTTGAATAGACAATACGCGGTCCAGGCCT
ATGTATATGGTTCAAAATCACATAATCAAACCCTAAATAATTACATTTA
CGGGTCCAATTAACGAATATATCAATTCCATTATCGGGTCCAATT
AACCCTTGAAACTATCAAATATATTAACTTATTAAAACGATTTTAATATCCC
AATTTCTACCGTGATGTTCGGGTTGAAAAATCTATTTTTCCTGCTCCTTTCTAT
CCTTACCTGATGTTCGGTTTTTCTCGTTGCGTCCTCAATTGTTCGTTTCGTTTCTGTT
TCTCTCTTTCTTGCCTTTCTTTTTCTCGTTGCGTCCTCAATTGTTCGTTTCGTTTCTGTT
TCCATTTGCAAATGTAAGCTT

*(SEQ ID NO: 8)*

FIG. 3

GAATTCTATAGAATGGCTGACTATGCACTAGAACTAGTCCATGAACCTTCCG
AGAATGTTCAAAGATTTATTGATGACCTTTCTTTTTCTAGAGATCCCAG
ATGGCTCGAGAGATTGACGTCGGGATTTCATTTGATGTGTTGTTTATAT
TGCCCGAAGGTACGAGGCATATCATAAGTTAGAGCGGGAAGAGTTAGAGC
AGGAGAGCAAGAGATCCCGTGGCCCTAGTGGCAACCGTGGTACCTCATT
TGGAGGTAAGAGTTCTGGTTATTTGGGAGGTCACCTTCCAGGTTATCTC
AGCTTGTGTCATGTGATTCTTAGAGTGCGCGGGTAGTTCATCAAGATTAG
ACTCAGCTTTCTCTTTGTAGCTTTCAACAATCTGTCCAGCTCCCATATTC
AGCGAAAAGGTGTTATCATTTCTCTTTGTAGCTTTCAACAATCTGTCCTGC
TCAGTTGTAAGGGATTTCATTTGAGAGTGTGGTGGCAGTGGTTCTCCAGAAAGTGAT
CATCCAATAGAGGTTGAGAGTGTGGTGGCAGCTGCAGAGGCAGTTTATGAACTGCC
TGCCAGGGTAGTGGCTCAGCTGCAGAGGCAGTTTATGAACTGCC
AGTCTGGCAGGATGTTGAGGTATCTGATGTAGTACATCCATGTATTCTT
CTTCCATTATATGTGAGTAAATTTCATTCTCTCTTTGGATATTGTTCTATTAAG
ATTTATTATTACCATGTTTCCATGGTCTCTCTTTGGATATTGTTCTATTAAG
AATTGATTGCGGTAGAGGGGTAGCTTCTAGTTGATGATTATTCAAGGAAT
T TGTGAGACCCTATTAATTATCTGCCTGCTCTAAATATGAGAGATTTGACAA
TGAGTGTCGTTATTGTCTGCCTGGCATCTTGTTGTGCCACCTTCTATTAT
TATATCAAATTAGTTACCTCTCTCACCATAAGGAGTGTCATGTTTGGATT
ATGGGATTCTAGTTCATCACCATAAGGAGTGTCATGTATCTCTCTTCCAGTG
TAAAGTGATTAGTAAGTAATAGTCGATCTACGTAGCTATGAGCTTGTTCAA
AACGCTAGTAAAGTCATGTGATCGTATGAGCTTGTCTGGATTATAAAAGG
GTTTCTGGTAAATTGTTAGAGTTTCCTTATTATTGGGAGATTAAATTGG
CATGGAAGTTGTTCCATAAGCTT (SEQ ID NO: 9)

FIG. 5A

NLS-P1-25-ZFN1
ATGGTGccaaaaagaagaagaaggtagaagagaccctcTCGAGCTGAAAAACCTTACAAGTGTCCTGAATGTGGAAAGTCTTTTCT
CAGCGTGCTCATCTTGAACGTCACCAGCGAACACACAGGTGAGAAGCCATATAAATGCCCAGAATGTGGTAAATCAT
TCAGTCAGCGTGCTCATCTTGAACGTCATCATGCGTCGTCATCAACGTACTCATCTGGAGGACTAGTCAAAAGTGAACTGGAGGA
AGAGTTTTCACAGTCTGGAGATTTGCGTCGTCATCAACGTACTCATCTGGAGGACTAGTCAAAAGTGAACTGGAGGA
GAAGAAATCTGAACTTCGTCGTCATAAATGTGCCTCATGAATATATTGAATTAATTGAAATTGCCAGAAATTCCAC
TCAGGATAGAATTCTTGAAATGAAGGTAATTTTATGAAAGTTTATGGATATAGAGGTAAACATTTGGGTGGAT
CAAGGAAACCGGACGGAGCAATTTATACTGTCGGATCTCCTATTGATTACGGTGTGATCGTGATACTAAAGCTTATAG
CGGAGGTTATAATCTGCCAAGTCGGAAAGTCTATCCATCTTCTGTAACGCAAGATATGTCGAAGAAATCAAACACGAAACAAACAT
ATCAACCCTAATGAATGTCAGCTTACACGATTAAATCATATCACTAATTGTAATGGAGCTGTTCTTAGTGTAGAAGAGCTTT
GGAAACTACAAAGCTCAGCTTACACGATTAAATCATATCACTAATTGTAATGGAGCTGTTCTTAGTGTAGAAGAGCTTT
AATTGGGAGAAATGATTAAAGCCGGCACATTAACCTTAGAGGAAGTGAGACGGAAATTTAATAACGGCGAGATAAAC
TTTGGATCCTAA
(SEQ ID NO: 31)

FIG. 5B

NLS-P1-25-ZFN2
ATGGTGccaaaaagaagaagaaggtagaagagaccctcTCGAGCTGAAAAACCTTACAAGTGTCCTGAATGTGGAAAGTCTTTTCTC
AGTCTAGCAACCTGCAGAAGTTGGTTCGTCACCAACGGACCCACAACGTACTCATCTGGAGGACTAGTCAAAAGTGAACTGCGGAA
CAGTCGTTCTCACGTTCTGATAAGTTGGTTCGTCATAATTGGTTCGTCATAATTGAAATTGCCAGAAATTCCACTCA
GAGTTTTCACGTTCTGATAATTGGTTCGTCTATAAATTGAAATATGGAATTTTATGGATAATAGAGGTAAACATTTGGGTGATCAA
AGAAATCTGAACTTCGTCGAAATTCTTGAAATGAAGGTAATGAATTTATGGATAATAGAGGTAAACATTTGGGTGATCAA
GGATAGAATTCTTGAAATGAAGGTAATGAATTTATGGATCGTGATCGTGATACTAAAGCTTATAGCGG
GAAACCGGACGGAGCAATTGCCAAGTCTATCCATCTTAATCATCATCAATGCAACGAAATCAAACAACATCA
AGGTATATAATCTGCCAAGTCTATCCATCTTAATCATCATCAATTGTAATGGAGCTGTTCTTAGTGTAGAAGAGCTTTAAGGAA
ACCCTAATGAATGTCAGCTTACACGATTAAATCATCACTAATTGTAATGGAGCTGTTCTTAGTGTAGAAGAGCTTTAATTG
ACTACAAAGCTCAGCTTACACGATTAAATCATCACTAATTGTAATGGAGCTGTTCTTAGTGTAGAAGAGCTTTAATTG
GTGGGAGAAATGATTAAAGCCGGCACATTAACCTTAGAGGAAGTGAGACGGAAATTTAATAACGGCGAGATAAACTTTGG
ATCCTAA
(SEQ ID NO: 32)

FIG. 5C

NLS-P1-36-ZFN1
ATGGTGccaaaaagaagagagaaggtagaagaccoctcTCGAGCTGAAAAACCTTACAAGTGTCCTGAATGTGGAAAGTCTTTTCTA
CTTCTGGACATCTTGTTCGTCACCAGCGAACACACAGGTGAGAAGCCATATAAATGCCCAGAATGTGGTAAATCATTC
AGTACTTCTGGACATCTTGTCGTCACCAACGACCCACACGTACTCATCACGTACTCATATGGAGGACTAGTCAAAGTGAACTGGAGGAGAAG
GTTTTCAACTTCTGGAAATTTGGTTCGTCATCAACTACTCATCACGTACTCATATGGAGGACTAGTCAAAGTGAACTGGAGGAGAAG
AAATCTGAACTTCGTCATAAATGAAATTGAAATATGTGCCTCATGAATATATTGAATTGAAATTGCCAGAAATTCCACTCAGG
ATAGAATTCTTGAAATGAAGGAGCAATTATCTGTCGGATCTCCTATTGATTACGGTGTGATGGATACTAAAGCTTATAGCGGAGGT
AACCGGACGAGCAATTATACTGTCGGATCTCCTATTGATTACGGTGTGATGAATACTAAAGCTTATAGCGGAGGT
TATAATCTGCCAATTGGCCAAGCAGCAGATGAATGCAACGATATGTCGAAGAAATCAAACACGAACAACATATCAACCT
AATGAATGGTGGAAAGTCTATCCATCTTCTGTAACGGAATTGTAATGGAGCTGTTCTTAGTGTAGAAGAGCTTTAATTGGTGGAG
AAGCTCAGCTTACACGATTAAATCATATCACTAATTAACCTTAGAGGAAGTGAGACGGAAATTTAATAACGGCGAGATAAACTTTGGATCCTAA
(SEQ ID NO: 33)

FIG. 5D

NLS-P1-36-ZFN2
ATGGTGccaaaaagaagagagaaggtagaagaccoctcTCGAGCTGAAAAACCTTACAAGTGTCCTGAATGTGGAAAGTCTTTTCTC
GTTCTGATAATTTGGTTCGTCACCAGCGAACACACAGGAGACCCACCGTACTACTCATCATGGAGGACTAGTCAAAGTGAACTGGAGGAGAA
AGTCAGGCTGGACATCTCTGGACATCTCTGTTCGTCATCAACGTACTACTCATCATGGAGGACTAGTCAAAGTGAACTGGAGGAGAA
AGTTTCAACTTCGTCATAAATGAAATTGAAATCGAACATGTGCCTCATCATAATTAATGAAATTGCCAGAAATTCCACTCAG
GAAATCTGAACTTCGTCATAAATGAAATTGAAATCGTCCATCATAATTATGAAATTGCCAGAAATTCCACTCAG
GATAGAATTCTTGAAATGAAGGAGCAATTATCTGTCGGATCTCCTATTGATTGATCGTGATCGTGAAGAGCTTATAGCGGAGG
AAACCGGACGGAGCAATTTATACTGTCGGATCTCCTATTGATTGATCGTGATCGTGAAGAGCTTATAAGGGGAGG
TTATAATCTGCCAATTGGCCAAGCAGATCTATCCATTCCATCCAACGATATGTCGAAGAAATCAAACACGAACAAACATATCAACC
CTAATGAATGGTGGAAAGTCTATCCATCCAATCAAGATAATTGTAATGGAGCTGTTCTTAGTGTAGAGAGCTTTAATTGGTG
ACAAAGCTCAGCTTACACGATTAAATCATCTATCATTAAGCTTAACCCTTAGAGGAAGTGAGACGGAAATTTAATAACGGCGAGATAAACTTTGGATCC
GAGAATGATTAAAGCCGCACATTAACCTTAACCCTTAGAGGAAGTGAGACGGAAATTTAATAACGGCGAGATAAACTTTGGATCC
TAA
(SEQ ID NO: 34)

FIG. 5E pET28c-SX TCGGATCCGAATTCGAGCTCCGTCGA............GCACCACCACCACCACCA
(SEQ ID NO. 49)

pET28c
TCGGATCCGAATTCGAGCTCCGTCGACAAGCTTGCGGCCGCACTCGAGCACCACCACCACCACCA
(SEQ ID NO. 39)

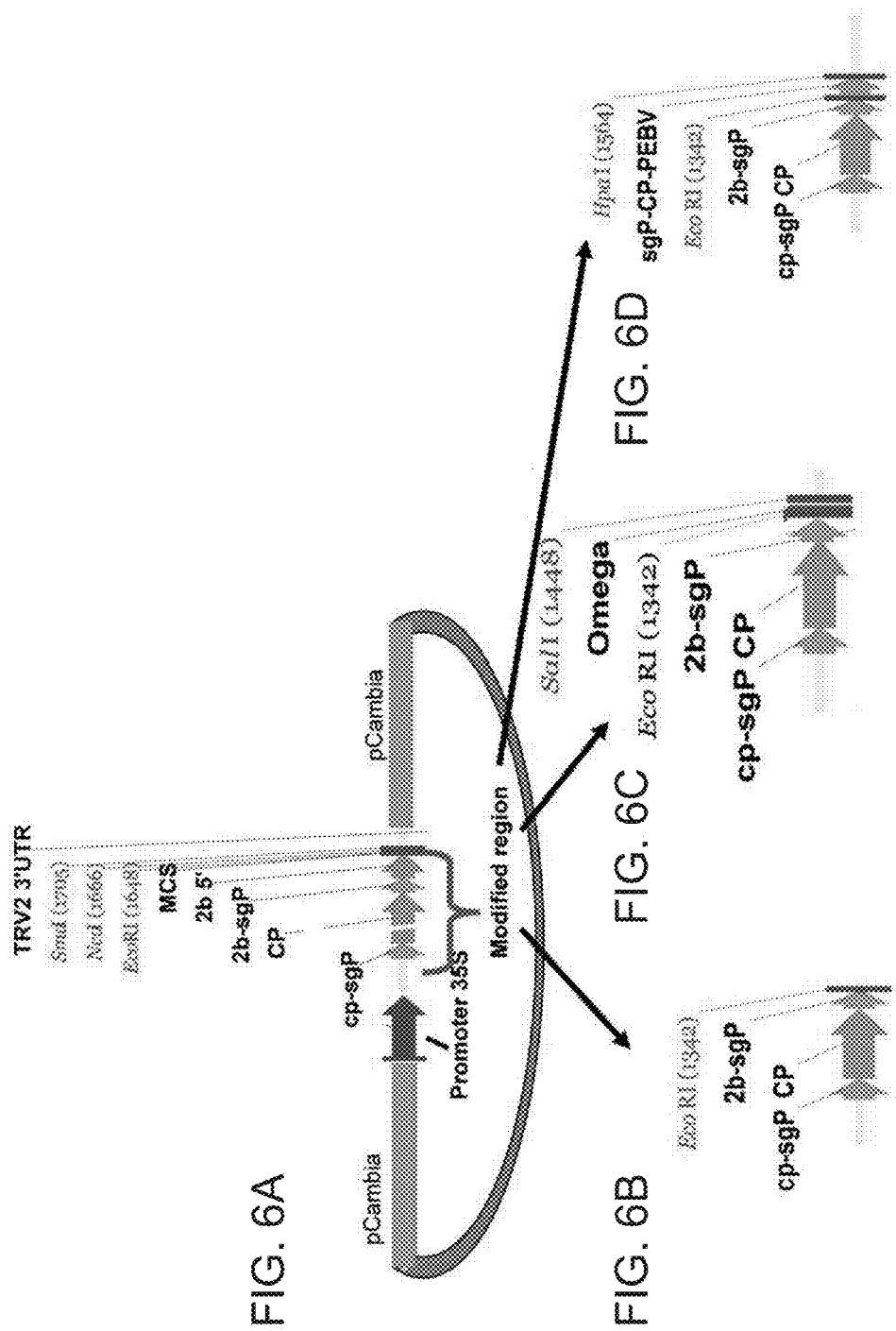

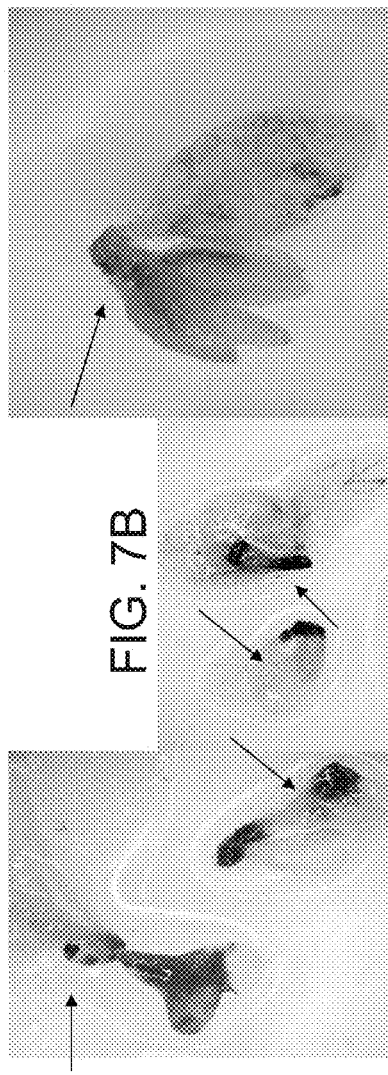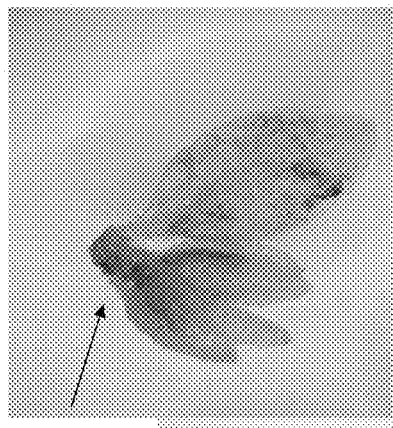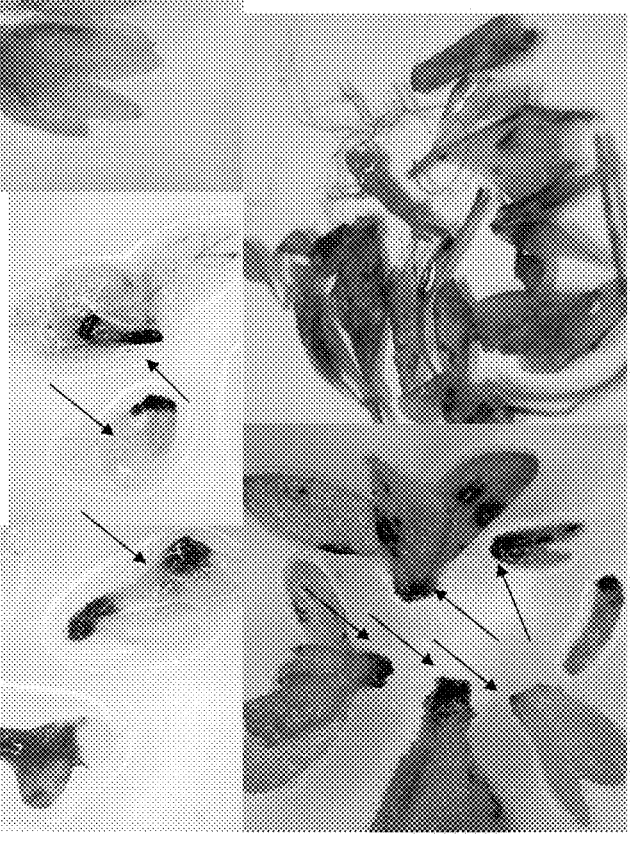

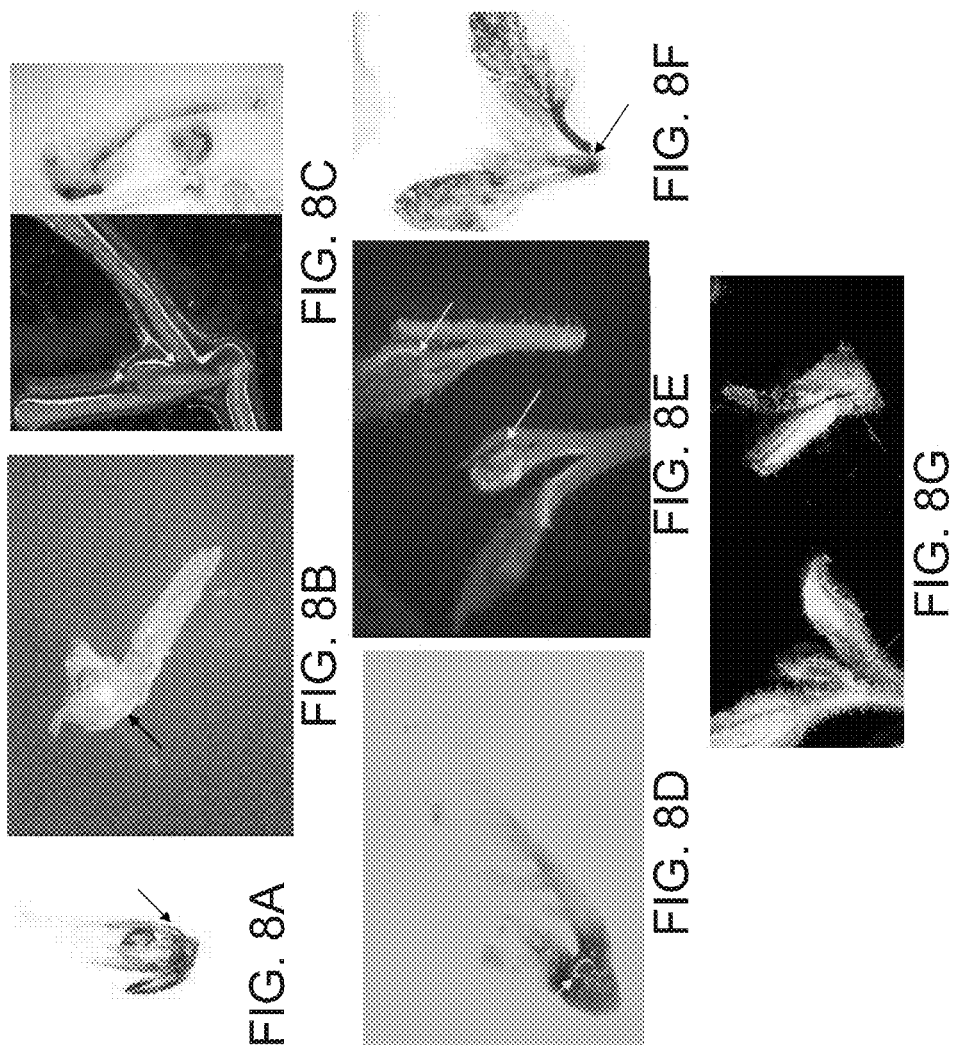

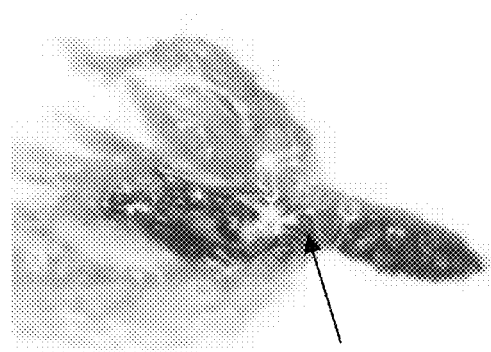
FIG. 10C
FIG. 10B
FIG. 10A

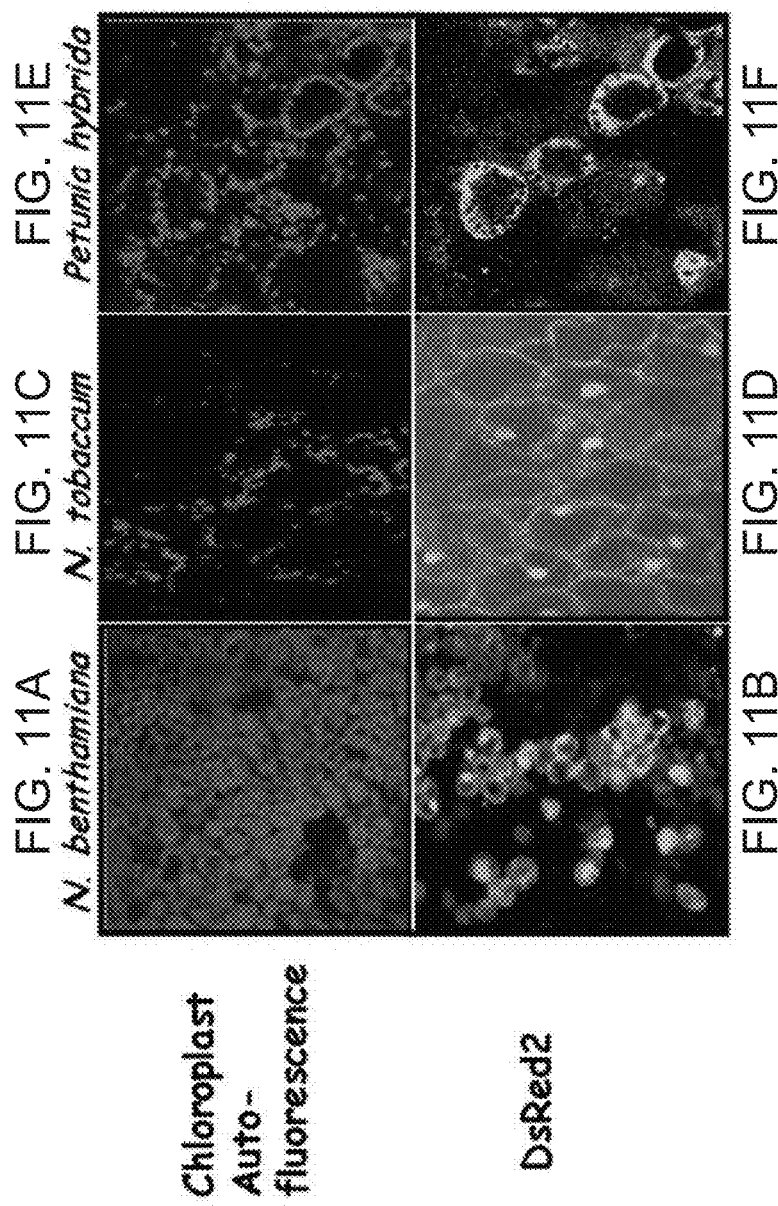

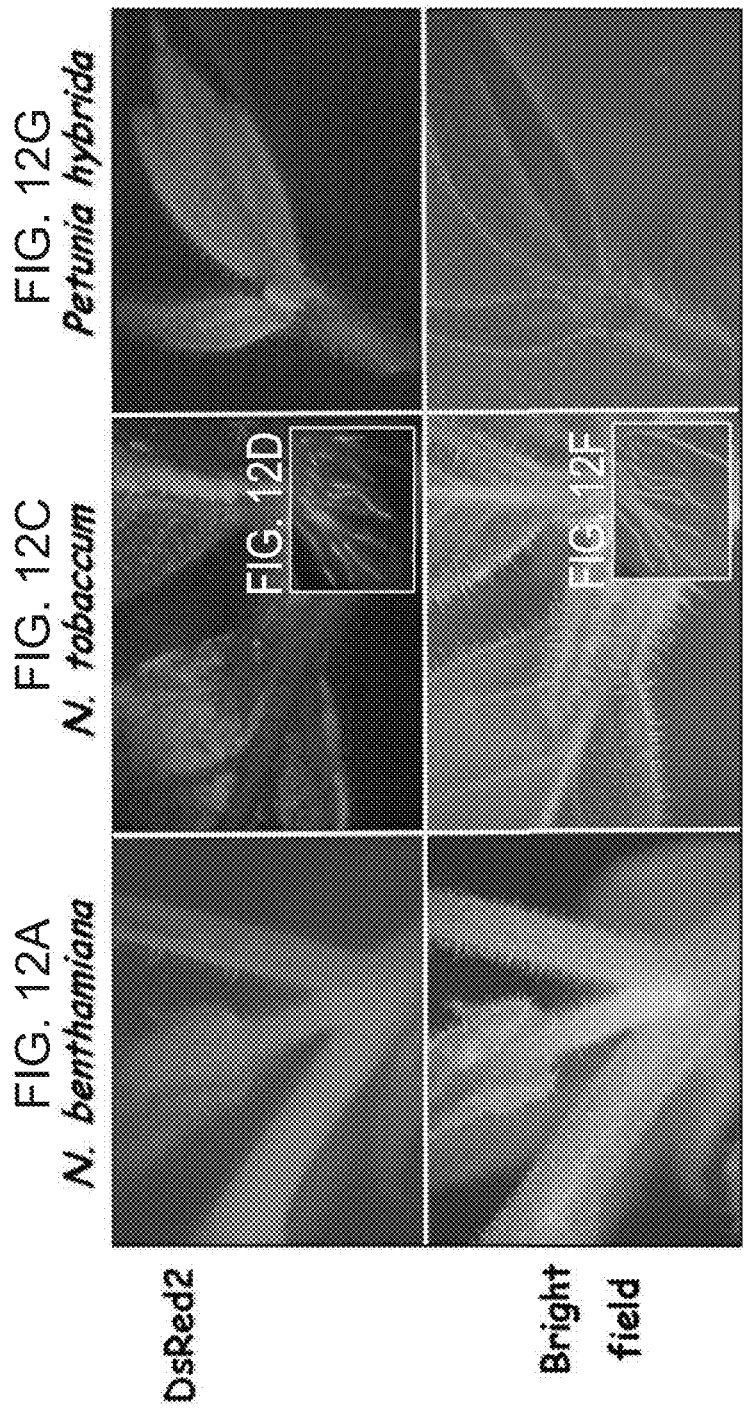

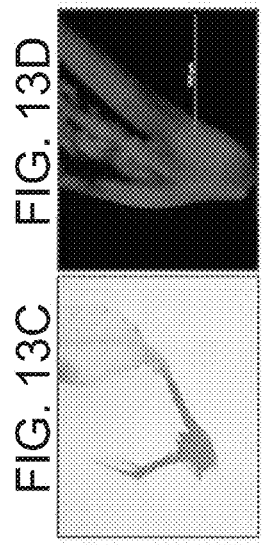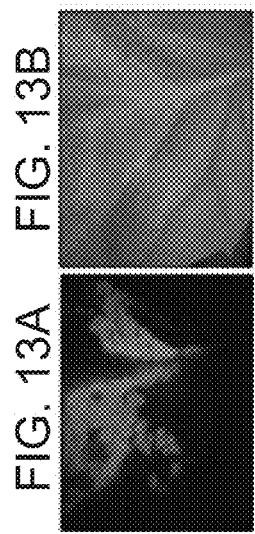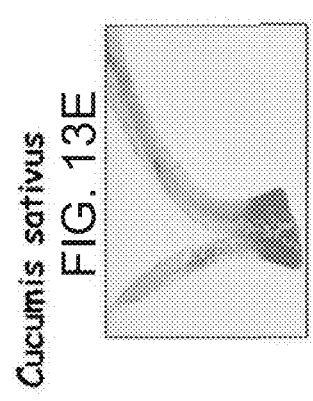
FIG. 13A FIG. 13B *Cucumis sativus*
FIG. 13C FIG. 13D *Spinacia oleracea*
FIG. 13E *Beta vulgaris*
FIG. 13F FIG. 13G *Solanum melongena*
FIG. 13H FIG. 13I *Gossypium hirsutum*
FIG. 13J FIG. 13K *Brassica napus*

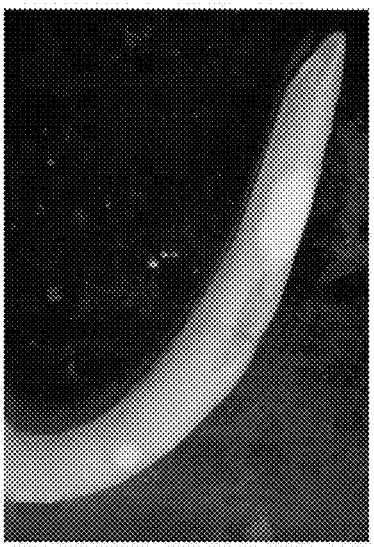

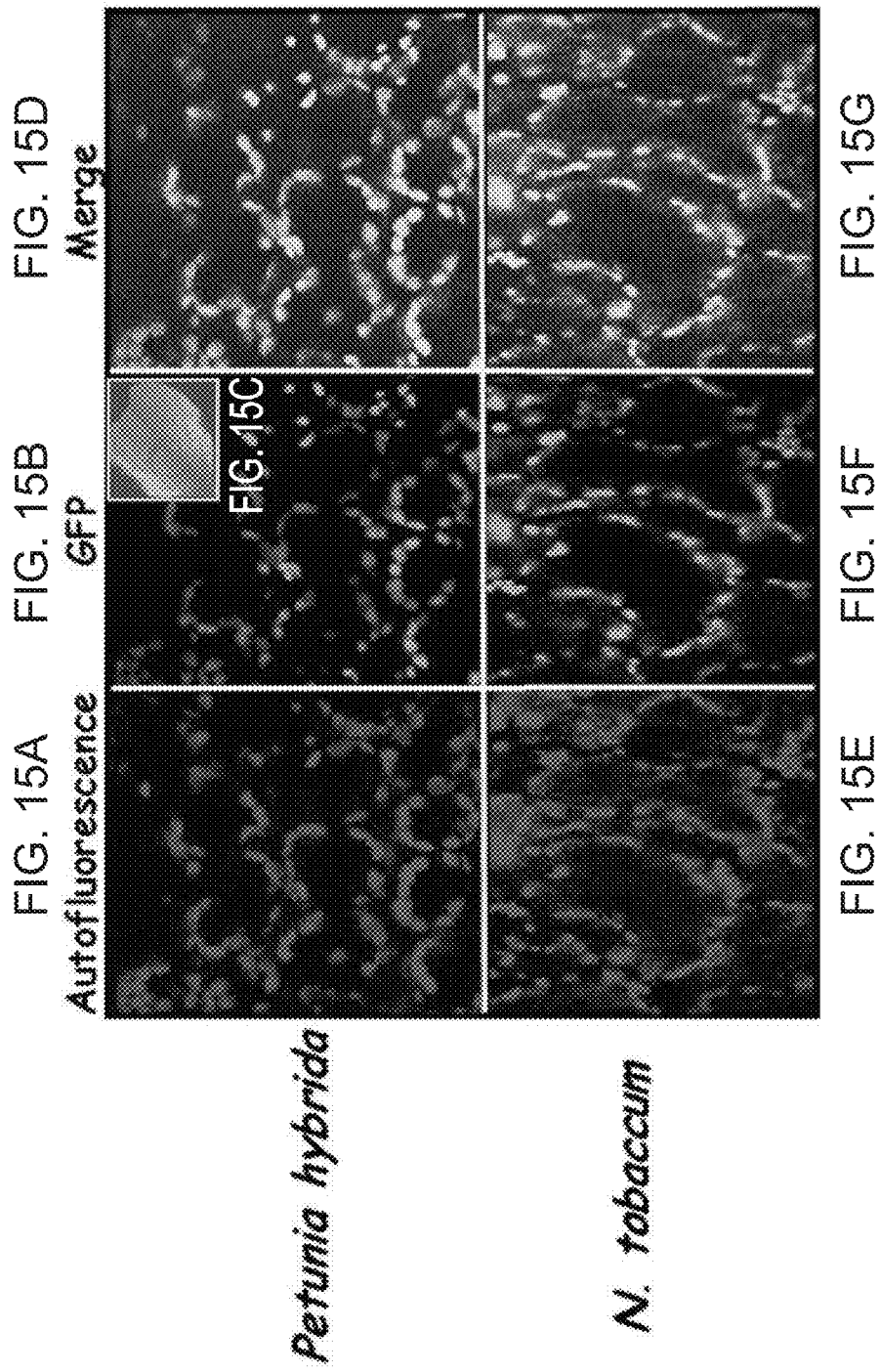

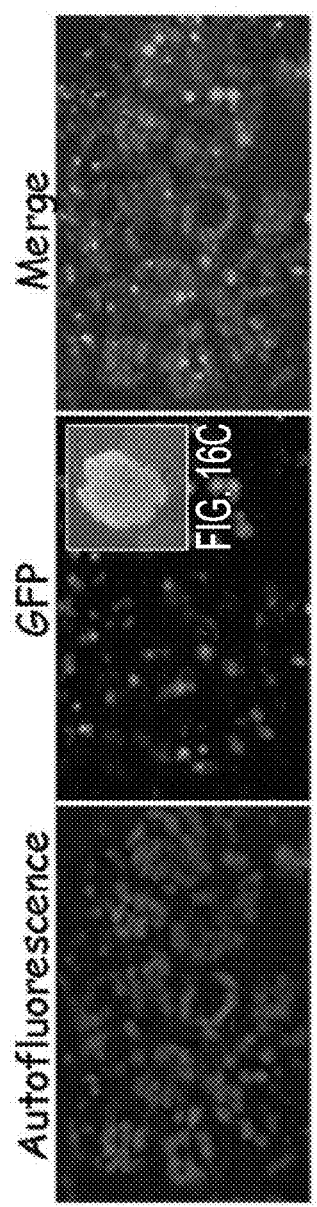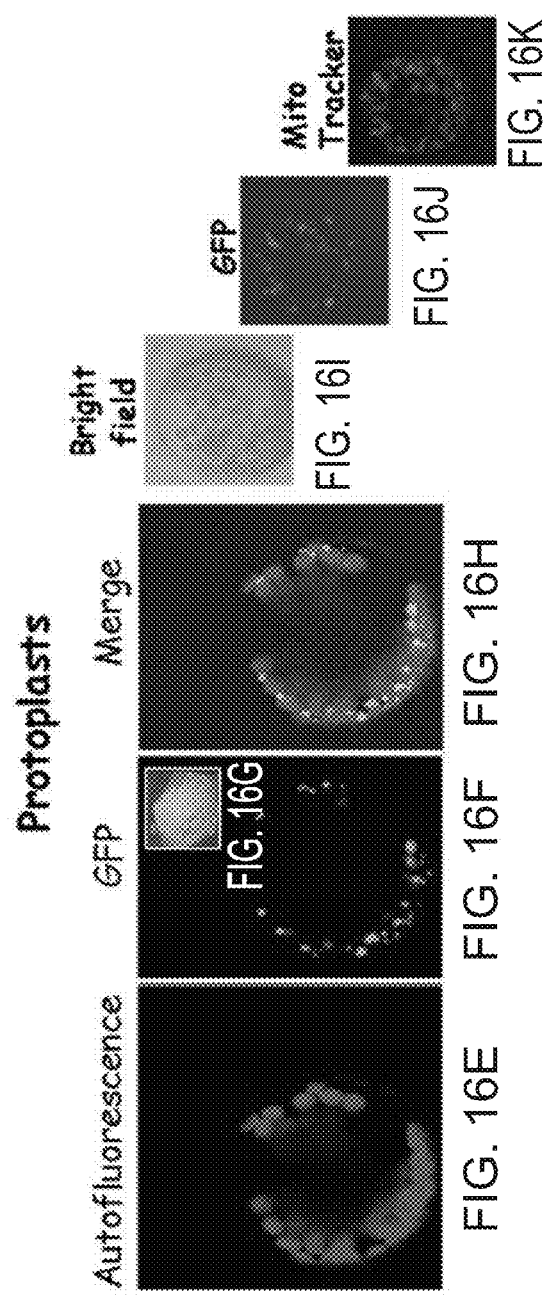

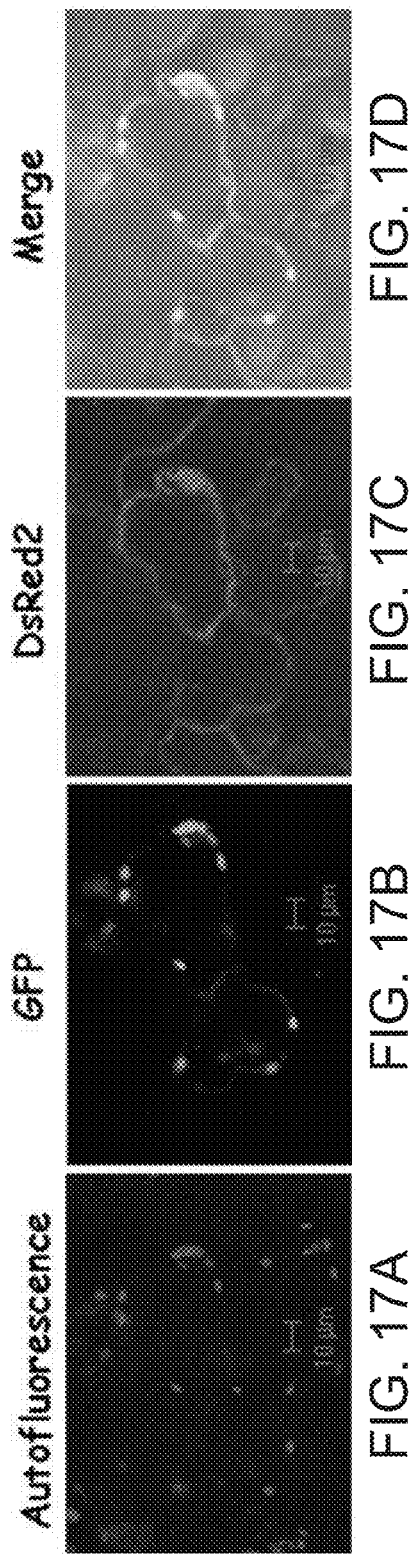

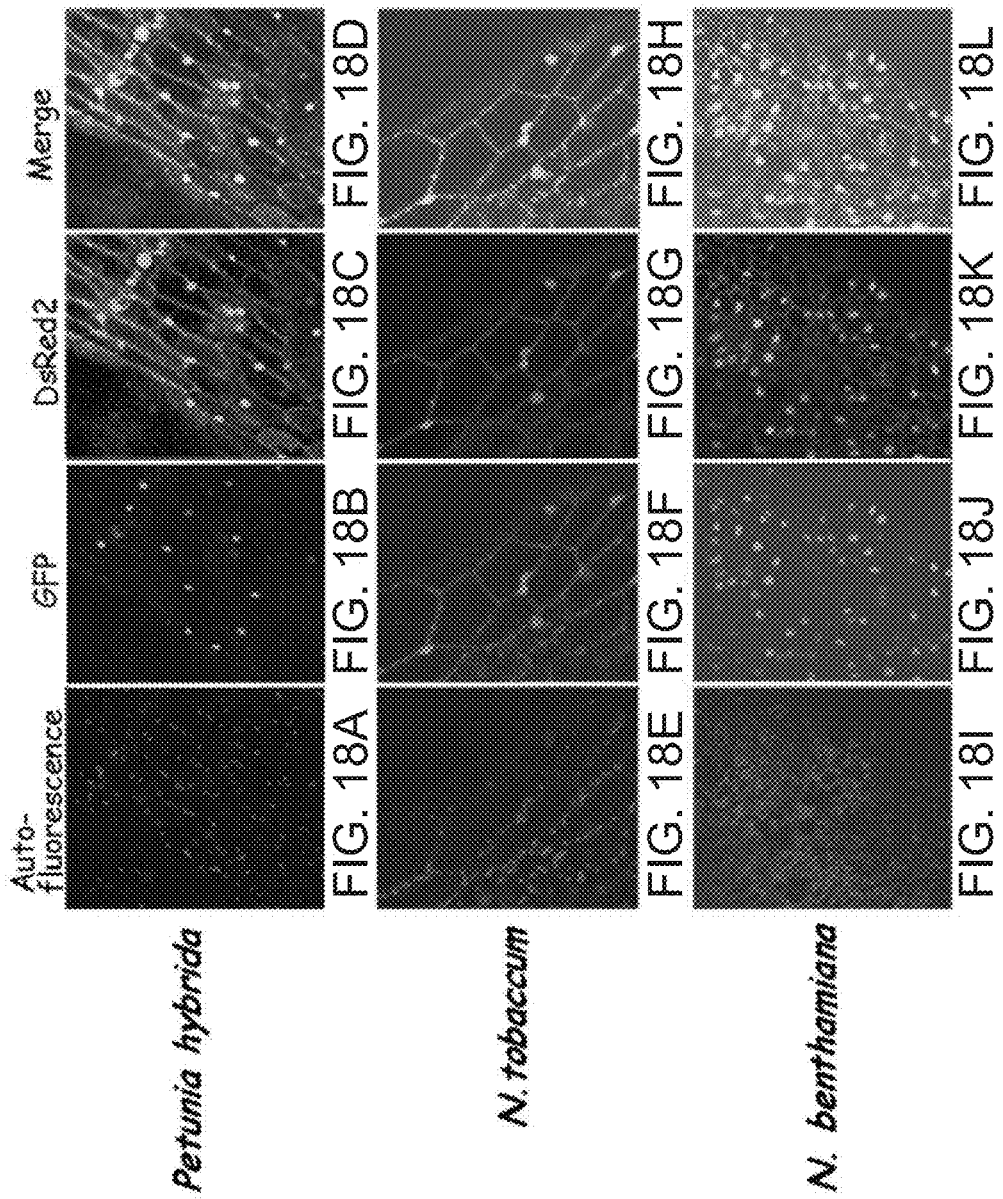

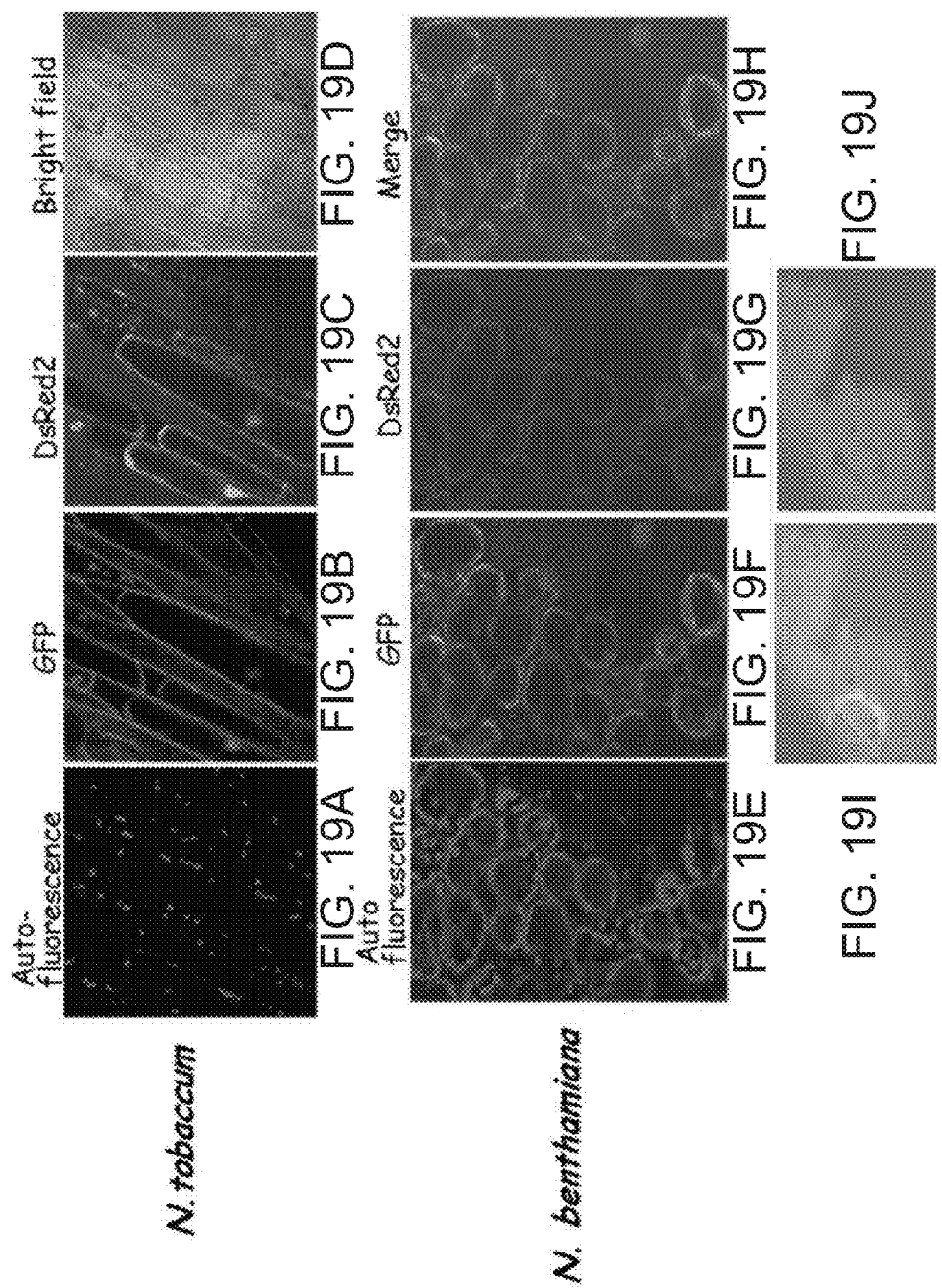

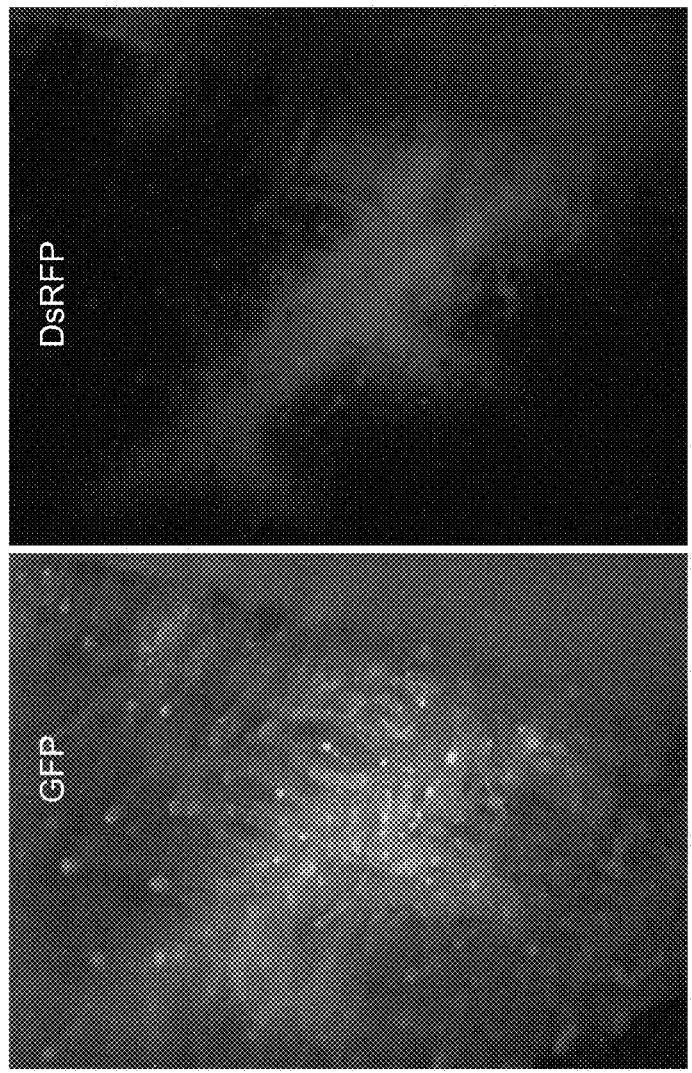

ATG TTC TTC CCC TCC TGA GGG GAA GAA TTA (SEQ ID NO: 92)
 M   F   F   P   S   *   G   E   E   L  (SEQ ID NO: 93)

FIG. 25A

ATG TTC TTC CCC TCC TGA GGG GAA GAA TTA (SEQ ID NO: 94)
 M   F   F   P   S       G   E   E   L  (SEQ ID NO: 95)

FIG. 25B

FIG. 26A 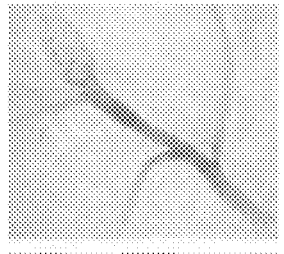 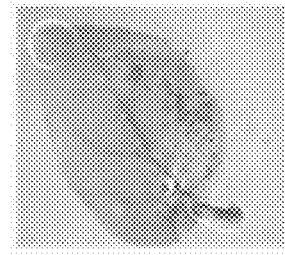 FIG. 26B
FIG. 26C 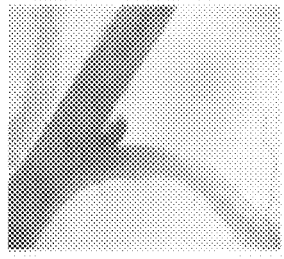 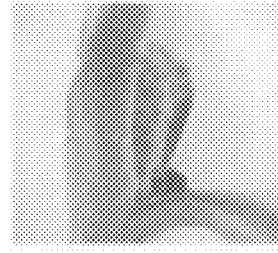 FIG. 26D
FIG. 26E 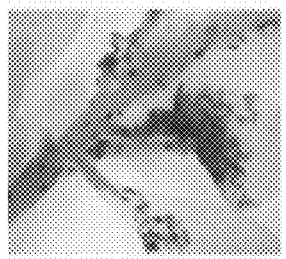  FIG. 26F
FIG. 26G 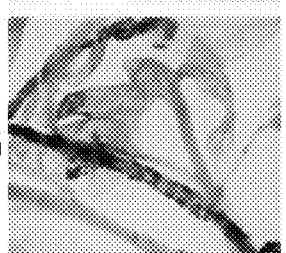 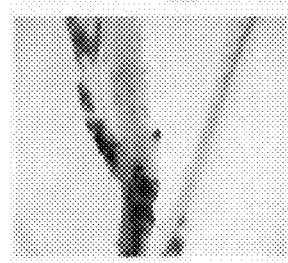 FIG. 26H
FIG. 26I 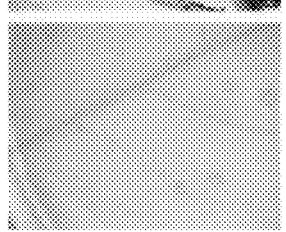 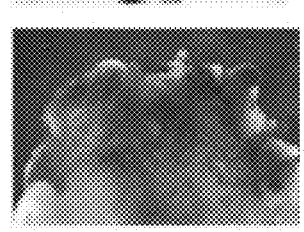 FIG. 26J

FIG. 27

FIG. 28A caggagaaacatggttcaaaaatggcctttttagatgtaatcctcctgagagactttgcatgccgattgttgaaca

78  TATTGAGTCAAAAGGTGGCCAAGTCAGAGACTAAACTCACGAATAA

122 GAAAGATCGAGCTGAACGAGGATGGAAGTGTCAAGTGTTTATACT

*MfeI (MunI)*        PDS-ZFN1

168 GAATAATGGCACTTCAATTGAGGGAGATGCATTCGTGTTTGCTGCT

GTGAACTTA ACTC CCTCTACGT    SEQ ID NO 132
              PDS-ZFN2

214 CCAG    SEQ ID NO 131

PDS-ZFN1 target site - *SEQ ID NO 140*
PDS-ZFN2 target site - *SEQ ID NO 141*

CACACTGATCC AGGAACCATC ACTCTCTGT TACAAGACCA

42 AGTTGGTGGG CTTCAAGCTA CTAAAGATAA TGGCAAAACT

EcoNI (XagI)    FHT-ZFN1

82 TGGATCA CTGTTCAGCC CTGTT GAAGGTGCT TTTGTTGTCA   SEQ ID NO 134
                                   GACAAGTTGG GACAACTTCCACGA   SEQ ID NO 133
                                   FHT-ZFN2

122 ATCTTGGTGA CCACGGTCAT

FHT-ZFN1 target site - SEQ ID NO 142
FHT-ZFN2 target site - SEQ ID NO 143

FIG. 31A

The sequence of NLS-PDS-ZFN1

ATGGTGccaaaaaagaagagaaggtagaagagacccCTCTCGAGCTGAAAAACCTTACAAGTGTCCT
GAATGTGGAAAGTCTTTTCTCAGTCTGGAGATTTGCGTCGTCACCAGCGAACACACACA
GGTGAGAAGCCATATAAATGCCCAGACACCGGAGAGCCATCAGTACTTCTGGAAATTTG
GTTCGTCACCAACGGACCCACACCGGGGAGAAGCCATTAAATGCCCTGAGTGCGGGA
AGAGTTTTTCACAGCGCGCGCATCTGGAACGCCATCAACGTACTCATACTGGAGGACTA
GTCAAAAGTGAACTGGAGGAGAAGAAATCTGAACTTCGTCATAAATTGAAATATGTGCCT
CATGAATATATTGAATTTTTATGAAAGTTATGGATATAGAGGTAACATTTGGGTGGATC
AAGGAAACCGACGGAGCAATTTATACTGTCGGATCTCCTATTGGCCAAGCAGATGAATGCA
GGATACTAAAGCTTATAGCGGAGGTTATAATCTGCCAAGCAGATGAATGCA
ACGATATGTCGAAGAAAATCAAACACGAAATTTAAGTTTTTATTGTGAGTGGTCACTTTAAAGGA
AGTCTATCCATCTTCTGTAACGGAATTTACGATTAAATCATCATATCACTAATTGTGAGTGCTGTCTTA
AACTACAAAGCTCAGCTTTTAATTGGTGGAGAAATGATTAAAGCCGGCACATTAACCTTAGAGG
AAGTGAGACGGGAAATTTAATAACGGCGAGATAAACTTTGGATCCTAA

*SEQ ID NO 70*

FIG. 31B

The sequence of NLS-PDS-ZFN2

ATGGTGccaaaaaagaagagaagaaggtagaagaccccTCTCGAGCTGAAAAACCTTACAAGTGTCCT
GAATGTGGAAAGTCTTTTCTCGCAGCGATGAACTGGTGCGCCACCAGCGAACACACAC
AGGTGAGAAGCCATATAAATGCCCAGAATGTGGTAAATCATTCAGTCAGTCTAGCAACCT
GGTTAGACACCAACGGACCCACACCGGGAGAAGCCATTAAATGCCCTGAGTGCGGG
AAGAGTTTTCACATAAAAACGCGCTGCAGAAGAACCATCAACGTACTCATACTGGAGGACTA
GTCAAAAGTGAACTGGAGGAGAAGAAATCTGAACTTCGTCATAAATTGAAATATGTGCCT
CATGAATATATTGAATTTTTATGAAGTTTATGGATATAGAGGTAAACATTTGGGTGGATC
AAGGAAACCGGACGGAGCAATTTATACTGTCGGATCTCCTATTGATTACGGTGTGATCGT
GGATACTAAAGCTTATAGCGGAGGTTATAATCTGCCAAGCAGATGAAATGCA
ACGATATGTCGAAGAAAATCAAACACGAAACAACATATCAACCTAATGAATGGTGGAA
AGTCTATCCATCTCTCTGTAACGGAATTAAGTTTTATTTGTGAGTGGTCACTTTAAAGGA
AACTACAAAGCTCAGTTACACGTTAATGATGGAGAAATGATTAAAGCCGGCACATTAACCTTGTTCTTA
GTGTAGAAGAGCTTTTAATTGGTGGAGAAATGATTAAAGCCGGCACATTAACCTTAGAGG
AAGTGAGACGGAAATTTAATAACGGCGAGATAAACTTTGGATCCTAA

*SEQ ID NO 72*

FIG. 32A

The sequence of NLS-FHT-ZFN1

ATGGTGCcaaaaagaagagaaggtagaagaccccTCTCGAGCTGAAAAACCTTACAAGTGTCCT
GAATGTGGAAAGTCTTTTCTACTTCTGGAGAATTGGTTCGTCACCAGCGAACACACA
GGTGAGAAGCCATATAAATGCCCAGAATGTGGTAAATCATTCAGTACTTCTGGACATCTT
GTTCGTCACCAACGGACCCACACCGGGAGAAGCCATTTAAATGCCCTGAGTGCGGGA
AGAGTTTTCACAGAGCAGCAACCTGGTGCCGCCATCAACGTACTCATACTGGAGGACTA
GTCAAAAGTGAACTGGAGGAGAAGAAATCTGAACTTCGTCATAAATTGAAATATGTGCCT
CATGAATATATTGAATTTTTATGAAGTTTATGGATATAGAGGTAACATTTGGGTGGATC
AAGGAAAACCGGACGGAGCAATTTATACTGTCGGATCTCCTATTGATTACGGTGTGATCGT
GGATACTAAGCTTATAGCGGAGGTTATAATCTGCCAATTGGCCAAGCAGATGAAATGCA
ACGATATGTCGAAGAAATCAAACACGAAACAAACATATCAACCCTAATGAATGGTGGAA
AGTCTATCCATCTCTGTAACGGAATTTAAGTTTTATTTGTGAGTGGTCACTTTAAAGGA
AACTACAAAGCTCAGCTTACACGATTAAATCATATCACTAATTGTAATGGAGCTGTCTTA
GTGTAGAAGAGCTTTTAATTGGTGGAGAAATGATTAAAGCCGGCACATTAACCTTAGAGG
AAGTGAGACGGAAATTTAATAACGGCGAGATAAACTTTGGATCCTAA

SEQ ID NO 74

FIG. 32B

The sequence of NLS-FHT-ZFN2

ATGGTGccaaaaagagaagaagtagaagaccccTCTCGAGCTGAAAAACCTTACAAGTGTCCT
GAATGTGGAAAGTCTTTTCGCGGGATAACCTGACCGAACACCAGCGAACACACAC
AGGTGAGAAGCCATATAAATGCCCAGAATGTGTAAATCATTCAGTCAGTCAGCAACCT
GGTTAGACACCAACGGACCCACACCGGGGAGAAGCCATTTAAATGCCCTGAGTGCGGG
AAGAGTTTTTCAACTTCTGGAGAGAGAAGAATTGGTTCGTCATCAACGTACTCATCGGAGGACTA
GTCAAAAGTGAACTGGAGGAGAAGAAATCTGAACTTCGTCATAAATTGAAATATGTGCCT
CATGAATATATTGAATTTTTATGAAAGTTTATGGATATAGAGGTAAACATTTGGGTGGATC
TGAAGGTAATGGAGGAGCAATTACTGTCGGATCTCCTATTGATTGATTACGGTGTGATCGT
AAGGAAACCGGAGCTAAAGCTTATAGCGGGAGGTTATAATCTGCCAAGCAGATGAAATGCA
GGATACTAAAGCTAAAGCAACAATCAAACAGAAACAAACATATCAACCCTAATGAATGGTGGAA
ACGATATGTCGAAGAATCAAACGGAATTTAAGTTTTTATTTGTGAGTGCACTTTAAAGGA
AGTCTATCCATCTTCTGTAACGCTTACACGATTAAATCATCACTAATTGTAATGGAGCTGTCTTA
AACTACAAAGCTCAGCTTTTAATTGGTGGAGAAATGATTAAAGCCGCACATTAACCTTAGAGG
GTGTAGAAGAGCTTAATTGGTGGAGACGGAAATTAATAACGGCGAGATAAACTTTGGATCCTAA
AAGTGAGACGGAAATTTAATAACGGCGAGATAAACTTTGGATCCTAA

SEQ ID NO 76

GENERATING GENOTYPIC VARIATIONS IN PLANT GENOMES BY GAMETE INFECTION

RELATED APPLICATIONS

This application is a National Phase of PCT Patent Application No. PCT/IL2010/000874 having International filing date of Oct. 21, 2010, which claims the benefit of priority of U.S. Provisional Patent Application No. 61/272,684 filed on Oct. 21, 2009. The contents of the above applications are all incorporated herein by reference.

SEQUENCE LISTING STATEMENT

The ASCII file, entitled 52929SequenceListing.txt, created on 2012, 3 Aug., comprising 96,965 bytes, submitted concurrently with the filing of this application is incorporated herein by reference.

FIELD AND BACKGROUND OF THE INVENTION

The present invention, in some embodiments thereof, relates to plant viral expression vectors and, more particularly, but not exclusively, to the use of same for generating genotypic variations in plant genomes and specifically in the plant reproductive organs.

Genetic modification and improvement of crop plants as well as protection of new varieties is fundamental for modern agriculture. During the past several years an enormous amount of data was obtained from the various large genome-sequencing projects allowing significant progress in agriculture transgenic technologies. Such technologies, including gene expression, gene modification, site-specific gene mutagenesis and gene targeting of plant genome sequences, allow development of basic plant research models and can be directly used for genetic improvement and protection of agronomically important plant species.

Foreign DNA molecules (e.g. T-DNA) delivered by *Agrobacterium* are integrated in the plant's genome into natural double strand breaks (DSBs) which may be generated by rare-cutting restriction enzymes. These DSBs are recognized and repaired by plant non-homologous end joining (NHEJ) proteins and results in the frequent integration of the foreign DNA into these random sites [Salomon et al. EMBO J. (1998) 17: 6086-6095; Tzfira et al. Plant Physiol (2003) 133: 1011-1023, Tzfira et al. Trends Genet (2004) 20: 375-383]. The DSBs may also result in enhanced homologous recombination (HR)-based gene targeting in plant cells [Puchta et al. Proc Natl Acad Sci USA (1996) 93: 5055-5060].

Recent developments in the field of zinc finger nucleases (ZFNs) as novel tools for genome modifications offer new prospects for site-specific induction of DSBs in plant genomes and for the development of NHEJ-based methods for gene targeting in plant species and plant protection. ZFNs are synthetic restriction enzymes which can be specifically designed to bind and cleave virtually any long stretch of dsDNA sequences (see FIG. 1). ZFNs were shown suitable for site-specific genomic DSB induction in plant species using non-viral vectors [Lloyd et al. Proc. Natl. Acad. Sci. U. S. A. (2005) 102: 2232-2237; Tovkach et al. The Plant Journal (2009) 57, 747-757]. Similar effects were shown on human [Moehle et al. Proc Natl Acad Sci USA (2007) 104: 3055-3060] and insect genomes [Beumer et al. Genetics (2006) 172: 2391-2403].

The use of plant viruses as vehicles to introduce and express nonviral genes in plants is well documented [e.g. Donson et al., Proc Natl Acad Sci USA. (1991) 88: 7204-8; Chapman et al. Plant J. (1992) 2: 549-57; Dolja et al., Virology (1998) 252: 269-74]. Infection of plants with modified viruses is simpler and quicker than the regeneration of stably transformed plants (as discussed above) since plant viruses are often small in size (between 3000 and 10,000 nucleotides), are easy to manipulate, have the inherent ability to enter the plant cell, lead to the immediate expression of the heterologous gene and will multiply to produce a high copy number of the gene of interest. Viral vectors have been engineered for delivery of genetic material and expression of recombinant proteins in plants [e.g., Pogue, Annu. Rev. Phytopathol. (2002) 40: 45-74; Gleba, et al., Curr. Opin. Plant Biol. (2004) 7: 182-188; Dolja et al., Proc. Natl. Acad. Sci. USA (1992) 89: 10208-10212; U.S. Pat. No. 5,316,931 and U.S. Pat. No. 5,811,653 for RNA virus vectors]. Viral expression systems are considered transient expression systems as the viral vectors are not integrated into the genome of the host, however, depending on which virus is used, virus multiplication and gene expression can persist for long periods (up to several weeks or months).

To date the use of viral vectors for introducing DSBs in plant genomes was not demonstrated or suggested.

RELATED ART

U.S. Pat. No. 7,229,829 discloses TRV vectors (TRV-RNA1 and TRV-RNA2) carrying heterologous nucleic acid sequences for delivery into plants for transforming plants and plant cells. Specifically, U.S. Pat. No. 7,229,829 teaches vectors for virus induced gene silencing (VIGS) including vectors designed for suppression of host plant gene expression (e.g. antisense transcripts for knocking out expression of genes without the need to genetically transform the plant) or vectors designed for expression of heterologous nucleic acids (e.g. nucleic acids mediating gene silencing or gene suppression).

U.S. Publication Nos. 20050026157 and 20070134796 discloses compositions and methods for targeted cleavage of cellular chromatin and for targeted alterations (e.g. insertions) of cellular nucleotide sequences. To target specific genomic sites, fusion proteins are constructed which comprise a zinc finger domain and a cleavage domain [i.e. zinc finger proteins (ZFPs)]. Moreover, U.S. Publication No. 20070134796 teaches vectors (e.g. bacterial vectors such as plasmid vectors and viral vectors such as adenoviral and retroviral vectors) comprising the ZFPs.

PCT Publication No. WO07139982 discloses methods and compositions for inactivating human genes (e.g. CCR5 gene) using zinc finger nucleases (ZFNs). The ZFNs comprise a zinc finger protein (may include 1, 2, 3, 4, 5, 6 or more zinc fingers) and a cleavage domain or cleavage half-domain (i.e., a nuclease domain). Furthermore, PCT Publication No. WO07139982 teaches vectors comprising ZFNs and/or a donor sequence for targeted integration into a target gene.

U.S. Pat. Nos. 7,309,605 and 6,610,545 disclose nucleotide sequences encoding the enzyme I-SceI (a double-stranded endonuclease that cleaves DNA within its recognition site). These sequences can be incorporated in cloning and expression vectors (such as plasmid, bacteriophage or cosmid vectors) and may be used to transform cell lines and transgenic organisms (e.g. mammals, plants). The vectors

SUMMARY OF THE INVENTION

According to an aspect of some embodiments of the present invention there is provided a method of generating genotypic variation in a genome of a plant, the method comprising introducing into a gamete or a gamete producing tissue of the plant at least one viral expression vector encoding at least one chimeric nuclease which comprises a DNA binding domain, a nuclease and a localization signal to a DNA-containing organelle, wherein the DNA binding domain mediates specific targeting of the nuclease to the genome of the plant, and wherein the introducing is performed such that the gamete or gamete producing tissue expresses the chimeric nuclease but not all plant tissues express the chimeric nuclease, thereby generating genotypic variation in the genome of the plant.

According to an aspect of some embodiments of the present invention there is provided a method of treating a plant infection by a pathogen, the method comprising introducing into a gamete or a gamete producing tissue of the plant at least one viral expression vector encoding at least one chimeric nuclease which comprises a DNA binding domain and a nuclease, wherein the DNA binding domain mediates targeting of the nuclease to the genome of the pathogen, and wherein the introducing is performed such that the gamete or gamete producing tissue expresses the chimeric nuclease but not all plant tissues express the chimeric nuclease, thereby preventing or treating a plant infection by a pathogen.

According to an aspect of some embodiments of the present invention there is provided a method of tagging a genome of a plant, the method comprising introducing into a gamete or a gamete producing tissue of the plant at least one viral expression vector encoding at least one chimeric nuclease which comprises a DNA binding domain, a nuclease and a localization signal to a DNA-containing organelle, wherein the DNA binding domain mediates specific targeting of the nuclease to the genome of the plant, and wherein the introducing is performed such that the gamete or gamete producing tissue expresses the chimeric nuclease but not all plant tissues express the chimeric nuclease, thereby tagging the genome of the plant.

According to an aspect of some embodiments of the present invention there is provided a method of generating male sterility in a plant, the method comprising upregulating in the plant a structural or functional gene of a mitochondria or chloroplast associated with male sterility by introducing into a gamete or a gamete producing tissue of the plant at least one viral expression vector encoding at least one chimeric nuclease which comprises a DNA binding domain, a nuclease and a mitochondria or chloroplast localization signal and a nucleic acid expression construct which comprises at least one heterologous nucleic acid sequence which can upregulate the structural or functional gene of a mitochondria or chloroplast when targeted into the genome of the mitochondria or chloroplast, wherein the DNA binding domain mediates targeting of the heterologous nucleic acid sequence to the genome of the mitochondria or chloroplast, and wherein the introducing is performed such that the gamete or gamete producing tissue expresses the chimeric nuclease but not all plant tissues express the chimeric nuclease, thereby generating male sterility in the plant.

According to an aspect of some embodiments of the present invention there is provided a method of generating a herbicide resistant plant, the method comprising introducing into a gamete or a gamete producing tissue of the plant at least one viral expression vector encoding at least one chimeric nuclease which comprises a DNA binding domain, a nuclease and a chloroplast localization signal, wherein the DNA binding domain mediates targeting of the nuclease to a gene conferring sensitivity to herbicides, and wherein the introducing is performed such that the gamete or gamete producing tissue expresses the chimeric nuclease but not all plant tissues express the chimeric nuclease, thereby generating the herbicide resistant plant.

According to an aspect of some embodiments of the present invention there is provided a plant viral expression vector comprising a nucleic acid sequence encoding at least one chimeric nuclease which comprises a DNA binding domain, a nuclease and a localization signal to a DNA-containing organelle.

According to an aspect of some embodiments of the present invention there is provided a pTRV based expression vector comprising a nucleic acid sequence encoding at least two heterologous polypeptide sequences.

According to an aspect of some embodiments of the present invention there is provided a plant cell comprising at least one chimeric nuclease, wherein the chimeric nuclease comprises a DNA binding domain, a nuclease and a localization signal to a DNA-containing organelle, and wherein the chimeric nuclease induces cleavage of a target sequence.

According to an aspect of some embodiments of the present invention there is provided a transgenic plant comprising the plant viral expression vector of claim 6 or 7.

According to an aspect of some embodiments of the present invention there is provided a method of generating a transgenic plant, the method comprising: introducing into one or more cells of the plant at least one viral expression vector encoding at least one chimeric nuclease which comprises a DNA binding domain, a nuclease and a localization signal to a DNA-containing organelle.

According to an aspect of some embodiments of the present invention there is provided an isolated polynucleotide comprising a nucleic acid sequence as set forth in SEQ ID NOs: 31, 32, 33, 34, 70, 72, 74, 76, 84, 86 or 88.

According to an aspect of some embodiments of the present invention there is provided an isolated polypeptide comprising an amino acid sequence as set forth in SEQ ID NOs: 35, 36, 37, 38, 71, 73, 75, 77, 85, 87 or 89.

According to some embodiments of the invention, generating genotypic variation is transient.

According to some embodiments of the invention, the genotypic variation comprises a nucleotide insertion, a nucleotide deletion or a combination of same.

According to some embodiments of the invention, the tagging comprises a nucleotide insertion, a nucleotide deletion or a combination of same.

According to some embodiments of the invention, the viral expression vector comprises a Tobacco Rattle Virus (TRV) expression vector.

According to some embodiments of the invention, the TRV expression vector comprises a pTRV2 based expression vector.

According to some embodiments of the invention, at least one viral expression vector encodes for two chimeric nucleases.

According to some embodiments of the invention, the at least one viral expression vector comprises two viral expression vectors.

According to some embodiments of the invention, the two viral expression vectors are introduced into the plant concomitantly.

According to some embodiments of the invention, introducing into the plant is effected by an *Agrobacterium*.

According to some embodiments of the invention, the *Agrobacterium* is effected by injection.

According to some embodiments of the invention, introducing the *Agrobacterium* is effected by leaf infiltration.

According to some embodiments of the invention, introducing into the plant is effected by virion infection.

According to some embodiments of the invention, the at least one chimeric nuclease comprises two chimeric nucleases.

According to some embodiments of the invention, the introducing is performed directly into the gamete-producing tissue.

According to some embodiments of the invention, the directly into the gamete-producing tissue is effected by flower infiltration or floral dip transformation.

According to some embodiments of the invention, the directly into the gamete-producing tissue is effected without meristem infection.

According to some embodiments of the invention, the at least one chimeric nuclease is selected from the group consisting of restriction enzymes, artificial meganucleases, modified meganucleases, homing nucleases; topoisomerases, recombinases, DNAses and integrases.

According to some embodiments of the invention, the plant viral expression vector or transgenic plant further comprises a second nucleic acid sequence encoding a heterologous polypeptide.

According to some embodiments of the invention, the plant viral expression vector or transgenic plant comprises a pTRV backbone.

According to some embodiments of the invention, the pTRV is a pTRV1 (GeneBank Accession No: AF406990).

According to some embodiments of the invention, the pTRV is a pTRV2 (GeneBank Accession No: AF406991).

According to some embodiments of the invention, the nucleic acid sequence is devoid of a 2b sequence (SEQ ID NO: 43).

According to some embodiments of the invention, the nucleic acid sequence comprises a Ω enhancer (SEQ ID NO: 44).

According to some embodiments of the invention, the nucleic acid sequence comprises two separate sub genomic promoters (sgPs) for regulating transcription of the at least two heterologous polypeptides.

According to some embodiments of the invention, the at least two heterologous polypeptide sequences are separated by nucleic acid sequence encoding a cleavage domain.

According to some embodiments of the invention, the cleavage domain comprises a T2A-like protein sequence (SEQ ID NO: 40).

According to some embodiments of the invention, the nucleic acid sequence of the at least two heterologous polypeptide sequences is as set forth in SEQ ID NOs: 84, 86 or 88.

According to some embodiments of the invention, the amino acid sequence of at least two heterologous polypeptide sequences are as set forth in SEQ ID NOs: 85, 87 or 89.

According to some embodiments of the invention, the at least two heterologous polypeptide sequences encode for a plant gene.

According to some embodiments of the invention, the at least two heterologous polypeptide sequences comprise chimeric proteins, wherein each of the chimeric proteins comprise a DNA binding domain, a nuclease and a localization signal to a DNA-containing organelle.

According to some embodiments of the invention, the localization signal comprises a ribulose-1,5-bisphospate carboxylase small subunit (RSSU) sequence (SEQ ID NO: 138).

According to some embodiments of the invention, the localization signal comprises an ATPase beta subunit (ATP-β) sequence (SEQ ID NO: 139).

According to some embodiments of the invention, the DNA binding domain binds a 9 nucleotide sequence.

According to some embodiments of the invention, the DNA binding domain comprises at least one zinc finger domain.

According to some embodiments of the invention, the zinc finger domain comprises three zinc finger domains.

According to some embodiments of the invention, the nuclease comprises a cleavage domain of a type II restriction endonuclease.

According to some embodiments of the invention, the type II restriction endonuclease is a FokI restriction endonuclease.

According to some embodiments of the invention, the plant comprises a *Petunia hybrida*.

According to some embodiments of the invention, the plant comprises a *Nicotiana tabacum*.

According to some embodiments of the invention, the plant in selected from the group consisting of an *Arabidopsis thaliana*, an *Artemisia* sp., a *Artemisia annua*, a *Beta vulgaris*, a *Solanum tuberosum*, a *Solanum pimpinellifolium*, a *Solanum lycopersicum*, a *Solanum melongena*, a *Spinacia oleracea*, a *Pisum sativum*, a *Capsicum annuum*, a *Cucumis sativus*, a *Nicotiana benthamiana*, a *Nicotiana tabacum*, a *Zea mays*, a *Brassica napus*, a *Gossypium hirsutum* cv. Siv'on, a *Oryza sativa* and a *Oryza glaberrima*.

According to some embodiments of the invention, the cell is a meristem cell.

According to some embodiments of the invention, the DNA-containing organelle is selected from the group consisting of a nucleus, a chloroplast and a mitochondria.

According to some embodiments of the invention, the specific targeting of the nuclease to the genome of the *Petunia hybrida* is to a phytoene desaturase (PDS) or a flavanone 3 beta-hydroxylase (FHT) of the *Petunia hybrida*.

According to some embodiments of the invention, the mitochondria localization signal comprises an ATPase beta subunit (ATP-β) (SEQ ID NO: 139).

According to some embodiments of the invention, the chloroplast localization signal comprises a ribulose-1,5-bisphospate carboxylase small subunit (Rssu) (SEQ ID NO: 138).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of Zinc-finger nucleases (ZFNs) as a tool for the induction of genomic double-strand breaks (DSBs). FIG. 1A depicts the structure of ZFNs chimeric genes composed of a synthetic DNA-recognition domain consisting of three C2H2 zinc fingers fused to a non-specific DNA restriction enzyme (usually the FokI endonuclease); FIG. 1B depicts custom-made ZFN genes, in which each finger recognizes a three-nucleotide sequence and can potentially be designed to recognize any combination of nine nucleotides (exemplified here by a GGGGAAGAA target sequence, SEQ ID NO: 42). Since FokI functions as a dimer, two sets of ZFNs are used to bind the target DNA, which results in a unique combination of 18 nucleotides; FIG. 1C depicts binding of the ZFNs to the target DNA; FIG. 1D depicts digestion of the DNA by FokI endonuclease domain and creation of a double-strand break (DSB). FIG. 1E depicts repair of the DSBs by non-homologous end-joining (NHEJ) proteins that lead to deletion or insertion mutations at the repair site.

FIG. 2A shows sequence alignment between the sequence of *Thosea asigna* virus for the self cleaving peptide (Tav-T2A, SEQ ID NO: 51) and the modified sequence according to the codon usage of *Petunia* (pTRV-T2A, SEQ ID NO: 52).

FIG. 2B shows P1-25 *Petunia* RB random DNA fragment (SEQ ID NO: 8).

FIG. 3 shows P1-36 *Petunia* RB random DNA fragment (SEQ ID NO: 9).

Figure 4:
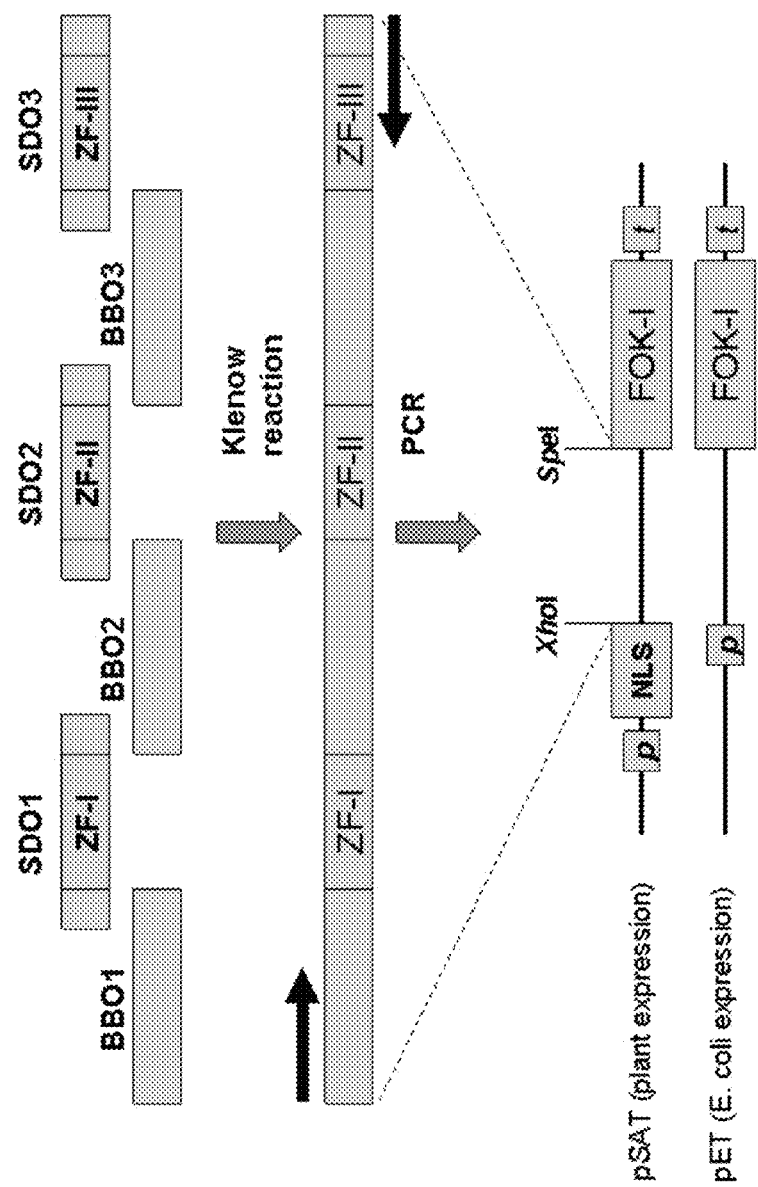

FIG. 4 is a schematic illustration of a ZFN structure constructed according to the present teachings. The ZFN construct comprises a nuclear localization signal (NLS), a Zink Finger DNA binding domain and a DNA nuclease domain from FokI.

FIGS. 5A-D shows the sequences of NLS-P1-25-ZFN1, NLS-P1-25-ZFN2, NLS-P1-36-ZFN1 and NLS-P1-36-ZFN2. The sequence is of the full chimera: NLS, ZFN and FokI (d-domain). Sequences of nuclear localization signal (NLS) are depicted in lower case; nuclease (FokI-domain d) first codon and the termination codon are depicted in bold. FIG. 5A shows the sequence of NLS-P1-25-ZFN1 (SEQ ID NO: 31); FIG. 5B shows the sequence of NLS-P1-25-ZFN2 (SEQ ID NO: 32); FIG. 5C shows the sequence of NLS-P1-36-ZFN1 (SEQ ID NO: 33); and FIG. 5D shows the sequence of NLS-P1-36-ZFN2 (SEQ ID NO: 34).

FIG. 5E is a scheme showing the original pET28 vector (SEQ ID NO: 39, commercial available from Novagen) and the modified pET28 vector (SEQ ID NO: 49), pET28c.SX, comprising a modification of MCS. To construct pET28c-SX, nucleotides 179 to 158 (indicated by bold) were deleted from MSC of pET28c by digestion with SalI and XhoI.

FIGS. 6A-D are schematic maps of pTRV2 (GenBank accession No. AF406991) and its modifications. FIG. 6A is a schematic illustration of the complete pTRV2 expression vector; FIG. 6B depicts the removal of the 2b 5' CDS fragment; FIG. 6C depicts the addition of 5'UTR of TMV (Ω); and FIG. 6D depicts the addition of sgP-CP from PEBV.

Figure 6E:
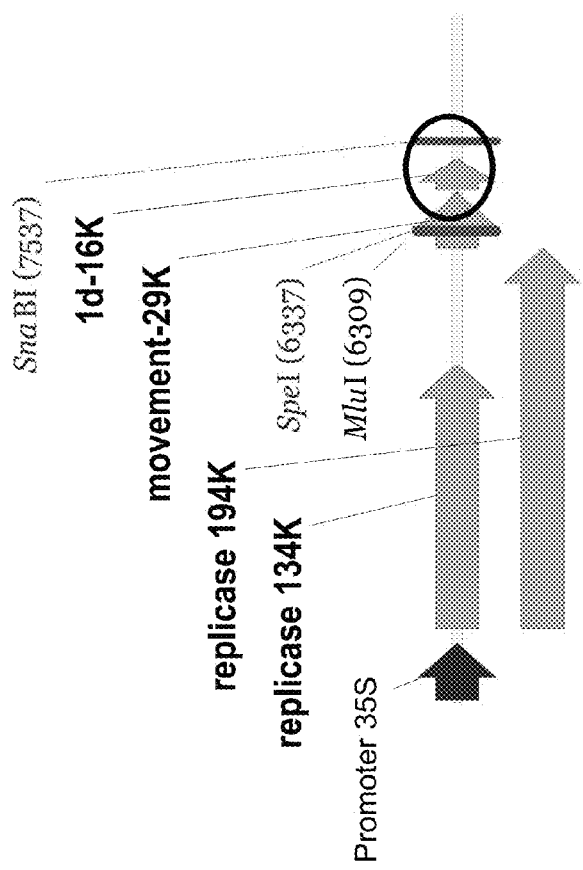

FIG. 6E is schematic maps of part of pTRV1 showing RNA1 (GenBank accession No. AF406990).

FIGS. 7A-E are pictures illustrating the expression of GUS in meristems of *petunia* plants inoculated with pTRV2-GUS and pTRV2-Δ2b-GUS. FIGS. 7A-B depict meristems from *petunia* plants 7 days after stem inoculation with the vectors; and FIGS. 7C-D depict meristems from *petunia* plants 37 days after stem inoculation with the vectors. Plants inoculated with pTRV2-GUS are shown in FIGS. 7A and 7C. Plants inoculated with pTRV2-Δ2b-GUS are shown in FIGS. 7B and 7D. FIG. 7E shows GUS staining in *petunia* plants propagated in vitro 6 month following inoculation with pTRV2-Δ2b-GUS.

FIGS. 8A-G are pictures illustrating the expression of marker genes in various plants following inoculation with pTRV2 based vectors. FIG. 8A depicts GUS staining (24 days post inoculation) of pepper plants (*Capsicum annuum*, Endra-1750) inoculated with pTRV2-Δ2b-GUS; FIG. 8B depicts GFP staining (41 days post inoculation) of pepper plants (*Capsicum annuum*, Endra-1750) inoculated with pTRV2-Δ2b-GFP; FIG. 8C depicts GUS staining (13 and 30 days post inoculation) of *Arabidopsis* plants inoculated with pTRV2-GUS; FIG. 8D depicts GUS staining (14 days post inoculation) of tomato plants (*Solanum pimpinellifolium* La121) inoculated with pTRV2-Δ2b-ΩGus; FIG. 8E depicts GFP staining (31 days post inoculation) of *Nicotiana benthamiana* plants inoculated with pTRV2-Δ2b-GFP, FIG. 8F depicts GUS staining (44 days post inoculation) of *Nicotiana benthamiana* plants inoculated with pTRV2-35SΩGUS; and FIG. 8G depicts pigmentation of *Nicotiana benthamiana* inoculated with pTRV2-Δ2b-PAP (76 days post inoculation).

FIGS. 9A-B are pictures illustrating GUS staining 51 days post inoculation of *petunia* plants with pTRV2-Δ2b-ΩGUS (FIG. 9A) as compared to pTRV2-Δ2b-GUS (FIG. 9B). Of note, arrows point to meristematic regions.

FIGS. 10A-C are pictures illustrating co-expression of two genes in meristems of *N. benthamiana* plants. FIG. 10A depicts plants inoculated with pTRV2-Δ2b-sgP-GFP. GFP staining was evaluated 17 days post inoculation with pTRV2-Δ2b-sgP-GFP; FIGS. 10B-C depict plants co-inoculated with pTRV2-Δ2b-GUS and pTRV2-Δ2b-GFP. GFP staining was evaluated 17 days post inoculation (FIG. 10B) followed by GUS staining on the same tissue sample (FIG. 10C).

FIGS. 11A-F are pictures illustrating virus-mediated gene expression (DsRed) in cells of different plants. Plants were inoculated with pTRV1 and pTRV2-Δ2b-sgP-DsRed and fluorescence was evaluated using confocal laser scanning microscopy. Upper panel (FIGS. 11A, C, E) shows cells' chlorophyll autofluorescence and lower panel (FIGS. 11B, D, F) shows DsRed fluorescence in the same cells. Autofluorescence was evaluated at excitation (Ex) 488 nm and emission (Em) at more than 650 nm, DsRed was evaluated at ex 545 nm and em between 585-615 nm.

FIGS. 12A-H are pictures illustrating long term gene expression (DsRed) in different plants following inoculation with pTRV1 and pTRV2-Δ2b-sgP-DsRed. Images were obtained using fluorescent stereomicroscope. DsRed fluorescence (FIGS. 12A, C, D, G) was visible in different parts of plants, including roots (FIGS. 12D, F). Lower panel (FIGS. 12B, E, F, H) shows (the same) images taken under bright field. Of note, *N. Benthamiana* was innoculated with TRV virions and *N. tabaccum* and *Petunia hybrida* were innoculated via agro-infiltration.

FIGS. 13A-K are pictures illustrating the applicability of the TRV2 vector for expression of foreign genes in various plants. Expression of the marker genes GUS, GFP and DsRed was demonstrated in various plants belonging to different families following inoculation with TRV vectors: *Beta vulgaris* (FIG. 13E) were inoculated with pTRV-Δ2b-GUS (sample GUS stained 20 days post inoculation); *Solanum melongena* (FIGS. 13F-G) was inoculated with pTRV-Δ2b-sgP-Rssu-EGFP (evaluated 5 days post inoculation); *Cucumis sativus* (FIGS. 13A-B), *Gossypium hirsutum* cv. Siv'on (FIGS. 13H-I) and *Brassica napus* (FIGS. 13J-K) were inoculated with pTRV-Δ2b-sgP-DsRed (evaluated 5, 7 and 16 days post inoculation, respectively). Bright field images were also demonstrated. *Spinacia oleracea* (FIGS. 13C-D) was inoculated with pTRV-Δ2b-GUS (FIG. 13C, sample GUS stained 20 days post inoculation) and pTRV-Δ2b-sgP-DsRed (FIG. 13D, evaluated 12 days post inoculation). All images were taken using fluorescent stereomicroscope.

FIGS. 14A-C are pictures illustrating expression of DsRed2 in *Zea mays* Var. Royalty coleoptile by TRV viral vectors. Seeds were inoculated with sap containing diluted virions, extracted from *Petunia* agroinfiltrated with pTRV1 and pTRV2-Δ2b-sgP-DsRed. DsRed was evaluated at 16 days post inoculation (dpi). Visible (FIG. 14A), DsRed (FIG. 14B) and Merged (FIG. 14C).

FIGS. 15A-G are pictures illustrating chloroplast-targeted expression of EGFP in *petunia* and tobacco following infection with pTRV2-sgP-Rssu-EGFP. *N. Tabacuum* cv Samsung and *Petunia hybrida* CV. RB were inoculated with pTRV2-sgP-Rssu-EGFP and the expression of EGFP in chloroplasts was assayed approximately 9 days post inoculation. Autofluorescence (FIGS. 15A, E) of chlorophyll: was evaluated at excitation (ex) 488 nm and emission (em) was evaluated at more than 650 nm. The EGFP (FIGS. 15B, F) was detected by ex at 488 and em between 505-530 nm. Merged signal (FIGS. 15D and G, overlay of pink and green yielding yellow). Inset (FIG. 15C) shows tissue expressing EGFP visualized by fluorescent stereomicroscope.

FIGS. 16A-K are pictures illustrating mitochondrial-targeted expression of EGFP in *petunia* following infection with pTRV2-sgP-ATPβ-EGFP. *Petunia hybrida* CV. RB were inoculated with pTRV2-sgP-ATPβ-EGFP and expression of EGFP in mitochondria was assayed approximately 5 days post inoculation. Autofluorescence (FIG. 16A) was evaluated at ex 488 and em at more than 650 nm EGFP (FIG. 16B) was evaluated at ex. 488 and em between 505-530 nm. Protoplast (FIGS. 16E-K) were prepared from *Petunia* RB expressing mitochondrial targeted EGFP, stained with MitoTracker and evaluated at ex 545 nm and em between 585-615 nm. Inset (FIG. 16G) shows tissue expressing EGFP visualized by fluorescent stereomicroscope.

FIGS. 17A-D are pictures illustrating co-expression of marker genes in different cellular compartments. DsRed was expressed in the cytosol and GFP in the chloroplasts of *N. tabacum* cv. Xanthi leaf cells. Plants were co-infected with pTRV1 and pTRV2-Δ2b-sgP-DsRed and pTRV2-Δ2b-sgP-Rssu-EGFP. Autofluorescence (FIG. 17A) was evaluated using ex 488 nm and em of more than 650 nm, GFP (FIG. 17B) was evaluated using ex 488 nm and em between 505-530 nm, DsRed (FIG. 17C) was evaluated using ex 545 nm and em between 585-615 nm, Merge (FIG. 17D) depicts a merge of all three filters (merged signals).

FIGS. 18A-L are pictures illustrating co-expression of DsRed and EGFP in different plants using pTRV2 constructed with the two reporter genes in tandem separated by T2A. Plants (*Petunia hybrida*, *N. tobaccum* and *N. benthamiana*) were inoculated with pTRV1 and pTRV2-Δ2b-sgP-DsRed-T2A-NLS-EGFP. Fluorescence was evaluated using confocal laser scanning microscopy. Cells' chlorophyll autofluorescence (FIGS. 18A, E, I), EGFP (FIGS. 18B, F, J) and DsRed (FIGS. 18C, G, K) and merged signal (FIGS. 18D, H, L) are shown. Autofluorescence was evaluated at ex 488 nm and em at more than 650 nm, EGFP was evaluated at ex 488 nm and em between 505-530 nm, DsRed2 was evaluated at ex 545 nm and em between 585-615 nm.

FIGS. 19A-J are pictures illustrating co-expression of DsRed and GFP in different plants using pTRV2 constructed with the two reporter genes in tandem driven by separate double subgenomic promoters. Plants (*N. tobaccum* and *N. benthamiana*) were inoculated with pTRV1 and pTRV2-Δ2b-sgP-GFP-sgP-DsRed. Fluorescence was evaluated using confocal laser scanning microscopy. The cells' chlorophyll autofluorescence (FIGS. 19A, E), GFP (FIGS. 19B, F) and DsRed (FIGS. 19C, G) are shown. FIG. 19D depicts an image in bright field (for *N. tobaccum*) and FIG. 19H depicts an image of merged signal (for *N. benthamiana*). FIGS. 19I-J are images, taken by stereomicroscope, of inoculated *N. benthamiana* tissues (3 dpi). Autofluorescence ex was evaluated at 488 nm and em at more than 650 nm, GFP was evaluated at ex 488 nm and em between 505-530 nm, DsRed2 was evaluated at ex 545 nm and em between 585-615 nm.

Figure 20:
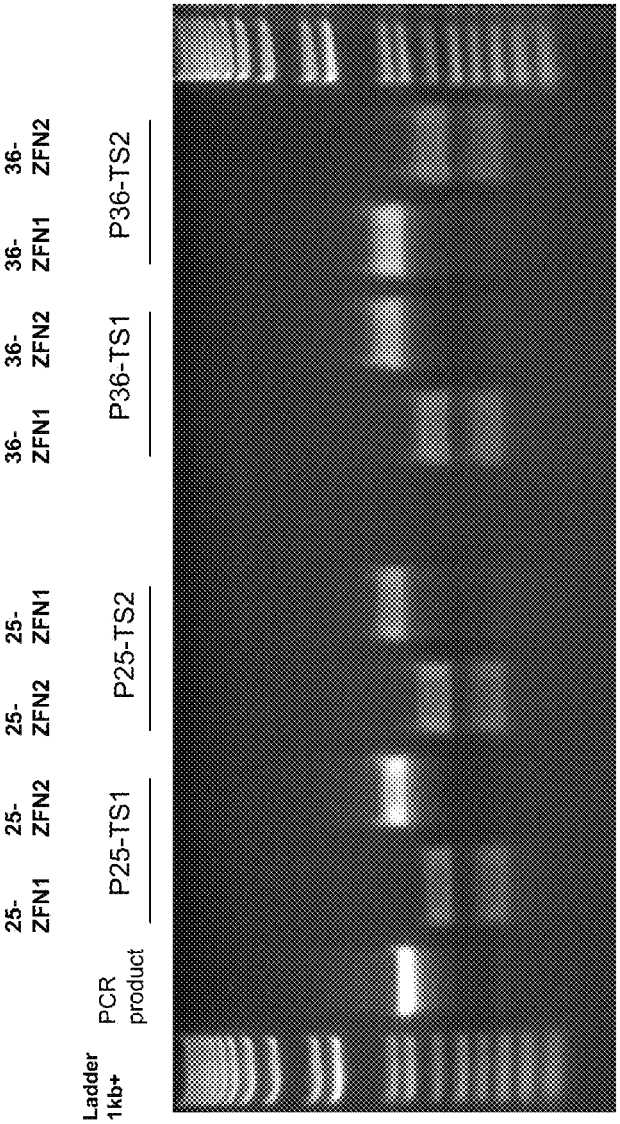

FIG. 20 is a picture illustrating digestion of PCR fragments carrying artificial target sites P1-25-1, P1-25-2, P1-36-1 and P1-36-2 (P25-TS1, P25-TS2, P36-TS1, P36-TS2 respectively) by specific ZFNs. PCR fragments (ca. 900 bp) carrying palindrome-like target sequences were incubated with 25-ZFN-1,25-ZFN-2 or 36-ZFN-1,36-ZFN-2 and the digestion products were separated by agarose gel. Of note, the TS (target site) is palindrome-like.

Figure 21:
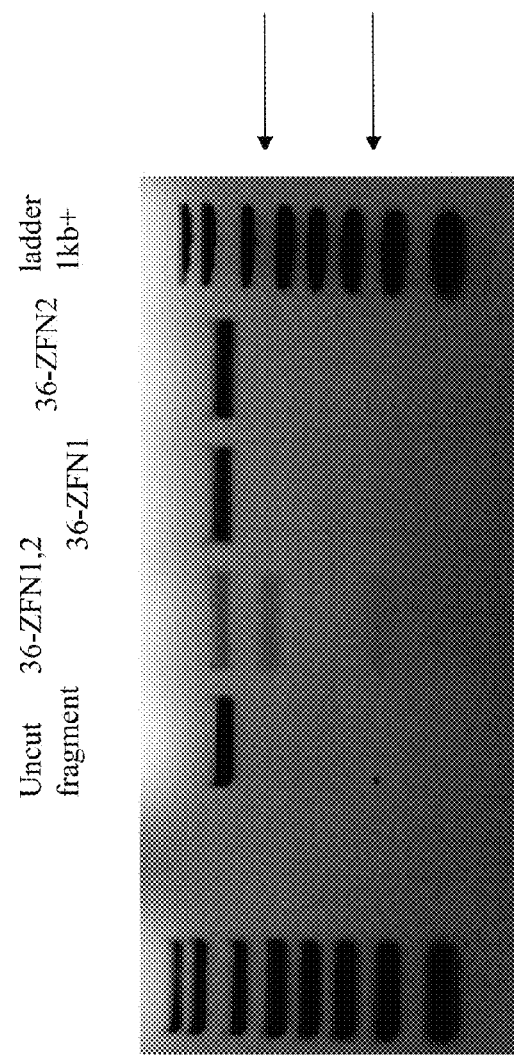

FIG. 21 is a picture illustrating digestion of a NcoI/BamHI (740 bp) fragment from pBS-PI-36, carrying a target P1-36 sequence, with 36-ZFN1 and 36-ZFN2.

Figure 22:
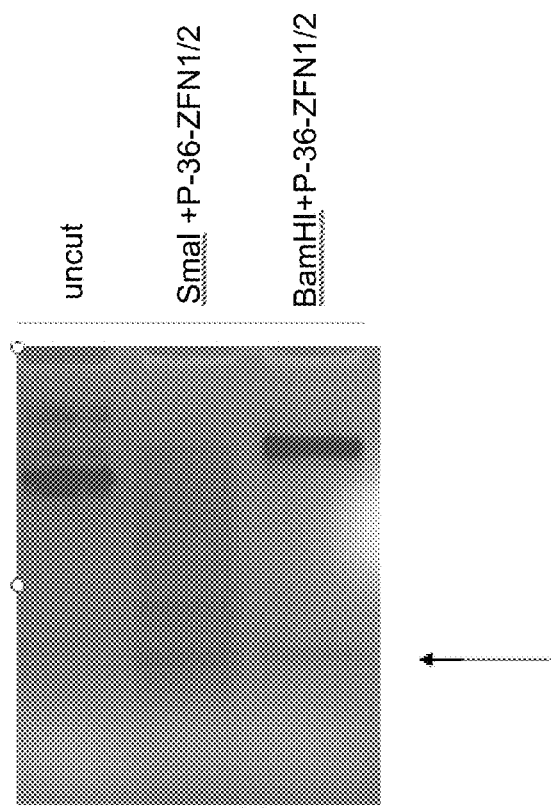

FIG. 22 is a picture illustrating digestion of plasmid pBS carrying PI-36 (pBS-PI-36) by a mixture of ZFNs (36-ZFN 1 and 2). Fragment of expected size (515 bp) is indicated by arrow.

Figure 23:
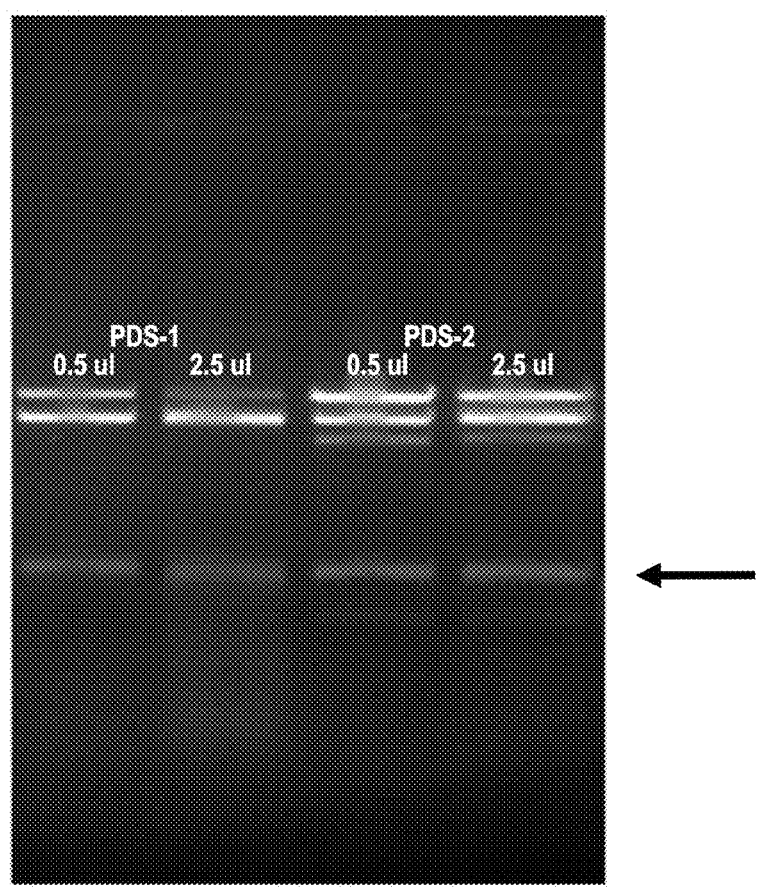

FIG. 23 is a picture illustrating digestion of a plasmid carrying target PDS1 or PDS2 palindromic sites. The tested palindromic sites were cut with specific ZFNs (PDS-ZFN1 and PDS-ZFN2) and AgeI which yielded a fragment of approximately 950 bp, as expected. Volumes listed above the columns refer to the amount of enzyme containing crude extract used. Of note, the TS (target site) is palindrome-like.

FIGS. 24A-B are pictures illustrating the expression of DsRFP (FIG. 24B) and GFP (FIG. 24A) in *petunia* plants inoculated with pTRV2-Δ2b-sgP-CP-PEBV carrying DsRFP and GFP separated by T2A. Figures depict leaf tissues from *petunia* plants 10 days after stem inoculation with the vector.

FIGS. 25A-B show the N termini of the mutated uidA gene sequence. FIG. 25A depicts the uidA gene sequence containing insert of target sites of QEQ-ZFN (bold) and spacer with stop codon (red). FIG. 25B depicts how miss-repair of the double strand breaks formed by the QEQ-ZFN may lead to elimination of the stop codon and reconstruction of the uidA gene.

FIGS. 26A-J are pictures illustrating TRV-based repair of uidA in planta. Transgenic *petunia* and tobacco plants carrying mutated uidA were inoculated in vitro or in vivo with pTRV1 and pTRV2-Δ2b-sgP-QEQ-ZFN. At different times after agroinfiltration or inoculation with virions, GUS activity was evaluated in various parts of the plant including in tissues that developed after inoculation. FIG. 26A depicts a mutated uidA transgenic *Petunia hybrida* line 65 evaluated for GUS expression 12 days post in-vitro agroinoculation. FIG. 26B depicts a mutated uidA transgenic *Nicotiana tobaccum* line 3 evaluated for GUS expression 22 days post in-vitro agroinoculation. FIG. 26C depicts a mutated uidA transgenic *Petunia hybrida* line I evaluated for GUS expression 11 days post in-vitro agroinoculation. FIG. 26D depicts a mutated uidA transgenic *Nicotiana tobaccum* line 3 evaluated for GUS expression 50 days post inoculation. FIG. 26E depicts a mutated uidA transgenic *Petunia hybrida* line N evaluated for GUS expression 17 days post in-vitro agroinoculation. FIG. 26F depicts a mutated uidA transgenic *Petunia hybrida* line I in-vitro inoculation with virions evaluated for GUS expression was carried out 15 days post inoculation. FIG. 26G depicts a mutated uidA transgenic *Petunia hybrida* line I in-vitro agroinoculation with 0.08 OD, evaluated 29 days post inoculation. FIG. 26H depicts a mutated uidA transgenic *Petunia hybrida* line I in-vitro agro inoculation with 0.8 OD, evaluated 29 days post inoculation. FIG. 26I depicts a mutated uidA transgenic *Nicotiana tobaccum* line 11, not treated with TRV, GUS tested, and FIG. 26J depicts a mutated uidA transgenic *Petunia hybrida* line I primordia regeneration evaluated for GUS expression, following in-vitro agroinoculation.

FIG. 27 shows alignment of 20 mutant sequences (SEQ ID NOs: 96-116) in mutated uidA (GUS) identified by DdeI site disruption in the GUS stop codon of transgenic *N. tabacum* CV Samsung (N_t) as well as *Petunia hybrida* (Pet) plants. Of note, the results depicted insertions (1 or 2 nucleotides) and deletions (less or equal to 49 nucleotides). Restoration of GUS activity can be ascribed to mutation in Pet30.

FIG. 28A shows the sequence of phytoene desaturase (PDS) exon from *Petunia hybrida* RB (GenBank accession no AY593974.1, SEQ ID NO: 131). This sequence was confirmed by resequencing (indicated by upper case letters). The highlighted sequences are the target sites (PDS-ZFN1 target site—SEQ ID NO 140 and PDS-ZFN2 target site—SEQ ID NO: 141) of the PDS-ZFNs (SEQ ID NOs: 71 and 73) generated by the present invention (SEQ ID NOs: 70 and 72). SEQ ID NO: 132 depicts a short fragment of a sequence of the complementary strand to which PDS-ZFN2 binds. Recognition site for the MfeI is underlined.

FIG. 28B shows the changes in the PDS nucleic acid sequences (SEQ ID NOs: 119-128) in *Petunia hybrida* plants inoculated with pTRV1 and pTRV2-Δ2b-sgP-PDS-ZFN1-T2A-PDS-ZFN2 vectors. The mutants were compared to the native PDS sequences in the tested *Petunia hybrida* plants (PDS-WT, Y10 and G35). TS1 (GGAGAT-GCA, SEQ ID NO: 135) and TS2 (CACTTCAAT, SEQ ID NO: 136) indicate the binding sites for ZFNs in the PDS gene. The MfeI site (CAATTG, SEQ ID NO: 137) served as a selection tool to isolate ZFNs mediated PDS mutants.

FIG. 29 shows the sequence of flavanone 3 beta-hydroxylase (FHT) exon from *Petunia hybrida* cv. RB (GenBank accession no AF022142.1, SEQ ID NO: 133). The sequence was confirmed by resequencing. The highlighted sequences (FHT-ZFN1 target site—SEQ ID NO 142 and FHT-ZFN2 target site—SEQ ID NO: 143) were used as the target sites for the FHT-ZFNs generated by the present invention (SEQ ID NOs: 74 and 76). Recognition site for the EcoNI is underlined. SEQ ID NO: 134 depicts a short fragment of a sequence of the complementary strand to which FHT-ZFN2 binds.

Figure 30:
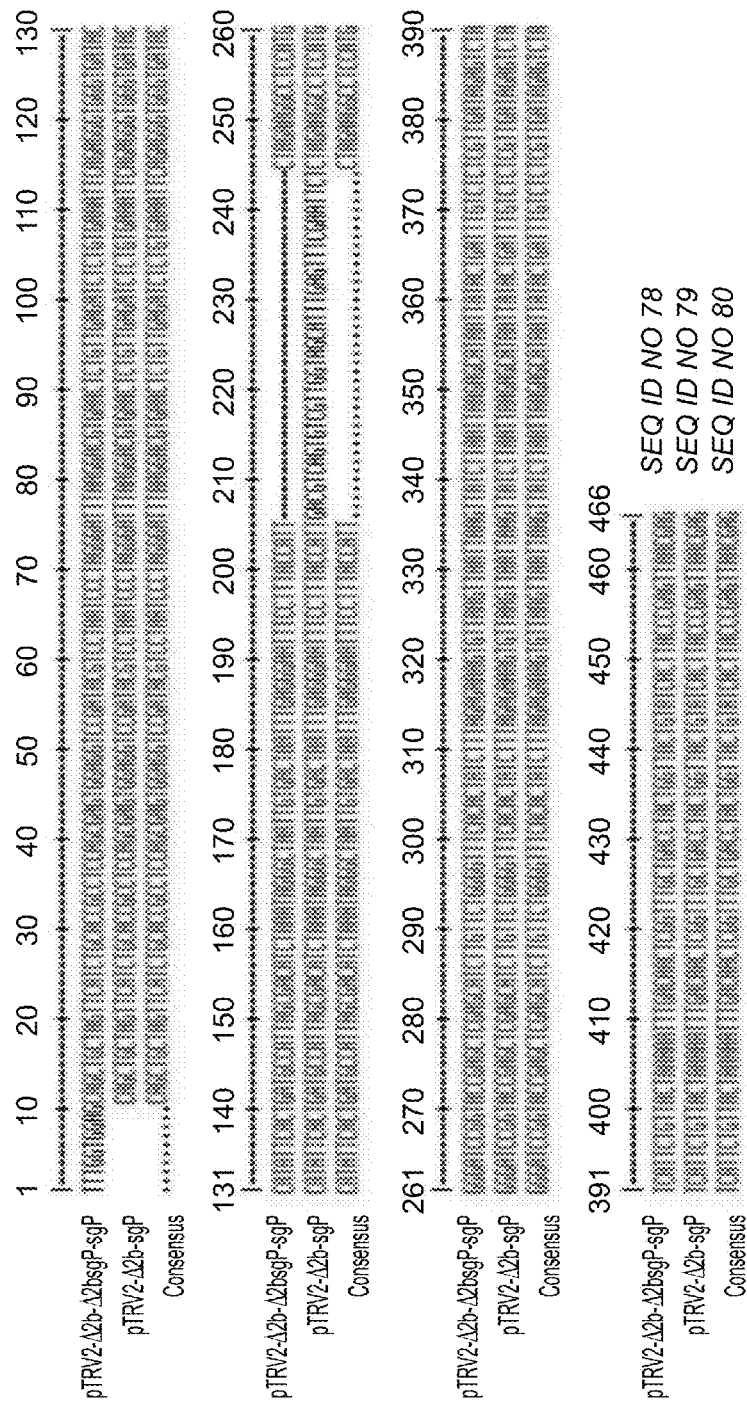

FIG. 30 shows the sequence of pTRV2 containing 2b and PEBV-CP subgenomic promoters (sgP) region (SEQ ID NO: 79). For comparison, the sequence lacking 40 nucleotides from 2b-sgP (pTRV2-Δ2b-Δ2bsgP-sgP) is shown in the upper line (SEQ ID NO: 78). Nucleotides 1 to 72—3' of CP gene, nucleotides 73 to 237—sgP of 2b, nucleotides 238 to 282—MCS, nucleotides 283 to 466—sgP of CP from PEBV. Nucleotides 206 to 237—deletion from the 3' of the 2b sgP.

FIG. 31A shows the sequence of NLS-PDS-ZFN1 (SEQ ID NO 70). The sequence is of the full chimera: NLS, ZFN and FokI (d-domain). Sequences of nuclear localization signal (NLS) are depicted in lower case; nuclease (FokI-domain d) first codon and the termination codon are depicted in bold.

FIG. 31B shows the sequence of NLS-PDS-ZFN2 (SEQ ID NO 72). The sequence is of the full chimera: NLS, ZFN and FokI (d-domain). Sequences of nuclear localization signal (NLS) are depicted in lower case; nuclease (FokI-domain d) first codon and the termination codon are depicted in bold.

FIG. 32A shows the sequence of NLS-FHT-ZFN1 (SEQ ID NO 74). The sequence is of the full chimera: NLS, ZFN and FokI (d-domain). Sequences of nuclear localization signal (NLS) are depicted in lower case; nuclease (FokI-domain d) first codon and the termination codon are depicted in bold.

FIG. 32B shows the sequence of NLS-FHT-ZFN2 (SEQ ID NO 76). The sequence is of the full chimera: NLS, ZFN and FokI (d-domain). Sequences of nuclear localization signal (NLS) are depicted in lower case; nuclease (FokI-domain d) first codon and the termination codon are depicted in bold.

Figure 33:
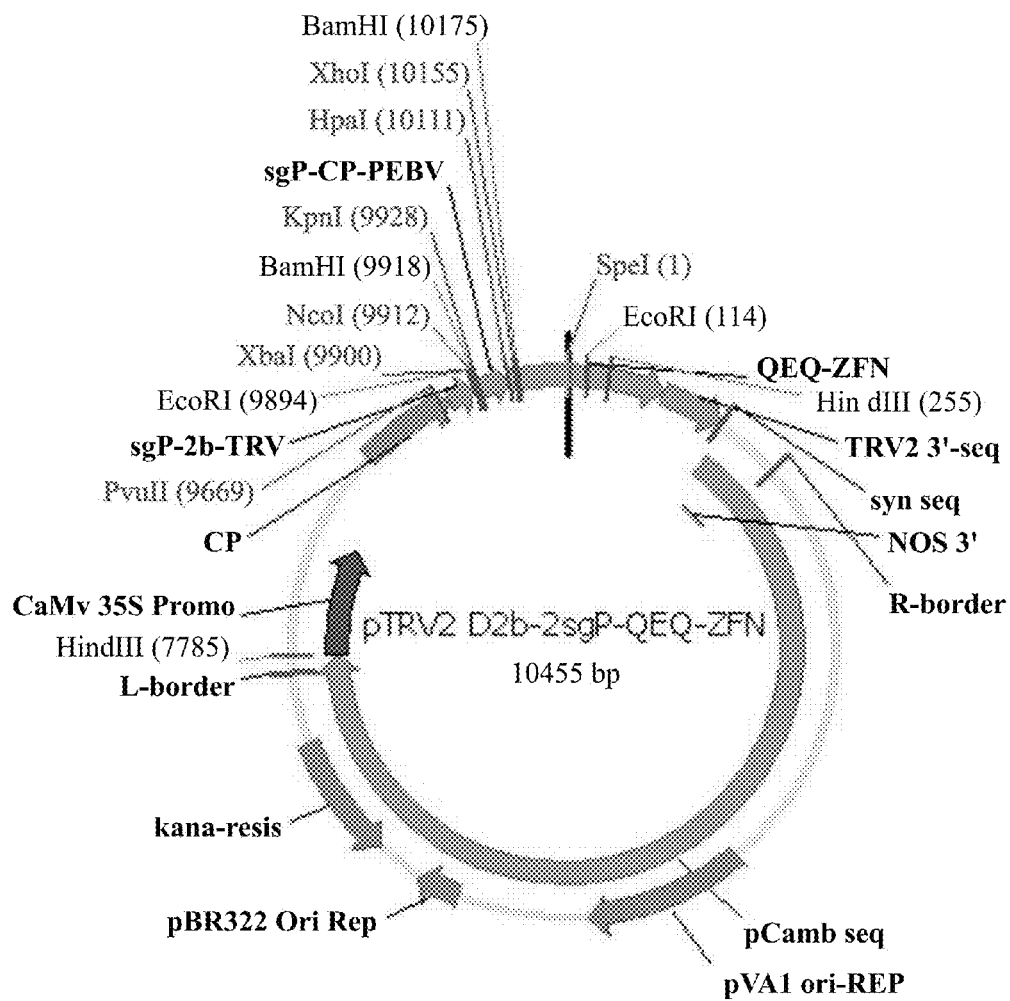

FIG. 33 shows a schematic representation of pTRV2-Δ2b-sgP-QEQ-ZFN (SEQ ID NO: 82).

Figure 34:
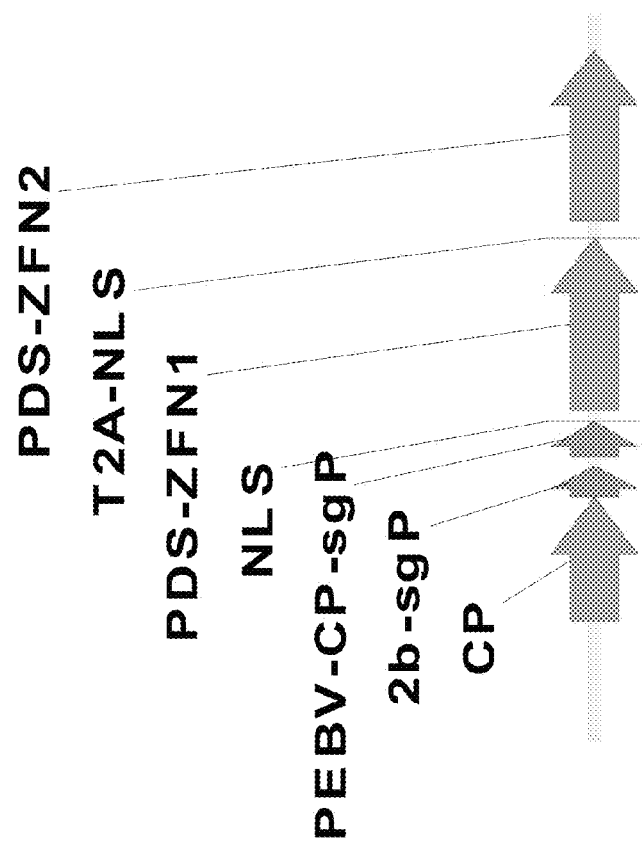
Figures 35A, 35B:
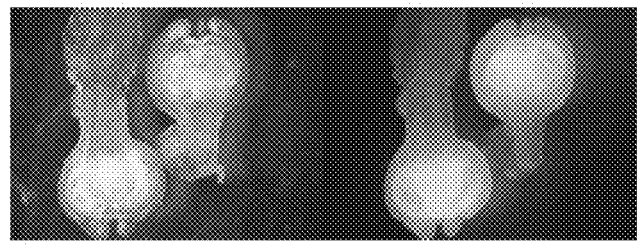
Figures 35C, 35D:
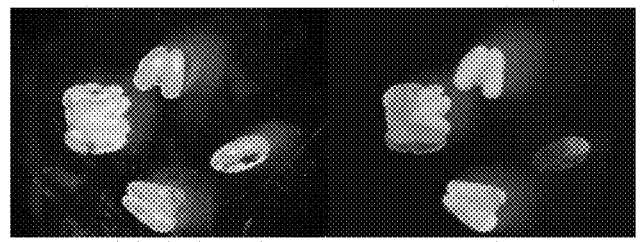
Figures 35E, 35F:
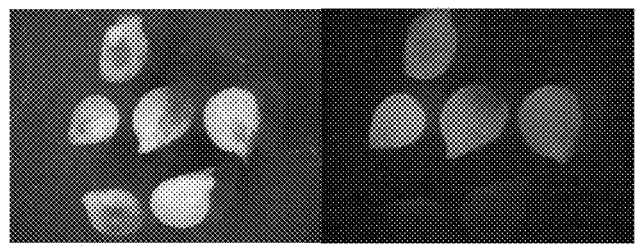
Figures 35G, 35H, 35I, 35J:
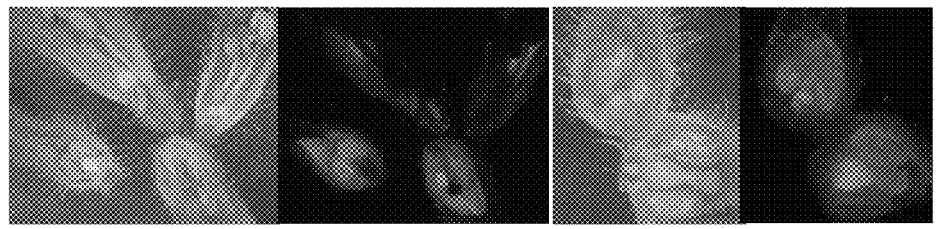
Figures 36A, 36B, 36C:
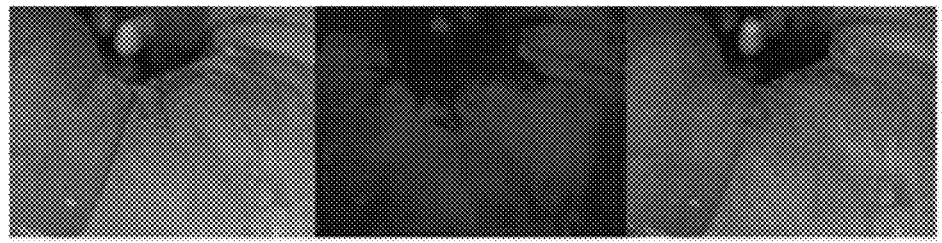
Figures 36D, 36E, 36F:
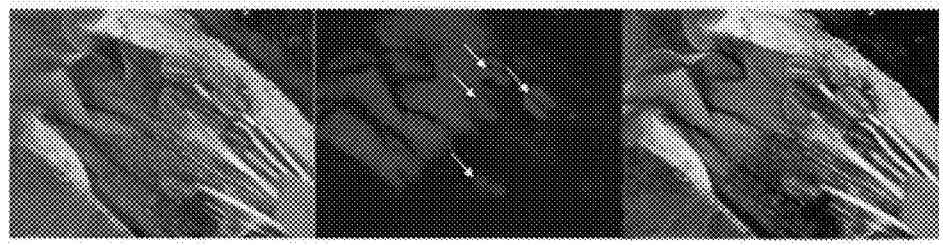
Figures 36G, 36H:
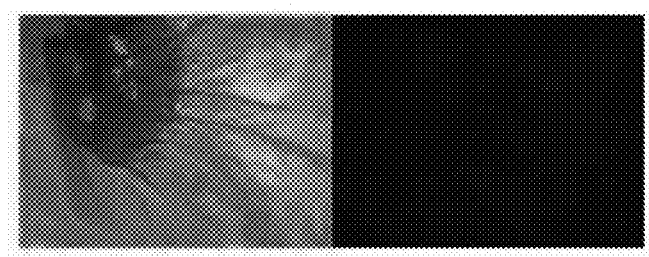

FIG. 34 shows a schematic representation of part of the pTRV2 vector carrying a gene-specific ZFNs (PDS is shown for illustration) fused through T2A sequence, downstream to two subgenomic (2b-sgP and PEBV-CP-sgP) promoters.

FIGS. 35A-J are pictures illustrating expression of DsRed in different floral organs following infection with pTRV1 and pTRV2-Δ2b-sgP-DsRed. *Capsicum annuum* (A-F) and *Petunia hybrida* (G-J) plants that were vacuum infiltrated, express DsRed (35B, D, F, H & J) in the flower organs and seeds 21-45 dpi, as a result of systemic infection. A, B and J, H and I, G show longitudinal section of young buds with anther and ovules; E, F show seeds. A, C, E, G and I show bright field micrographs.

FIGS. 36A-H are pictures illustrating expression of DsRed in *Petunia* flowers infected with pTRV1 and pTRV2-Δ2b-sgP-DsRed. A & D Bright field micrographs infiltrated *Petunia hybrida* flowers. DsRed accumulation in petals and anther (B & E) 3-5 dpi. C & F show merging of A with B and D with E, respectively. G & H are images of control, non infected flowers, at bright field and DsRed filter, respectively.

Figure 37A:
Figure 37B:
Figure 37C:
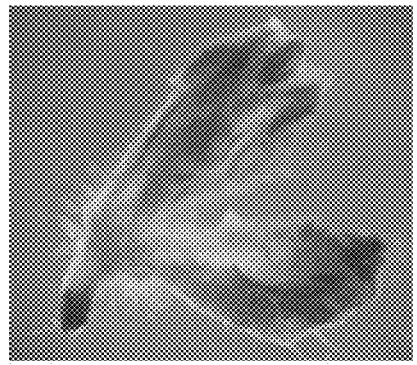

FIGS. 37A-C are pictures illustrating reactivation of GUS in flowers of transgenic *A. thaliana* following viral mediated transient delivery of QEQ-ZFN.

FIGS. 37A-B are two GUS-expressing inflorescences which originated from the experiment depicted in Example 14 (see further details in the Examples section which follows); and FIG. 37C is an enlarged section of FIG. 37B.

Figures 38A, 38B:
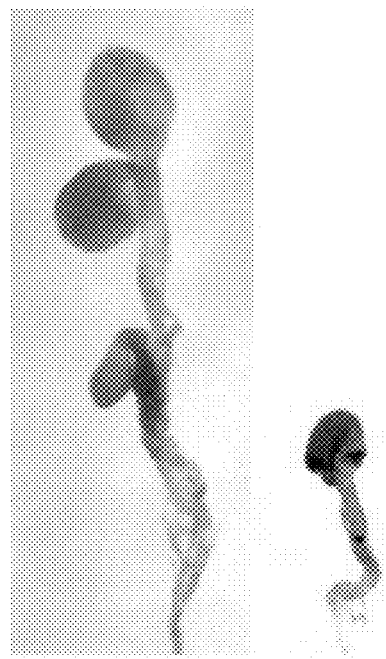

FIGS. 38A-B are pictures illustrating β-glucuronidase-expressing seedlings decending from GUS-reactivated transgenic *A. Thaliana*.

DESCRIPTION OF SPECIFIC EMBODIMENTS OF THE INVENTION

The present invention, in some embodiments thereof, relates to plant viral expression vectors and, more particularly, but not exclusively, to the use of same for generating genotypic variations in plant genomes.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing some embodiments of the present invention to practice, the present inventors have devised an effective tool for generating genotypic variation in plants using viral vectors encoding chimeric polypeptides designed for generating sequence specific double-strand breaks in the plant's genome. As noted in the background section, the formation of DSBs can be used for passively (by plants' repair system) or actively (i.e., directed insertion of heterologous nucleic acid sequences) generating genotypic variation. The aforementioned substantiates beyond any doubt the value of the present tools in generating genomic variations.

As is illustrated in the Examples section which follows, the present inventors have constructed modified tobacco rattle virus (TRV) expression vectors. These vectors were successfully used for introducing and expressing foreign genes of sizes equivalent to the chimeric genes of the present invention (e.g. GUS) in meristematic tissues of different plants (e.g. *Petunia, N. benthamiana* and *N. Tobaccum*, e.g. FIGS. 8A-G, FIGS. 9A-B and FIGS. 11A-F). The present inventors were successful in expressing heterologous genes in chloroplast and mitochondrial plastids (FIGS. 15A-G and FIGS. 16A-K, respectively). Moreover, the present inventors were successful in in-planta co-expression of two heterologous genes (e.g. DsRed and GFP) and specifically in different plant compartments (e.g. cytosol, chloroplasts or nucleus) using viral vectors of some embodiments of the invention (see e.g. FIGS. 17A-D and 18A-L). Importantly, the present inventors have generated zinc finger nucleases (ZFNs) which specifically bind and cleave *petunia* non-coding target sequences (FIGS. 20-22), *petunia* phytoene desaturase (PDS) genomic sequences (FIGS. 23 and 28B) or *petunia* flavanone 3 beta-hydroxylase (FHT) genomic sequences. Moreover, the present inventors expressed heterologous genes (e.g. DsRed) in flower organs (including gametes) and seeds of different plants (e.g. *Capsicum annuum* and *Petunia hybrida*, FIGS. 35A-J and 36A-H). Importantly, the present inventors were successful in reactivation of GUS in flower organs and seedlings descending from GUS-reactivated transgenic plants (e.g. *A. thaliana*) following viral mediated transient delivery ZFNs (FIGS. 37A-C and 38A-B). Accordingly, these chimeric nucleases and viral vectors may serve as powerful tools in the field of agriculture transgenic technologies.

Thus, according to one aspect of the present invention there is provided a method of generating genotypic variation in a genome of a plant. The method comprising introducing into a gamete or a gamete producing tissue of the plant at least one viral expression vector encoding at least one chimeric nuclease which comprises a DNA binding domain, a nuclease and a nuclear localization signal, wherein the DNA binding domain mediates specific targeting of the nuclease to the genome of the plant, thereby generating genotypic variation in the genome of the plant.

As used herein the term "plant" refers to whole plants, portions thereof (e.g., leaf, root, fruit, seed) or cells isolated therefrom (homogeneous or heterogeneous populations of cells). According to an embodiment of the present invention, the plant may be an adult plant such as one which comprises a gamete or a gamete producing tissue.

As used herein the term "gamete" refers to both male and female reproductive plant organs including the anther and ovary (i.e. organs producing pollen and ovules, respectively).

As used herein the phrase "gamete producing tissue" refers to any tissue which may give rise to gametes, such as but not limited to, a floral meristem tissue and flowers.

As used herein the phrase "isolated plant cells" refers to plant cells which are derived from disintegrated plant cell tissue or plant cell cultures.

As used herein the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this aspect of the present invention may comprise a particular type of a plant cell or a plurality of different types of plant cells. It should be noted that optionally plant cultures featuring a particular type of plant cell may be originally derived from a plurality of different types of such plant cells.

Any commercially or scientifically valuable plant is envisaged in accordance with these embodiments of the invention. A suitable plant for use with the method of the invention can be any monocotyledonous or dicotyledonous plant including, but not limited to, maize, wheat, barely, rye, oat, rice, soybean, peanut, pea, lentil and alfalfa, cotton, rapeseed, canola, pepper, sunflower, potato, tobacco, tomato, lettuce, mums, *arabidopsis*, broccoli, cabbage, beet, quinoa, spinach, cucumber, squash, watermelon, beans, hibiscus, okra, apple, rose, strawberry, chile, garlic, onions, sorghum, eggplant, eucalyptus, pine, a tree, an ornamental plant, a perennial grass and a forage crop, coniferous plants, moss, algae, as well as other plants listed in World Wide Web (dot) nationmaster (dot) com/encyclopedia/Plantae.

Accordingly, plant families may comprise Alliaceae, Amaranthaceae, Amaryllidaceae, Apocynaceae, Asteraceae, Boraginaceae, Brassicaceae, Campanulaceae, Caryophyllaceae, Chenopodiaceae, Compositae, Cruciferae, Cucurbitaceae, Euphorbiaceae, Fabaceae, Gramineae, Hyacinthaceae, Labiatae, Leguminosae-Papilionoideae, Liliaceae, Linaceae, Malvaceae, Phytolaccaceae, Poaceae, Pinaceae, Rosaceae, Scrophulariaceae, Solanaceae, Tropaeolaceae, Umbelliferae and Violaceae.

Such plants include, but are not limited to, *Allium cepa, Amaranthus caudatus, Amaranthus retroflexus, Antirrhinum majus, Arabidopsis thaliana, Arachis hypogaea, Artemisia sp., Avena sativa, Bellis perennis, Beta vulgaris, Brassica campestris, Brassica campestris* ssp. *Napus, Brassica campestris* ssp. *Pekinensis, Brassica juncea, Calendula officinalis, Capsella bursa-pastoris, Capsicum annuum, Catharanthus roseus, Chemanthus cheiri, Chenopodium album, Chenopodium amaranticolor, Chenopodium foetidum, Chenopodium quinoa, Coriandrum sativum, Cucumis melo, Cucumis sativus, Glycine max, Gomphrena globosa, Gossypium hirsutum* cv. Siv'on, *Gypsophila elegans, Helianthus annuus, Hyacinthus, Hyoscyamus niger, Lactuca sativa, Lathyrus odoratus, Linum usitatissimum, Lobelia erinus, Lupinus mutabilis, Lycopersicon esculentum, Lycopersicon*

*pimpinellifolium, Melilotus albus, Momordica balsamina, Myosotis sylvatica, Narcissus pseudonarcissus, Nicandra physalodes, Nicotiana benthamiana, Nicotiana clevelandii, Nicotiana glutinosa, Nicotiana rustica, Nicotiana sylvestris, Nicotiana tabacum, Nicotiana edwardsonii, Ocimum basilicum, Petunia hybrida, Phaseolus vulgaris, Phytolacca Americana, Pisum sativum, Raphanus sativus, Ricinus communis, Rosa sericea, Salvia splendens, Senecio vulgaris, Solanum lycopersicum, Solanum melongena, Solanum nigrum, Solanum tuberosum, Solanum pimpinellifolium, Spinacia oleracea, Stellaria media, Sweet Wormwood, Trifolium pratense, Trifolium repens, Tropaeolum majus, Tulipa, Vicia faba, Vicia villosa* and *Viola arvensis*. Other plants that may be infected include *Zea maize, Hordeum vulgare, Triticum aestivum, Oryza sativa* and *Oryza glaberrima*.

According to a specific embodiment of the present invention, the plant comprises a *Petunia hybrida*.

According to another specific embodiment of the present invention, the plant comprises a *Nicotiana tabacum*.

As used herein the phrase "genotypic variation" refers to a process in which a nucleotide or a nucleotide sequence (at least 2 nucleotides) is selectively altered or mutated at a predetermined genomic site, also termed as mutagenesis. The genomic site may be coding or non-coding (e.g., promoter, terminator, splice site, polyA) genomic site. This alteration can be a result of a deletion of nucleic acid(s), a randomized insertion of nucleic acid(s), introduction of a heterologous nucleic acid carrying a desired sequence, or homologous recombination following formation of a DNA double-stranded break (DSB) in the target gene. Genotypic variation according to the present teachings may be transient as explained in further detail hereinbelow. Genotypic variation in accordance with the present teachings is typically effected by the formation of DSBs, though the present invention also contemplates variation of a single strand. Genotypic variation may be associated with phenotypic variation. The sequence specific or site directed nature of the present teachings thus may be used to specifically design phenotypic variation.

As mentioned hereinabove, the method according to this aspect of the present invention is effected by introducing into the plant (e.g. into a gamete or a gamete producing tissue) at least one viral expression vector encoding at least one chimeric nuclease which comprises a DNA binding domain, a nuclease and a nuclear localization signal.

As used herein the phrase "chimeric nuclease" refers to a synthetic chimeric polypeptide which forms a single open reading frame and mediates DNA cleavage in a sequence specific manner.

As used herein the phrase "DNA binding domain" refers to a native or synthetic amino acid sequence such as of a protein motif that binds to double- or single-stranded DNA with affinity to a specific sequence or set thereof (i.e. target site).

In generating chimeric nucleases any DNA binding domain that recognizes the desired DNA binding sequence with sufficient specificity may be employed.

Examples of DNA binding domains include, but are not limited to, helix-turn-helix (pfam 01381), leucine zipper (ZIP) domain, winged helix (WH) domain, winged helix turn helix domain (wHTH), helix-loop-helix and zinc finger domain.

Thus, a variety of such DNA binding domains are known in the art. In an exemplary embodiment of the present invention, the DNA binding domain is a zinc finger binding domain (e.g., pfam00096).

The zinc finger domain is 30 amino acids long and consists of a recognition helix and a 2-strand beta-sheet. The domain also contains four regularly spaced ligands for Zinc (either histidines or cysteines). The Zn ion stabilizes the 3D structure of the domain. Each finger contains one Zn ion and recognizes a specific triplet of DNA basepairs.

Zinc finger domains can be engineered to bind to a predetermined nucleotide sequence. Each individual zinc finger (e.g. Cys2/His2) contacts primarily three consecutive base pairs of DNA in a modular fashion [Pavletich et al., Science (1991) 252:809-817; Berg et al., Science (1996) 271:1081-1085]. By manipulating the number of zinc fingers and the nature of critical amino acid residues that contact DNA directly, DNA binding domains with novel specificities can be evolved and selected [see, e.g., Desjarlais et al., Proc. Natl. Acad. Sci. USA (1992) 89:7345-7349; Rebar et al., Science (1994) 263:671-673; Greisman et al., Science (1997) 275:657-661; Segal et al., Proc. Natl. Acad. Sci. USA (1999) 96:2758-2763]. Hence, a very wide range of DNA sequences can serve as specific recognition targets for zinc finger proteins. Chimeric nucleases with several different specificities based on zinc finger recognition have been previously disclosed [see for example, Huang et al., J. Protein Chem. (1996) 15:481-489; Kim et al., Biol. Chem. (1998) 379:489-495].

Various methods for designing chimeric nucleases with varied DNA binding domains are known in the art. In one embodiment the DNA binding domain comprises at least one, at least two, at least 3, at least 4, at least 5 at least 6 zinc finger domains, binding a 3, 6, 9, 12, 15, or 18 nucleotide sequence, respectively. It will be appreciated by the skilled artisan that the longer the recognition sequence is, the higher the specificity that will be obtained.

Specific DNA binding zinc fingers can be selected by using polypeptide display libraries. The target site is used with the polypeptide display library in an affinity selection step to select variant zinc fingers that bind to the target site. Typically, constant zinc fingers and zinc fingers to be randomized are made from any suitable C2H2 zinc fingers protein, such as SP-1, SP-1C, TFIIIA, GLI, Tramtrack, YY1, or ZIF268 [see, e.g., Jacobs, EMBO J. 11:4507 (1992); Desjarlais & Berg, Proc. Natl. Acad. Sci. U.S.A. 90:2256-2260 (1993)]. The polypeptide display library encoding variants of a zinc finger protein comprising the randomized zinc finger, one or more variants of which will be selected, and, depending on the selection step, one or two constant zinc fingers, is constructed according to the methods known to those in the art. Optionally, the library contains restriction sites designed for ease of removing constant zinc fingers, and for adding in randomized zinc fingers Zinc fingers are randomized, e.g., by using degenerate oligonucleotides, mutagenic cassettes, or error prone PCR. See, for example, U.S. Pat. Nos. 6,326,166, 6,410,248, and 6479626.

Zinc fingers can also be selected by design. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

As illustrated in Example 1 hereinbelow, two sets of chimeric nucleases were designed according to the present teachings each set capable of forming DSBs in specific target sequences of *Petunia* DNA. Initially, DNA binding sequences were identified in *Petunia* plants which were suitable for recognition and cleavage by chimeric nucleases. These DNA binding sequences were non-coding, non-repetitive sequences: P25-TS1 (SEQ ID NO: 10), P25-TS2 (SEQ ID NO: 11), P36-TS1 (SEQ ID NO: 12) and P36-TS2 (SEQ ID NO: 13). Next, chimeric nucleases were designed each comprising 3 zinc fingers. As illustrated in FIGS. 21-22, these zinc fingers designated P1-25-ZFN1, P1-25-ZFN2, P1-36-ZFN1 and P1-36-ZFN2 (SEQ ID NOs: 35, 36, 37, or 38, respectively) specifically bound and cleaved the above mentioned *Petunia* target sites.

Furthermore, as illustrated in Example 1 hereinbelow, according to the present teachings, chimeric nucleases were designed capable of forming specific DSBs in *Petunia* phytoene desaturase (PDS) genomic sequences or in *Petunia* flavanone 3 beta-hydroxylase (FHT) genomic sequences. Initially, DNA binding sequences for PDS and FHT were identified in *Petunia* plants which were suitable for recognition and cleavage by such chimeric nucleases (see FIGS. 28A and 29, respectively). The DNA binding sequences for PDS specific zinc fingers were identified: PDS-ZFN1 (SEQ ID NO: 140) and PDS-ZFN2 (SEQ ID NO: 141) and the chimeric nucleases were designed (SEQ ID NOs: 71 and 73, respectively) which specifically bound and cleaved the PDS *Petunia* target sites. Likewise, the DNA binding sequences for FHT specific zinc fingers were identified: FHT-ZFN1 (SEQ ID NO: 142) and FHT-ZFN2 (SEQ ID NO: 143) and the chimeric nucleases were designed (SEQ ID NOs: 75 and 77, respectively) which specifically bound and cleaved the FHT *Petunia* target sites.

According to an embodiment of the present invention the zinc finger binding domain comprises a nucleic acid sequence as set forth in SEQ ID NOs. 17, 18, 19, 22, 23, 24, 25, 26, 27, 28, 29 or 30.

Preferably, the chimeric nucleases of this aspect of the present invention comprise separate domains for DNA binding and for DNA cleavage, such that DNA cleavage is sequence specific.

As used herein the phrase "sequence specific" refers to a distinct chromosomal location at which a double stranded break (cleavage) is introduced. Without being bound by theory, it is believed that the formation of DSB induces a cellular repair mechanism which typically leads to highly efficient recombinational events at that locus.

As used herein the term "nuclease" refers to any polypeptide, or complex comprising a polypeptide, that can generate a strand break in genomic DNA (i.e. comprises DNA cleavage activity). Examples of nucleases which may be used in accordance with the present teachings include restriction enzymes, topoisomerases, recombinases, integrases and DNAses.

It will be appreciated that the nuclease utilized by the present invention may comprise any non-specific DNA cleavage domain, for example, a type II restriction endonuclease such as the cleavage domain of the FokI restriction enzyme (GenBank accession number J04623). FokI restriction enzymes which generally have separate DNA cleavage and DNA binding domains are suitable for construction of the chimeric nucleases. Thus, according to an embodiment of this aspect, the chimeric nucleases are chimeric proteins comprising specific zinc finger binding domains and the DNA cleavage domain of the FokI restriction enzyme (also referred to herein as the FokI cleavage domain).

In accordance with embodiments of the present invention the chimeric nuclease is an isolated polynucleotide comprising a nucleic acid sequence as set forth in SEQ ID NO. 31, 32, 33, 34, 70, 72, 74, 76, 84, 86 or 88.

In accordance with embodiments of the present invention the chimeric nuclease is an isolated polypeptide comprising an amino acid sequence as set forth in SEQ ID NO. 35, 36, 37, 38, 71, 73, 75, 77, 85, 87 or 89.

Since certain nucleases (e.g. FokI) function as dimers, in order to create double stranded breaks in the target gene at least two chimeric nuclease must be employed. Thus, according to an exemplary embodiment, the chimeric nucleases of the present invention form dimers (e.g., via binding to both strands of a target sequence). For example, chimeric nucleases can form a homodimer between two identical chimeric nucleases (e.g., via binding to two identical DNA binding sequences within a target sequence). Alternatively, chimeric nucleases can form a heterodimer between two different chimeric nucleases (e.g., via binding to two different DNA binding sequences within a target sequence, see e.g., FIG. 1). Accordingly, two chimeric nucleases may be employed to create a double-stranded break in a target sequence. Consequently, the DNA binding domain of the chimeric nuclease, or two or more conjointly acting chimeric nucleases may bind a DNA sequence.

Examples of nucleases which can be used according to the present teachings include, but are not limited to, restriction enzymes including FokI, SceI, I-CeuI, artificial meganucleases, modified meganucleases, homing nucleases; topoisomerases including DNA gyrase, eukaryotic topoisomerase II, bacterial topoisomerase IV and topoisomerase VI; recombinases including Cre recombinase, Hin recombinase, Rad51/RecA; DNAses including deoxyribonuclease I, deoxyribonuclease II and micrococcal nuclease; and integrases.

The phrase "DNA-containing organelle" refers to a subcellular, membrane-encapsulated structure, present in all plant cells.

DNA containing organelles include, the mitochondrion, the nucleus, the chloroplast, the proplastid, the etioplast, the chromoplast and the leukoplast, and any subcellular structure which includes DNA molecules. Typically, the DNA is endogenous but in some cases may refer to exogenous DNA such as of a plant pathogen such as a virus. In the latter case, for example, the DNA-containing organelle is the cytoplasm, in which case the chimeric nuclease may not comprise any localization signal.

It will be appreciated that generating genotypic variation in plant organelles other than the nucleus is of particular interest according to some embodiments of the present invention, as will be detailed infra. Plant organelles (e.g. chloroplast and mitochondria) contain DNA which is a vital participant in plant biochemical pathways. These organelles have a wide structural and functional diversity. As such, they are able to transcribe and translate the information present in their own genome but are strongly dependent on imported proteins that are encoded in the nuclear genome and translated in the cytoplasm.

For example, the chloroplast performs essential metabolic and biosynthetic functions of global significance, including photosynthesis, carotenoids and amino acid biosynthesis. Carotenoids are integral constituents of plants, they are isoprenoids pigments which are involved in a variety of processes including protection against photooxidative stress (through energy-dissipation of excess light absorbed by the antenna pigments); coloring agents in flowers and fruits to attract pollinators, and precursors for the plant growth hormone abscisic acid and vitamin A [Cunningham and Gantt (1998) Annu Rev Plant Physiol Plant Mol Biol 49:557-583]. The carotenoid pigments are synthesized in the plastids of plants where it is derived from the pathways of isoprenoid biosynthesis (Cunningham and Gantt, supra). Two biosynthetic pathways for isoprenoid biosynthesis are present in plants, the mevalonate pathway found in the cytoplasm and the methylerythritol 4-phosphate (MEP) pathway found only in the plastids. The latter biosynthetic route being strongly linked to photosynthesis [Seemann et al. (2006) *FEBS Lett.* 580: 1547-1552].

Moreover, the aromatic amino acid phenylalanine may be synthesized in chloroplasts from the intermediate prephenate: via arogenate by the activity of prephenate aminotransferase or via phenylpyruvate by the activity of prephenate dehydratase [Jung et al. (1986). Proc. Natl. Acad. Sci. 83: 7231-7235; Rippert et al. (2009) Plant Physiol. 149(3): 1251-1260].

Furthermore, the nitrite reductase and acetolactate synthetase activity of the cell is also located in the plastids. The plastids were found to contain only part of the total glutamine synthetase, aspartate aminotransferase, and triosephosphate dehydrogenase activity in the cell [Miflin B (1974) Plant Physiol. 54(4): 550-555]. The chloroplast is also involved in methionine metabolism in plants, chloroplasts are autonomous for de novo methionine synthesis and can import S-adenosylmethionine from the cytosol [Ravanel et al. (2004). J. Biol. Chem. 279 (21): 22548-22557].

Similarly, the mitochondria comprise key roles in cellular metabolic pathways, catalyzing one or several steps in these pathways (e.g. the synthesis of the vitamins folate and biotin, of the non-vitamin coenzyme lipoate, of the cardiolipin diphosphatidylglycerol. Although the mitochondria lack acetyl-CoA carboxylase, it contains the enzymatic equipment necessary to transform malonate into the two main building units for fatty acid synthesis: malonyl- and acetyl-acyl carrier protein (ACP).

Cytoplasmic male sterility (CMS) in plants, characterized by the suppression of the production of viable pollen and by the non-Mendelian inheritance of this trait, is associated with mitochondrial dysfunction. The genetic determinants for cytoplasmic male sterility reside in the mitochondrial genome. CMS phenotype essentially affects the pollen producing organs due to the high requirement of energy by this tissue. Thus, a mitochondrial dysfunction will dramatically affect pollen production while other plant organs may overcome the consequences of mitochondrial dysfunction.

As used herein the phrase "localization domain" refers to a localization signal which facilitates the transport of the chimeric nucleases to the DNA-containing organelle.

The localization signal can be for example, a nuclear localization signal (NLS), such as a short predominantly basic amino acid sequence, which is recognized by specific receptors at the nuclear pores. In other exemplary embodiments, the localization signal for a DNA containing organelle can be a mitochondrial localization signal (MLS) or a chloroplast localization signal (CLS).

Essentially any NLS may be employed, whether synthetic or a naturally occurring NLS, as long as the NLS is one that is compatible with the target cell (i.e. plant cell).

Although nuclear localization signals are discussed herewith, the present teachings are not meant to be restricted to these localization signals, as any signal directed to a DNA-containing organelle is envisaged by the present teachings. Such signals are well known in the art and can be easily retrieved by the skilled artisan.

Nuclear localization signals which may be used according to the present teachings include, but are not limited to, SV40 large T antigen NLS, acidic M9 domain of hnRNP A1, the sequence KIPIK in yeast transcription repressor Matα2 and the complex signals of U snRNPs, tobacco NLS and rice NLS.

Mitochondrion localization signals which may be used according to the present teachings include, but are not limited to the transition signals of, Beta ATPase subunit [cDNAs encoding the mitochondrial pre-sequences from *Nicotiana* plumbaginifolia β-ATPase (nucleotides 387-666)], Mitochondrial chaperonin CPN-60 [cDNAs encoding the mitochondrial pre-sequences from *Arabidopsis thaliana* CPN-60 (nucleotides 74-186] and COX4 [the first 25 codons of *Saccharomyces cerevisiae* COX4 which encodes the mitochondrial targeting sequence].

According to a specific embodiment of the present invention, the localization signal may comprise a mitochondria localization signal, such as the signal peptide of the ATPase beta subunit (ATP-β) (SEQ ID NO: 139).

Chloroplast localization signals which may be used according to the present teachings include, but are not limited to the transition signals of the ribulose-1,5-bisphosphate carboxylase (Rubisco) small subunit (ats1A) associated transit peptide, the transition signal of LHC II, as well as the N-terminal regions of *A. thaliana* SIG2 and SIG3 ORFs. See also wwwdotspringerlinkdotcom/content/p65013h263617795/.

Alternatively, the chloroplast localization sequence (CLS) may be derived from a viroid [Evans and Pradhan (2004) US 2004/0142476 A1]. The viroid may be an Avsunviroiae viroid, for example, an Avocado Sunblotch Viroid (ASBVd), a Peach Latent Mosaic Virus (PLMVd), a Chrysanthemum Chlorotic Mottle Viroid (CChMVd) or an Eggplant Latent Viroid (ELVd).

According to a specific embodiment of the present invention, the localization signal may comprise a chloroplast localization signal, such as the transit peptide ribulose-1,5-bisphospate carboxylase small subunit (Rssu) (SEQ ID NO: 138).

For efficient gene targeting, the DNA binding domain of the present invention needs to be coupled to the nuclease as to permit DNA cleavage within a workable proximity of the target sequence. A workable proximity is any distance that still facilitates the sequence targeting. Optionally, the DNA binding domain overlaps the target sequence or may bind within the target sequence.

Recombinant DNA technology is typically used to generate the chimeric nucleases of the present invention [see Example 1 of the Examples section which follows and Sambrook et al., Eds., Molecular Cloning: A Laboratory Manual, 2nd edition, Cold Spring Harbor University Press, New York (1989); Ausubel et al., Eds., Current Protocols in Molecular Biology, John Wiley & Sons, New York (1998); and Maeder, et al. (2008) Mol Cell 31:294-301, as well as other references which are provided hereinbelow].

Qualifying chimeric nucleases thus generated for specific target recognition can be effected using methods which are well known in the art.

A method for designing a chimeric nuclease for use in gene targeting may include a process for testing the toxicity of the chimeric nuclease on a cell. Such a process may comprise expressing in the cell, or otherwise introducing into a cell, the chimeric nuclease and assessing cell growth or death rates by comparison against a control. The tendency of a chimeric nuclease to cleave at more than one position in the genome may be evaluated by in vitro cleavage assays, followed by electrophoresis (e.g. pulsed field electrophoresis may be used to resolve very large fragments) and, optionally, probing or Southern blotting (see Example 5 in the Examples section which follows). In view of the present disclosure, one of ordinary skill in the art may devise other tests for cleavage specificity.

In one specific embodiment, the present invention provides two sets of chimeric nucleases: P1-25-ZFN1 and P1-25-ZFN2 (shown in SEQ ID NO: 35 and 36, respectively) for gene targeting at the P1-25 site 1 (SEQ ID NO: 10) and P1-25 site 2 (SEQ ID NO: 11) of *Petunia*, respectively; and P1-36-ZFN1 and P1-36-ZFN2 (shown in SEQ ID NO: 37 and 38, respectively) for gene targeting at the P1-36 site 1 (SEQ ID NO: 12) and P1-36 site 2 (SEQ ID NO: 13) of *Petunia*. In particular, P1-25-ZFN1 and P1-25-ZFN2 can form a dimer and P1-36-ZFN1 and P1-36-ZFN2 can form a dimer for generating specific double stranded breaks in *Petunia* target genes.

In another embodiment of the present invention there is provided a set of PDS chimeric nucleases: PDS-ZFN1 and PDS-ZFN2 (shown in SEQ ID NO: 71 and 73, respectively) for gene targeting at the PDS site 1 (SEQ ID NO: 140) and PDS site 2 (SEQ ID NO: 141) of *Petunia*, respectively. These chimeric nucleases can form a dimer for generating specific double stranded breaks in *Petunia* PDS gene.

In another embodiment of the present invention there is provided a set of FHT chimeric nucleases: FHT-ZFN1 and FHT-ZFN2 (shown in SEQ ID NO: 75 and 77, respectively) for gene targeting at the FHT site 1 (SEQ ID NO: 142) and FHT site 2 (SEQ ID NO: 143) of *Petunia*, respectively. These chimeric nucleases can form a dimer for generating specific double stranded breaks in *Petunia* FHT gene.

As mentioned hereinabove, the chimeric nuclease is introduced into the plant target using a viral expression vector, which is typically used for mediating transient transformation, systemically spreading within the plant such as through the meristem infection or through floral infection.

Thus, according to another aspect of the present invention there is provided a plant viral expression vector comprising a nucleic acid sequence encoding at least one chimeric nuclease which comprises a DNA binding domain, a nuclease and optionally a localization signal.

As used herein a plant viral expression vector refers to a nucleic acid vector including a DNA vector (e.g., a plasmid), a RNA vector, virus or other suitable replicon (e.g., viral vector) encoding for viral genes or parts of viral genes.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Other viruses which may be useful in transformation of plant hosts include tobacco rattle virus (TRV) and its related viruses. TRV is known for its ability to infect meristematic tissues, it comprises a broad host range and different strain isolates. For example strain N5, obtained from narcissus, causes severe necrosis in *Nicotiana clevelandii* [Harrison et al. (1983) Ann. appl. Biol., 102:331-338]. The hypochoeris mosaic virus (HMV), which is serologically related to TRV [Uhde et al. (1998) Archives of Virology 143:1041-1053], infects the Asteraceae family of plants [Brunt and Stace-Smith (1978) Ann. appl. Biol. 90:205-214]. The tobacco rattle virus strain TCM, originally obtained from tulip, is serologically closely related to the Dutch serotype of *Pea early-browning virus* [Robinson et al., J. Gen. Virol. (1987) 68:2551-2561). Furthermore, there are also monocotyledons species susceptible to TRV, as for example *Avena sativa* (family Poaceae) [Cadman and Harrison, Ann. appl. Biol. (1959) 47:542-556].

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by replicating the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931, Dawson, W. O. et al. (1989). A tobacco mosaic virus-hybrid expresses and loses an added gene. Virology 172, 285-292; French, R. et al. (1986) Science 231, 1294-1297; and Takamatsu, N. et al. (1990). Production of enkephalin in tobacco protoplasts using tobacco mosaic virus RNA vector. FEBS Lett 269, 73-76.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of replicating or expressing adjacent genes or nucleic acid sequences in the plant host and incapable of recombination with each other and with native subgenomic promoters. Non-native (foreign, heterologous) nucleic acid sequences may be inserted adjacent the native plant viral subgenomic promoter or the native and a non-native plant viral subgenomic promoters if more than one nucleic acid sequence is included. The non-native nucleic acid sequences are replicated or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of replicating or expressing adjacent genes in a plant host and are incapable of recombination with each other and with native subgenomic promoters. Non-native nucleic acid sequences may be inserted adjacent the non-native subgenomic plant viral promoters such that said sequences are replicated or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein i.e., the chimeric nuclease and optionally other heterologous coding or non-coding nucleic acid sequences.

A viral expression vector comprising a nucleic acid encoding a chimeric nuclease is operably linked to one or more transcriptional regulatory sequences whereby the coding sequence is under the control of transcription signals to permit production or synthesis of the chimeric nuclease. Such transcriptional regulatory sequences include promoter sequences, enhancers, and transcription binding sites.

Promoters which are known or found to cause transcription of a foreign gene in plant cells can be used in the present invention. Such promoters may be obtained from plants or viruses and include, but are not limited to, the 35S promoter of cauliflower mosaic virus (CaMV) (includes variations of CaMV 35S promoter, e.g. promoters derived by means of ligations with operator regions, random or controlled mutagenesis, etc.), promoters of seed storage protein genes such as Zma10 Kz or Zmag12 (maize zein and glutelin genes, respectively), light-inducible genes such as ribulose bisphosphate carboxylase small subunit (rbcS), stress induced genes such as alcohol dehydrogenase (Adh1), or "housekeeping genes" that express in all cells (such as Zmaact, a maize actin gene). For added control, the chimeric nuclease may be under the control of an inducible promoter.

In one embodiment the plant viral expression vector is a tobacco rattle virus (TRV) expression vector.

TRV-based expression vectors have been described in for example U.S. Pat. No. 7,229,829.

TRV is a positive strand RNA virus with a bipartite genome, hence the genome is divided into two positive-sense, single-stranded RNAs, that may be separately encapsidated into viral particles. The two TRV genomic RNA vectors used by the present invention are referred to herein as pTRV1 (GeneBank Accession No: AF406990) and pTRV2 (GeneBank Accession No: AF406991), wherein pTRV1 encodes polypeptides that mediate replication and movement in the host plant while pTRV2 encodes coat proteins.

In certain embodiments, the nucleic acid sequence of pTRV2 is devoid of 2b sequence (SEQ ID NO: 43). Generating a pTRV2 vector devoid of the 300 bp of the RNA2 2b gene was carried out by removal from the original vector by digestion with PvuII and EcoRI (see FIGS. 6A-B). The resultant plasmid (pTRV2Δ2b) was identical to the original pTRV2 but lacking the 2b sequence (see Example 1, hereinbelow). According to the present teachings, pTRV2 vectors without the 2b region are much more efficient in gene expression in meristematic tissues (see Example 2, hereinbelow).

In certain embodiments, modification to pTRV2 vector comprises addition of an enhancer. Any enhancer can be inserted into the viral expression vector to enhance transcription levels of genes. For example, a Ω enhancer (SEQ ID NOs: 44 or 47) can be cloned into the pTRV2 vectors of the present invention.

Alternatively, the viral vector of the present invention may be based on TRV related viruses (e.g. tobacco rattle virus strain N5, HMV, or tobacco rattle virus strain TCM).

The selection of the vector may be dependent on the target plant such as monocots. The modified wheat streak mosaic virus (WSMV) has been previously shown to express NPT II and β-glucuronidase (GUS) in monocots (e.g. wheat, barley, oat and maize) [Choi et al., Plant J. (2000) 23:547-555; Choi et al., J Gen Virol (2002) 83:443-450; Choi et al., J. Gen. Virol. (2005) 86:2605-2614]. The work of Choi et al. demonstrated the placement of the foreign genes between the nuclear inclusion b (NIb) and coat protein (CP). For better expression and activity in infected wheat, GUS was inserted immediately downstream of the P1 cleavage site and up stream to HC-Pro of the wheat streak mosaic virus (WSMV) polyprotein ORF. Systemic infection and GUS expression was demonstrated upon inoculation of plants with WSMV in vitro.

The present invention contemplates a viral expression vector comprising at least two heterologous polypeptide sequences.

As used herein the term "heterologous sequence" refers to a sequence that is not normally part of an RNA2 of a naturally occurring TRV. In certain embodiments, a heterologous sequence is a chimeric nuclease as described in detail hereinabove. In certain embodiments, a heterologous sequence is a sequence of interest, such as a plant gene for expression in a plant cell of a heterologous polypeptide. Such plant genes may include, but are not limited to, genes encoding a reporter polypeptide, an antiviral polypeptide, a viral moiety, an antifungal polypeptide, an antibacterial polypeptide, an insect resistance polypeptide, a herbicide resistance polypeptide, a biotic or abiotic stress tolerance polypeptide, a pharmaceutical polypeptide, a growth inducing polypeptide, and a growth inhibiting polypeptide. In certain embodiments, the viral vector comprises both chimeric nucleases and a sequence of interest.

As part of the pTRV vector, the heterologous sequences may comprise separate sub genomic promoters (sgPs), thus may comprise two separate sgPs (e.g. SEQ ID NO: 45 and SEQ ID NO: 48) for replication of the heterologous sequences.

In certain embodiments, the at least two heterologous polypeptide sequences within the viral vector are separated by nucleic acid sequence encoding a cleavage domain. Such a cleavage domain may comprise any cleavage domain known in the art, as for example a T2A-like protein sequence (SEQ ID NOs: 40 and 52).

It will be appreciated that the nucleic acid sequence of the two heterologous polypeptide sequences separated by a cleavage domain may be as set forth in SEQ ID NOs: 84, 86 or 88.

It will be appreciated that the amino acid sequence of the two heterologous polypeptide sequences separated by a cleavage domain may be as set forth in SEQ ID NOs: 85, 87 or 89.

Generally, when introduced into a host plant cell, a pTRV vector provides expression of the heterologous sequence(s) and may also provide expression of other TRV sequences, such as a viral coat protein.

pTRV vectors of the present invention may express a reporter gene so that transformed cells can be identified. Exemplary reporter genes that may be expressed include, but are not limited to, GUS and GFP.

It will be appreciated that two viral expression vectors may be introduced into the same plant cell. These viral vectors may be introduced in the plant cell concomitantly or at separate times. Such viral expression vectors may comprise the same type of vector encoding different heterologous sequences, or alternatively may comprise two different types of vectors (e.g. BV vector and TRV vector, mitovirus vector and TRV vector, TRV1 and TRV2 vectors). For example, pTRV1 and pTRV2 vectors can be introduced concomitantly, as for example at a 1:1 ratio, to enable expression of viral genes in plant cells. Likewise, one vector may comprise the chimeric nuclease/s and another vector may comprise a heterologous gene of interest (as described in detail hereinabove).

It will be appreciated that in order to introduce the heterologous gene of interest (i.e. foreign DNA) into different DNA containing organelles (e.g. nucleus, chloroplast and mitochondria), different types of vectors may be implemented.

Thus, vectors for delivery of foreign DNA may be based on the Geminivirus *Abutilon* mosaic virus (AbMV), a member of the *Begomovirus* genus. The AbMV viral DNA has been detected in plastids [Gröning et al., (1987) PNAS USA 84: 8996; Gröning et al. (1990) Mol. Gen. Gene. 220: 485; Horns & Jeske, (1991) Virol. 181: 580].

The viral vector of the present invention may also be based on the genus *Mitovirus*, family Narnaviridae such as *H. mompa* mitovirus 1-18 (HmMV1-18) or *O. novo*-ulmi mitovirus 6 (OnuMV6). The HmMV1-18 viral dsRNA has been detected in mitochondria [Osaki et al (2005) Virus res. 107, 39-46; Cole et al (2000) Virol. 268, 239-243].

Other DNA virus based vectors that are envisioned by the present invention include, for example, Geminiviridae, Caulimoviridae and Badnaviridae.

For example, Geminiviridae contain circular covalently closed single-stranded (ss) DNA (~2.8 Kbp) genomes, packaged within twinned (so-called geminate) particles. The sequences regulating DNA replication and transcriptional activity are located in the intergenic regions (IR). The invariant TAATATT_AC sequence is located in the LIR (in mastreviruses), IR (in curtoviruses) and CR (in begomoviruses) and contains the initiation site of rolling-circle DNA replication. The geminivirus replication cycle can be subdivided in several functionally distinct stages. Early during the infection process, viral particles are injected by the insect vector, presumably uncoated, and the viral genome is transported into the host cell nucleus where all later stages occur: conversion of circular ssDNA into covalently closed circular dsDNA intermediates, rolling-circle replication (RCR), production of circular ssDNA genomes for encapsidation [Gutierrez (1999) Cell. Mol. Life. Sci. 56 313-329].

Geminiviruses are divided into four genera on the basis of their genome organizations and biological properties [Fauquet et al (2003) Arch Virol 148: 405-421]. Mastreviruses (e.g. Maize streak virus, Panicum streak virus, Sugarcane streak virus, Sugarcane streak Egypt virus, Sugarcane streak Reunion virus, Digitaria streak virus, etc) have monopartite genomes and are transmitted by leafhopper to monocotyledonous plants. Curtoviruses (e.g. Beet curly top virus) have monopartite genomes distinct from those of the mastreviruses and are transmitted by leafhopper vectors to dicotyledonous plants. Topocuviruses (e.g. Tomato pseudo-curly top virus) have monopartite genomes which are transmitted by a treehopper vector to dicotyledonous plants. Begomoviruses (e.g. Bean golden yellow mosaic virus, Tomato yellow leaf curl virus, *Abutilon* mosaic virus, Tobacco leaf curl virus, African cassava mosaic virus, Mung bean yellow mosaic virus) have bipartite genomes (although numerous begomoviruses with a monopartite genome also occur) and are transmitted by the whitefly *Bemisia tabaci* to dicotyledonous plants.

Caulimovirus particles contain a single molecule of dsDNA (~8 kbp). Caulimoviruses usually infect hosts systemically; they are found in most mesophyll, parenchyma and epidermal cells and sometimes in phloem sieve tubes and tracheids. Members of the genus include e.g. Cauliflower mosaic virus (CaMV), Soybean chlorotic mottle (SoyCMV), Cassava vein mosaic (CVMV), *Petunia* vein clearing (PVCV), Rice tungro bacilliform virus (RTBV).

It will be appreciated that the universal vector IL-60 and auxiliary constructs, which has been recently described [WO 2007/141790] may also be used by the present invention. This vector which is, in fact, a disarmed form of Tomato yellow leaf curl virus (begomovirus), is applied as a double-stranded DNA [Peretz et al (2007) Plant Physiology 145: 1251-1263]. With IL-60 as the disarmed helper "virus", transactivation occurs, resulting in an inducible expression/silencing system.

In order to direct the vectors containing the foreign DNA into specific DNA containing organelles, a nuclear localization signal (NLS), chloroplast localization signal (CLS) or mitochondria localization signal (MLS) may be introduced inframe to the heterologous sequence (as is described in further detail hereinabove).

To achieve transformation of plant cells or the whole plant, the viral expression vectors of the present invention can be introduced into the host cell by any method known in the art. For example, transient transformation can be achieved by *Agrobacterium*-mediated gene transfer, by direct DNA transfer methods, by viral infection (i.e. using the modified plant viruses) or by nematodes, by infiltration, by vacuum, by electroporation or by bombardment.

*Agrobacterium*-mediated gene transfer as disclosed herein (see for example, Example 1 hereinbelow) includes the use of plasmid vectors that contain defined DNA segments. For example, the present invention teaches the use of *Agrobacterium tumefaciens* (strain AGLO and EHA-105) transformed with pTRV1, pTRV2 and pTRV2 derivatives containing plasmids as was previously described [see e.g. Liu et al., Plant J (2002) 30: 415-429]. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation [Horsch, R. B. et al. (1988). "Leaf disc transformation." Plant Molecular Biology Manual A5, 1-9, Kluwer Academic Publishers, Dordrecht]. A supplementary approach employs the *Agrobacterium* delivery system in combination with vacuum infiltration. The *Agrobacterium* system is especially useful for in the creation of transgenic dicotyledenous plants. See: Klee, H. J. et al. (1987). Annu Rev Plant Physiol 38, 467-486; Klee, H. J. and Rogers, S. G. (1989). Cell Culture and Somatic Cell Genetics of Plants, Vol. 6, Molecular Biology of Plant Nuclear Genes, pp. 2-25, J. Schell and L. K. Vasil, eds., Academic Publishers, San Diego, Calif.; and Gatenby, A. A. (1989). Regulation and Expression of Plant Genes in Microorganisms, pp. 93-112, Plant Biotechnology, S. Kung and C. J. Amtzen, eds., Butterworth Publishers, Boston, Mass. The present teachings also disclose *Agrobac-*

*terium*-mediated gene transfer by injection of *Agrobacteria* into the plant (e.g. into the exposed shoot surface following removal of the apical meristems) and by leaf infiltration as for example using a syringe without a needle (e.g. *Agrobacteria* content of the syringe is discharged into the scratched surface of the leaf, see Example 1 of the example section which follows).

Direct DNA transfer methods include for example electroporation, microinjection and microparticle bombardment. See, e.g.: Paszkowski, J. et al. (1989). Cell Culture and Somatic Cell Genetics of Plants, Vol. 6, Molecular Biology of Plant Nuclear Genes, pp. 52-68, J. Schell and L. K. Vasil, eds., Academic Publishers, San Diego, Calif.; and Toriyama, K. et al. (1988). Bio/Technol 6, 1072-1074 (methods for direct uptake of DNA into protoplasts). These methods may further be used to direct the foreign DNA containing vectors (as depicted in detail hereinabove) into specific DNA containing organelles. For example, tobacco protoplasts were electroporated co-transformed with both DNA encoding the nuclease and donor DNA [Wright et al. (2005) Plant J 44:693-705].

Infection of viral vectors (e.g. pTRV) into plants can also be carried out by the use of nematodes, including without limitation, *N. benthamiana* or *N. clevelandii* (the natural host for TRV). Accordingly, *N. benthamiana* or *N. clevelandii* are inoculated with pTRV1, pTRV2 or their derivatives prior to subjection to the plants.

Infection of viral vectors into plants may also be effected by virion infection (as depicted in detail in Example 1, hereinbelow). Virion infection may be carried out, for example, by first inoculating the usual hosts of the virus (e.g. TRV infection of *Petunia*) with the viral vector (pTRV1, pTRV2, or its derivatives). About 5 to 21 days post infection (dpi) plant leaves are collected and the sap is extracted in 20 mM phosphate buffer pH=6.8 and a surfactant (e.g. 0-0.03% Silwet L-77) by mortar and pestle. The TRV containing sap is then dripped onto cheesecloth or centrifuged to remove cells debris and following addition of carborundum fine powder (to improve infection) stems and leaves of young (approximately 1 month old) plants are gently scratched. Sap infection of in-vitro grown plants may also be carried by first passing the sap through 0.22 μm filter and then stems of tissue culture propagated plants are injured and infected using syringe and needle or by vacuum. For seeds infection (e.g. monocotyledon), seeds may be incubated with the sap during swelling and sprouting (for approximately 1 to 2 weeks).

A transgenic whole plant, callus, tissue or plant cell may be identified and isolated by selecting or screening the engineered plant material for traits encoded by the marker genes present on the viral expression vectors. For instance, selection may be performed by growing the engineered plant material on media containing an inhibitory amount of the antibiotic or herbicide to which the transforming gene construct confers resistance. Further, transgenic plants and plant cells may also be identified by screening for the activities of any visible marker genes (e.g., GFP or GUS) that may be present on the viral expression vectors. Such selection and screening methodologies are well known to those skilled in the art.

Physical and biochemical methods may also be employed to identify transgenic plants or plant cells containing inserted gene constructs. These methods include, but are not limited to, Southern analysis or PCR amplification, Northern blot, enzymatic assays, protein gel electrophoresis, Western blot techniques, immunoprecipitation, or enzyme-linked immunoassays. Additional techniques, such as in situ hybridization, enzyme staining, and immunostaining, also may be used to detect the presence or expression of the heterologous genes in specific plant organs and tissues. The methods for doing all these assays are well known to those skilled in the art.

Other references which may be used to implement the teachings of the present invention are provided infra: *Agrobacterium* delivery of a Ti plasmid harboring both the ZFNs and a donor DNA construct [Cai et al. (2009) Plant Mol. Biol. Accepted: 14 Dec. 2008].

It will be appreciated that the viral expression vectors of the present invention may be introduced directly into a gamete or gamete producing tissue, or alternatively may be introduced into the plant by any other method known in the art as, for example, by leaf infiltration or by injection of *Agrobacteria* into the plant (as described in further detail hereinabove). Identification of transformed gametes or gamete tissue may be carried out by identification of visible marker genes (e.g., GFP or GUS) which are specifically expressed in these cells, regardless of expression in other plant tissues (for example, roots, leaf, leaflets, stems). Thus, not all plant tissues need to express the chimeric nucleases of the present invention in order to achieve transformed gametes or gamete tissues.

The above mentioned methods, chimeric nucleases and vectors may be used for generating genotypic variation in plants.

The following section provides non-limiting applications for generating such a variation.

Thus, chimeric nucleases of the present invention may be used to generate a signature of randomly inserted nucleic acids in a sequence-specific manner, also referred to herein as tagging. This signature may be used as a "genetic mark". This term is used herein distinctively from the common term "genetic marker". While the latter term refers to naturally occurring genetic variations among individuals in a population, the term genetic mark as used herein specifically refers to artificial (man generated), detectable genetic variability, which may be inherited.

The DSB is typically directed into non-coding regions (non open reading frame sequence) so as not to affect the plant's phenotype (e.g. for tagging). However, tagging can also be directed to a coding region. A high quality genetic mark is selected unique to the genome of the plant and endures sequence variation which may be introduced along the generations.

For some, e.g., regulatory, purposes it may be desired to mark commercially distributed plants with publicly known marks, so as to enable regulatory authorities to readily identify the mark, so as to identify the manufacturer, distributor, owner or user of the marked organism. For other purposes secrecy may be advantageous. The latter is true, for example, for preventing an attempt to genetically modify the genetic mark of a supreme event protected by intellectual property laws.

An intellectual property protected organism which is also subject to regulation will therefore be, according to a useful embodiment of the present invention, genetically marked by (a) at least one unique DNA sequence which is known in public; and (b) at least one unique DNA sequence that is unknown, at least not as a genetic mark, in public.

To introduce a heterologous sequence (e.g., coding or non-coding), DSBs will first be generated in plant DNA as described herein. It is well known those of skill in the art that integration of foreign DNA occurs with high frequency in these DNA brake sites [Salomon et al., EMBO J. (1998) 17: 6086-6095; Tzfira et al., Plant Physiol (2003) 133: 1011-

1023; Tzfira et al., Trends Genet (2004) 20: 375-383, Cai et al. (2009) Plant Mol. Biol. Accepted: 14 Dec. 2008]. Once present in the target cell, for example on episomal plasmids, foreign DNA may be cut out from the plasmid using the same ZFN used to generate DSBs in the plant DNA. The foreign DNA released from the episomal plasmid will then be incorporated into the cell DNA by plant non-homologous end joining (NHEJ) proteins. The DSBs may also lead to enhanced homologous recombination (HR)-based gene targeting in plant cells (Puchta et al. Proc Natl Acad Sci USA (1996) 93: 5055-5060).

As mentioned, the present teachings can be used to generate genotypic variation. Thus, the chimeric nucleases of the present teachings can be designed to generate DSBs in coding or non-coding regions of a locus of interest so as to introduce the heterologous gene of interest. Such alterations in the plant genome may consequently lead to additions or alterations in plant gene expression (described in detail hereinabove) and in plant phenotypic characteristics (e.g. color, scent etc.).

Additionally chimeric nucleases can be used to generate genotypic variation by knocking out gene expression. Thus chimeric nucleases can be designed to generate DSBs in coding or non-coding regions of a locus of interest so as to generate a non-sense or mis-sense mutation. Alternatively, two pairs of chimeric nucleases can be used to cleave out an entire sequence of the genome, thereby knocking out gene expression.

Chimeric nucleases of the present invention may also be used to generate genotypic variations in gametes and seeds of the plant. Thus, the chimeric nucleases of the present invention may be used to generate specific or non-specific mutations in gametes which, following fertilization, will generate genotypically modified seeds and consequently modified plants.

Chimeric nucleases of the present invention may also be used to generate variability by introducing non-specific mutations into the plant's genome. This may be achieved by the use of non-specific DNA restrictases or Non-stringent Fok1.

As an alternative, the chimeric nucleases of the present invention may be used to combat infections by plant pathogens.

Thus the present invention envisages a method of treating a plant infection by a pathogen. The method comprising introducing into the plant at least one expression vector encoding at least one chimeric nuclease which comprises a DNA binding domain and a nuclease, wherein the DNA binding domain mediates targeting of the nuclease to the genome of the pathogen, thereby of preventing or treating a plant infection by a pathogen.

As used herein a "plant pathogen" refers to an organism, which causes a disease in the infected plant. Organisms that cause infectious disease include fungi, oomycetes, bacteria, viruses, viroids, virus-like organisms, phytoplasmas, protozoa, nematodes and parasitic plants.

Since complete destruction of the DNA of the pathogen is desired, the chimeric nuclease is designed so as to cleave as much sequence sites on the pathogen's DNA as possible. Thus, repeating sequences may be targeted. Additionally or alternatively a number of distinct sequences are targeted sufficient to induce degradation of the pathogen's DNA.

According to some embodiments of this aspect of the present invention, the chimeric nuclease is designed to cleave the DNA of the pathogen but not that of the plant. To this end, the chimeric nuclease is designed devoid of a localization signal, such that the chimeric nuclease is active in the cytoplasm which comprises the pathogen's (e.g., virus) DNA but not that of the plant.

Alternatively, the nuclease may be designed so as to cleave sequences which are specific for the pathogen but are absent from the plant's genome. This may be achieved using routine bioinformatics analysis such as by the use of alignment software e.g., Blast (wwwdotncbidotnlmdotnihdotgov/blast/Blastdotcgi).

A non-limiting list of plant viral pathogens which may be targeted using the teachings of the present invention include, but are not limited to Species: *Pea early-browning virus* (PEBV), Genus: *Tobravirus*. Species: *Pepper ringspot virus* (PepRSV), Genus: *Tobravirus*. Species: *Watermelon mosaic virus* (WMV), Genus: *Potyvirus* and other viruses from the *Potyvirus* Genus. Species: *Tobacco mosaic virus* Genus (TMV), *Tobamovirus* and other viruses from the *Tobamovirus* Genus. Species: *Potato virus X* Genus (PVX), *Potexvirus* and other viruses from the *Potexvirus* Genus. Thus the present teachings envisage targeting of RNA as well as DNA viruses (e.g. Gemini virus or Bigeminivirus). Geminiviridae viruses which may be targeted include, but are not limited to, *Abutilon mosaic bigeminivirus, Ageratum yellow vein bigeminivirus, Bean calico mosaic bigeminivirus, Bean golden mosaic bigeminivirus, Bhendi yellow vein mosaic bigeminivirus, Cassava African mosaic bigeminivirus, Cassava Indian mosaic bigeminivirus, Chino del tomaté bigeminivirus, Cotton leaf crumple bigeminivirus, Cotton leaf curl bigeminivirus, Croton yellow vein mosaic bigeminivirus, Dolichos yellow mosaic bigeminivirus, Euphorbia mosaic bigeminivirus, Horsegram yellow mosaic bigeminivirus, Jatropha mosaic bigeminivirus, Lima bean golden mosaic bigeminivirus, Melon leaf curl bigeminivirus, Mung bean yellow mosaic bigeminivirus, Okra leaf-curl bigeminivirus, Pepper haustico bigeminivirus, Pepper Texas bigeminivirus, Potato yellow mosaic bigeminivirus, Rhynchosia mosaic bigeminivirus, Serrano golden mosaic bigeminivirus, Squash leaf curl bigeminivirus, Tobacco leaf curl bigeminivirus, Tomato Australian leafcurl bigeminivirus, Tomato golden mosaic bigeminivirus, Tomato Indian leafcurl bigeminivirus, Tomato leaf crumple bigeminivirus, Tomato mottle bigeminivirus, Tomato yellow leaf curl bigeminivirus, Tomato yellow mosaic bigeminivirus, Watermelon chlorotic stunt bigeminivirus* and *Watermelon curly mottle bigeminivirus*.

The present invention also envisages a method of generate male sterility in a plant. The method comprising upregulating in the plant a structural or functional gene of a mitochondria or chloroplast associated with male sterility by introducing into the plant at least one viral expression vector encoding at least one chimeric nuclease which comprises a DNA binding domain, a nuclease and a mitochondria or chloroplast localization signal and a nucleic acid expression construct which comprises at least one heterologous nucleic acid sequence which can upregulate the structural or functional gene of a mitochondria or chloroplast when targeted into the genome of the mitochondria or chloroplast, wherein the DNA binding domain mediates targeting of the heterologous nucleic acid sequence to the genome of the mitochondria or chloroplast, thereby generating male sterility in the plant.

Thus for example, the nucleic acid construct comprises a coding (e.g., for a CMS associated gene) or non-coding (e.g., powerful promoter for enhancing expression of a CMS associated gene) heterologous nucleic acid sequence as well as a binding site for the chimeric nuclease (identical to that on the mitochondria or chloroplast genome). Upon cleavage by the chimeric nuclease, the heterologous nucleic acid sequence is inserted into the predetermined site in the genome of the chloroplast or mitochondria.

As mentioned hereinabove, cytoplasmic male sterility (CMS) is associated with mitochondrial dysfunction. To this effect, the chimeric nucleases are designed to comprise a mitochondria localization signal (as described in detail hereinabove) and cleavage sites which are specific for the mitochondrial genome. Specific genes which may be upregulated include, but are not limited to, the *Petunia* pcf chimera that is located with close proximity to nad3 and rps12, the Rice (*Oryza sativa*) sequence which is downstream of B-atp6 gene (i.e. orf79), the Maize T-urf13 and orf221, the *Helianthus* sp. orf239 downstream to atpA, the *Brassica* sp. orfs which are upstream to atp6 (e.g. orf139 orf224 or orf138 and orf158). It will be appreciated that in order to induce CMS, these genomic sequences are typically transcribed in the plant, thus the teachings of the present invention envision targeting these sequences (e.g. by adding coding sequences) or overexpression thereof using the above described methods as to achieve CMS.

It will be appreciated that CMS phenotype, generated by the incompatibility between the nuclear and the mitochondrial genomes, is used as an important agronomical trait which prevents inbreeding and favors hybrid production.

As mentioned hereinabove, induction of CMS can also be achieved by overexpression of a chloroplast gene such as β-ketothiolase. Overexpression of β-ketothiolase via the chloroplast genome has been previously shown to induce CMS [Ruiz at al (2005) Plant Physiol. 138 1232-1246]. Thus, the present teachings also envision targeting chloroplast genes or overexpression thereof (e.g. (3-ketothiolase) using the above described methods in order to achieve CMS.

The present invention further envisages a method of generating a herbicide resistant plant. The method comprising introducing into the plant at least one viral expression vector encoding at least one chimeric nuclease which comprises a DNA binding domain, a nuclease and a chloroplast localization signal, wherein the DNA binding domain mediates targeting of the nuclease to a gene conferring sensitivity to herbicides, thereby generating the herbicide resistant plant.

It will be appreciated that in the field of genetically modified plants, it is well desired to engineer plants which are resistant to herbicides. Furthermore, most of the herbicides target pathways that reside within plastids (e.g. within the chloroplast). Thus to generate herbicide resistant plants, the chimeric nucleases are designed to comprise a chloroplast localization signal (as described in detail hereinabove) and cleavage sites which are specific for the chloroplast genome. Specific genes which may be targeted in the chloroplast genome include, but are not limited to, the chloroplast gene psbA (which codes for the photosynthetic quinone-binding membrane protein $Q_B$, the target of the herbicide atrazine) and the gene for EPSP synthase (a nuclear gene, however, its overexpression or accumulation in the chloroplast enables plant resistance to the herbicide glyphosate as it increases the rate of transcription of EPSPs as well as by a reduced turnover of the enzyme).

Chimeric nucleases and expression constructs of the present teachings may, if desired, be presented in a pack or dispenser device or kit. The pack may, for example, comprise metal or plastic foil, such as a blister pack. The pack or dispenser device may be accompanied by instructions for use.

It is expected that during the life of a patent maturing from this application many relevant viral vectors and chimeric nucleases will be developed and the scope of these terms is intended to include all such new technologies a priori.

As used herein the term "about" refers to ±10%

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Viral Vectors and Zinc Finger Nucleases

Plant Material

Rooted plantlets of *Petunia hybrida* lines B1, P720, Burgundy and Royal Blue (Danziger-"Dan" Flower Farm, Mishmar Hashiva, Israel) were routinely used for *Agrobacterium tumefaciens* infection for transient expression of foreign genes.

Other plants used for inoculation experiments included *Solanum pimpinellifolium* La121 (Davis University Gene bank), *Capsicum annuum* indra1750 (S&G Syngeta global LTD.), *Arabidopsis thaliana* [Greenboim-Wainberg et al. (2005) Plant Cell, 17: 92-102], *Artemisia* sp. (Danziger-"Dan" Flower Farm, Mishmar Hashiva, Israel), *Nicotiana benthamiana* [Radian-Sade et al., Phytoparasitica (2000) 28:79-86], *Spinacia oleracea* and *Beta vulgaris* (Eden Seeds, Reut, Israel), *Nicotiana tabacum* CV SAMSUNG [Levy et al. (2004) Plant Physiol 135:1-6], *Nicotiana tabacum* CV XANTHI [Ovadis et al. (1999) In "Plant Biotechnology and In Vitro Biology", Kluwer Academic Press, the Netherlands, pp. 189-192], *Cucumis sativus* (Eden Seeds, Reut, Israel), *Solanum melongena* (M. Ben-Sachar LTD, Tel-Aviv, Israel), *Gossypium hirsutum* cv. Siv'on [Saranga et al (2004) Plant, Cell and Environment 27, 263-277) *Brassica napus* [Nesi et al., C. R. Biologies 331 (2008) 763-771], *Zea mays* Var. Royalty F1 (M. Ben-Sachar LTD, Tel-Aviv, Israel). All plants were grown in a greenhouse under 25° C./20° C. day/night temperatures and under a natural photoperiod.

Plasmid Construction pTRV1 a pYL44 binary T-DNA vector carrying the entire sequence of cDNA corresponding to TRV Ppk20 strain RNA1 (GenBank accession No. AF406990) and pTRV2 (GenBank accession No. AF406991) vectors were used [Liu et al. Plant J (2002) 30: 415-429]. pTRV2 containing GUS (pTRV2-Gus) were generated by cloning GUS from pBI101 (Clontech Laboratories) into MCS (XbaI-SacI sites) of pTRV2. pTRV2 containing PAP1 (pTRV2-Δ2b-Pap) were generated by cloning PAP1 from pCHFS-PAP1 [Borevitz et al., The Plant Cell (2000) 12:2383-2393] into MSC (EcoRI-BamHI sites) of pTRV2-Δ2b.

Generating pTRV2 for transient expression of target genes was carried out by removal of the 300 bp of the RNA2 2b gene from the original vector. For this, pTRV2 DNA was digested with PvuII and EcoRI and the deleted fragment containing part of 2b was replaced with a PCR fragment. This fragment was generated by PCR using pTRV2 DNA as a template and primers A and B (see Table 1, below). It was digested with PvuII and EcoRI prior to recloning. The resultant plasmid (pTRV2Δ2b) was identical to the original pTRV2 but lacking the 2b sequence. The plasmid pTRV2 without 2b but with GUS (pTRV2Δ2b-Gus) was generated in the same way except that pTRV2-Gus was used as a recipient plasmid instead of pTRV2.

For generation of pTRV2 containing full length of TRV 2b (pTRV2-2b) a PCR fragment of 1.5 Kbp was generated with primers A and C (see Table 1, below) using as a template pK202b-GFP [Velhos et al., Virology (2002) 300:118-124]. The amplified fragment included the 2b gene (from Ppk20 strain GenBank accession No. Z36974) with 5' and 3' UTRs plus sub-genomic-promoter (sg-P) of the coat protein (CP) from Pea Early Browning Virus (PEBV) (GenBank accession no X78455). This sg-P was sited downstream to 2b. For generation of pTRV2-2b containing GFP (GenBank accession No. U62637) downstream to sg-P (pTRV2-2b-Gfp), the PvuII-EcoRI fragment was transferred from pK202b-GFP to pTRV2 digested with the same enzymes.

For generation of pTRV2Δ2b containing sg-P with downstream GFP (pTRV2Δ2b-Gfp), a PCR fragment was prepared using primers F and G* (see Table 1, below) and pK202b-GFP as a template. This fragment was then digested with SacI and SmaI and cloned into the pTRV2Δ2b digested with the same enzymes. * Of note, Primer G adds a silence mutation to Gfp in order to eliminate a SacI site upstream to the termination codon.

A Gus gene with and without Ω [Broido et al., Physiologia Plantarum (1993) 88: 259-266] was cloned into the MCS of pTRV2Δ2b-Gfp, upstream to sg-P of PEBV to generate pTRV2Δ2b-ΩGus-Gfp and pTRV2Δ2b-Gus-Gfp, respectively. The GUS fragment was generated following digestion of pTRV2-Gus by EcoRI and SacI. ΩGus fragment was generated by cloning GUS into SalI-BamHI sites downstream to the Ω sequence of TMV (Broido et al., supra) into pDrive (Qiagen) and then digesting the resultant plasmid with XbaI-KpnI to release ΩGus and reconstruct it into pTRV2Δ2b-Gfp.

pTRV2Δ2b containing ΩGus (pTRV2Δ2b-ΩGus) was generated by cloning GUS into SalI-BamHI sites downstream to the Ω sequence of TMV (Broido et al., supra) into a pBluescript SK+ (Stratagen) and then digesting the resultant plasmid with KpnI-SacI to release ΩGus and reconstruct it into pTRV2Δ2b.

A pTRV2Δ2b carrying the Tomato bushy stunt virus silencing suppressor p19 (pTRV2Δ2b-p19) was constructed by transferring a 519-bp PCR fragment encoding p19 (using primers D and E, see Table 1, below) from pCB301-p19 [Voinnet et al., Plant J. (2003) 33: 949-956] into pTRV2Δ2b (Obermeier et al., Phytopathology (2001) 91:797-806].

All newly formed pTRV2 constructs were first transformed into *E. coli* and into *Agrobacterium tumefaciens* AGLO [Zuker et al Mol. Breeding. (1999) 5:367-375]. Gus activity in *Agrobacterium* was evaluated qualitatively with X-gluc solution as previously described [Zuker et al., supra]. GFP expression in *Agrobacterium* was analyzed qualitatively using fluorescence stereomicroscope (Leica Microsystems, Wetzlar, Germany).

pTRV2Δ2b containing sg-P with downstream DsRed2 (DsRed, GenBank accession no AY818373 nucleotides 1395-2074 of DsRed, SEQ ID NO: 129, pTRV-Δ2b-sgP-DsRed) was generated by preparing a PCR fragment using as a template pSAT6-DsRed2-N1 and primers H and I (see Table 1, below). The PCR product was then digested with HpaI and SacI, blunt ended with T4 DNA polymerase and cloned (instead of GFP) into the pTRV-2Δ2b-GFP digested with HpaI and SmaI.

Two different combinations of two fluorescence genes in pTRV2 were constructed:

A 2A-like 54 nucleotide sequence (GenBank accession no AF062037 nucleotides 502-555, SEQ ID NO: 81), a *Thosea asigna* virus (TaV-T2A) [Donnelly et al (2001) J. Gen. Virol, 82, 1027-1041; Osborn et al (2005) Mol. Therapy, 12, 569-574], was utilized to create a bicistronic plasmid vector encoding a single, long, ORF consisting of the DsRed2 gene and the NLS-EGFP genes. The sequence (coding for an 18 amino acid peptide), when inserted into single RNA molecule containing two ORFs, allowed separate translation for the two ORFs [Donnelly et al (2001) supra; Osborn et al (2005), supra].

The T2A sequence was modified at the nucleotide level, based on *Petunia* codon usage (worldwidewebdotkazusadotordotjp/codon/cgi-bin/showcodon.cgi?species=4102) and the modified sequence was termed pTRV-T2A (see FIG. 2A).

A plasmid containing the pTRV-T2A sequence inserted between DsRed2 and NLS-EGFP was generated by first generating a PCR fragment using pSAT6-NLS-P1-36-ZFN1 as a template following triple PCR reaction with two foreword primers J & K (Table 1, below) and reverse primer S (Table 1, below) for FoKI. The resultant product was cloned into BamHI and SacI sites of pBluescript SK (pBS) lacking XhoI site, to generate pBS-T2A-P36-ZFN2. EGFP (GenBank accession no AY818363, SEQ ID NO: 130) was PCR amplified using primers N & O (Table 1, below) and cloned downstream to NLS into XhoI and SacI digested pBS-T2A-P36-ZFN1, instead of ZFN. The resultant plasmid was termed pBS-T2A-NLS-EGFP. The DsRed2 was amplified using primers H & M (Table 1, below). The resultant stop codon-lacking DsRed2 was ligated SalI-BamHI fragment into the pBS T2A-NLS-EGFP upstream to T2A, yielding pBS-DsRed-T2A-NLS-EGFP with the bicistronic ORF. The DsRed-T2A-NLS-EGFP fragment from the plasmid was then ligated into HpaI-SacI sites of pTRV2-Δ2b-sgP to generate pTRV2-Δ2b-sgP-DsRed-T2A-NLS-EGFP.

A pTRV2-Δ2b-sgP containing two fluorescent marker genes was generated under separate subgenomic promoters in which pTRV2-Δ2b-sgP-GFP was first digested with SmaI. The PCR fragment generated using pTRV2-Δ2b-sgP-DsRed as a template and primers P & Q (see Table 1, below) was cloned into this SmaI, to produce pTRV2-Δ2b-sgP-GFP-sgP-DsRed.

TABLE 1

Primers

| Primer | Sequence |
| --- | --- |
| A | TGGAGTTGAAGAGTTATTACCGAACG (SEQ ID NO: 1) |
| B | AAGAATT CGAAACTCAAATGCTACCAA (SEQ ID NO: 2) |
| C (PEBV-sgP R) | TAGAATTCTCGTTAACTCGGGTAAGTGA (SEQ ID NO: 3) |
| D (P19-F) | AAACTCGAGATGGAACGAGCTATACAAGGAA (SEQ ID NO: 4) |
| E (P19-R) | AAACCCGGGAGAGTCTGTCTTACTCGCCTTCT (SEQ ID NO: 5) |
| F (5'-PEBV-sgP-F) | AAGAGCTCGAGCATCTTGTTCTGGGGTT (SEQ ID NO: 6) |
| G (GFPuv-3'-SmaI) | ACCCGGGTTATTTGTAGAGTTCATCCATGCCA (SEQ ID NO: 7) |

TABLE 1-continued

Primers

| Primer | Sequence |
| --- | --- |
| H (DsRFP-F-HpaI) | AGTTAACGAGATGGCCTCCTCCGAGA (SEQ ID NO: 53) |
| I (DsRed2-R-SacI) | TAGAGCTCTCACAGGAACAGGTGGTGGC (SEQ ID NO: 54) |
| J (T2A-F-BamHI) | TTTGGATCCGAAGGAAGAGGATCTCTTC<u>TTACTTGTGGTGATGTTGAAGAG</u> (SEQ ID NO: 55) |
| K (T2A-<u>NLS</u>-F-first) | TTACTTGTGGTGATGTTGAAGAGAATCCTGGACCAAAAAAGAAGAGAAAG (SEQ ID NO: 56) |
| L (R-FokI SacI) | AAGAGCTCTTAGGATCCAAAGTTTATCTC (SEQ ID NO: 57) |
| M (DsRFP-R-BamHI) | AGGATCCCAGGAACAGGTGGTGGC (SEQ ID NO: 58) |
| N (EGFP-F-XhoI) | A TCT CGA GTG AGC AAG GGC GA (SEQ ID NO: 59) |
| O (EGFP-R-SacI) | AGAGCTCTACTTGTACAGCTCGTCCATG (SEQ ID NO: 60) |
| NLS (uppercase) | atggtgCCAAAAAAGAAGAGAAAGGTAGAAGACCCCtctcgag (SEQ ID NO: 61) |
| P (2sg F1 Sma) | CCCGGGATTTAAGGACGTGAACTCTGT (SEQ ID NO: 62) |
| Q (dsRed R678 Sma) | CCCGGGTCACAGGAACAGGTGGT (SEQ ID NO: 63) |
| R (NLS linking gene) | AGTTAACGAGATGCCAAAAAAGAAGAGAAAGGT (SEQ ID NO: 64) |
| S (FokI-m-R-SacI) | AAGAGCTCTTAaGATCCAAAGTTTATCTC (SEQ ID NO: 65) |
| T (FokI-m-R-SmaI) | ACCCGGGTTATCCAAAGTTTATCTCGCCGT (SEQ ID NO: 66) |
| U (F-QEQ-ZFN) | AACTCGAGAAAAACTGCGGAACGGA (SEQ ID NO: 67) |
| V (Rssu tp-F-HpaI) | AGTTAACGAGATGGCTTCTATGATATCCTCT (SEQ ID NO: 68) |
| W (ATP-β-tp-F-HpaI) | AGTTAACGAGATGGCTTCTCGGAGG (SEQ ID NO: 69) |

Cloning of pTRV2 Viral Vectors Allowing Targeting of Gene Products to Plastids

To generate EGFP targeted to chloroplast, inventors amplified a PCR fragment containing transit peptide of Pea ribulose-1,5-bisphospate carboxylase small subunit (Rssu) (GenBank accession no X00806, nucleotides 1086-1259, SEQ ID NO: 138) fused to EGFP with primers V & O (see Table 1, above) using the plasmid pTEX-Rssu-GFP previously described by Bezawork [Bezawork (2007) M. Sc Thesis, submitted to Agricultural Research Organization, Volcani center and the Faculty of Agriculture] as a template. The PCR product, following blunting with HpaI, was cloned downstream to sgP into pTRV2-Δ2b-sgP to produce pTRV2-Δ2b-sgP-Rssu-EGFP.

To generate EGFP targeted to mitochondria, inventors amplified a PCR fragment containing a signal peptide of Nicotiana sylvestris ATPase beta subunit (ATP-β) (GenBank accession no U96496, nsatp2.1.1, nucleotides 12 to 167, SEQ ID NO: 139) fused to EGFP with primers W & O (see Table 1, above) using the plasmid pTEX-ATPβ-GFP previously described by Bezawork [Bezawork (2007), supra] as a template. The PCR product, following blunting with HpaI, was cloned downstream to sgP into pTRV2-Δ2b-sgP to produce pTRV2-Δ2b-sgP-ATPβ-EGFP.

Inoculation of Plants with TRV Vectors

Agrobacterium tumefaciens (strain AGLO) transformed with pTRV1, pTRV2 and pTRV2 derivatives were prepared as previously described [Liu et al., Plant J (2002) 30: 415-429]. The Agrobacterium culture was grown overnight at 28° C. in LB medium complemented with 50 mg/L kanamycin and 200 μM acetosyringone (A.S.). The cells were harvested and resuspended in inoculation buffer containing 10 mM MES, 200 μM A.S. and 10 mM MgCl2 to an OD600 of 10. Following an additional 3 hours of incubation at 28° C., the bacteria with the pTRV1 was mixed with the bacteria containing the pTRV2 derivates at a 1:1 ratio. When co-infection of more then one pTRV2 was involved, the *Agrobacteria* with pTRV1 were always 50% in the mixture. 200-400 μl of the *Agrobacteria* mixture was used for injection into the stem. *Agrobacteria* were also injected into the exposed shoot surface following removal of the apical meristems.

Another option for infection was leaf infiltration using a syringe without a needle: *Agrobacteria* content of the syringe was discharged into the scratched surface of the leaf. For infection of plants with TRV, without the use of *Agrobacteria*, first *N. benthamiana* or *N. clevelandii* (the usual host for TRV) was inoculated with pTRV1 and pTRV2 or its derivatives. About 15 to 21 days post infection (dpi) plant leaves (as a source for freshly prepared sap infection) were collected and the sap was extracted in 20 mM phosphate buffer (pH-6.8) by mortar and pestle.

For virion infection of plants (TRV infection without use of *agrobacteria*), inventors first inoculated *Petunia hybrida, Nicotiana tabacum* cv Samsung or *N. benthamiana*, (the usual hosts for TRV) with pTRV1 and pTRV2 (or its derivatives). About 5 to 21 days post infection (dpi) inventors collected plant leaves and extracted the sap in 20 mM phosphate buffer pH=6.8 and a surfactant (e.g. 0-0.03% Silwet L-77) by mortar and pestle. The TRV containing sap was dripped onto cheesecloth or centrifuged and following addition of carborundum fine powder (to improve infection) stems and leaves of young (approximately 1 month old) plants were gently scratched.

Sap infection of in-vitro grown plants: sap was first passed through 0.22 μm filter and then stems of tissue culture propagated plants were injured and infected using syringe and needle.

For *Zea mays* (monocotyledons) infection, the seeds were incubated with the sap during swelling and sprouting (for approximately 1-2 weeks).

In addition to AGLO strain of *Agrobacterium*, inventors also successfully used the EHA-105 [Tovkach et al., Plant J. (2009) 57, 747-757] strain for the delivery of various pTRV constructs.

For inoculation of in vitro grown plants using *A. tumefaciens* AGLO or EHA-105 bacteria, a MS solution [Murashige and Skoog, Physiol Plant (1962) 15:473-497] without glucose but with 10 mM MgSO$_4$ and 50 μg/ml acetosryngone (A.S.) was used and the concentration of the bacteria was reduced to 0.08-0.8 OD 600 nm for each TRV. Infection was performed essentially as above with sap or via vacuum infiltration.

Floral infection with *Agrobacterium* was done by either floral dipping or flower infiltration. In *Petunia hybrida*, flowers were infiltrated using pTRV1 and pTRV2-Δ2b-sgP-DsRed as previously described for leaf infiltration. *Arabidopsis thaliana* were infected with pTRV1 and pTRV2-Δ2b-sgP-ZFN-QEQ at 0.53 OD by floral dipping as described in Zhang et al. [*Nat Protoc* (2006) 1: 641-646].

Expression Analysis

Each expression experiment was repeated three times and each experiment included at least four plants per treatment. Tested plant meristems (at least 2 per plant) were collected several times during the experimental course. GFP imaging was completed using UV illumination and photographs were taken using fluorescence stereomicroscope (Leica Microsystems, Wetzlar, Germany) equipped with a digital camera and a filter set for excitation at 455-490 nm and emission at more than 515. Gus activity was evaluated using the substrate 1 mM 5-bromo-4 chloro-3-indolyl-β-D-glucoronic acid (X-gluc., Duchefa Biochemie B.V. Haarlem, Netherlands) in an appropriate buffer (Zuker et al., supra). Prior to an overnight incubation with the substrate mixture at 37° C., plant tissue was vacuum infiltrated with the substrate for 30 minutes. The substrate solution was then exchanges with 75-95% ethanol for a few days for chlorophyll bleaching and the tissue was observed using a stereomicroscope.

DsRed2 imaging was completed using UV illumination and photographs were taken using fluorescence stereomicroscope (Leica Microsystems, Wetzlar, Germany) equipped with a digital camera and a filter set for excitation at 530-560 nm and emission at 590-650.

EGFP and DsRed2 imaging was also generated using a confocal laser-scanning microscope (CLSM510, Zeiss Jena Germany). For EGFP, excitation was set at 488 nm and emission at 505-530 nm, for DsRED2, excitation was set at 545 nm and emission at 585-615 nm. Autofluorescence of chlorophyll, excitation was set at 488 nm and emission at more than 650 nm.

Preparation of Protoplasts

*Petunia* leaves were used to generate protoplasts as previously described by Locatelli [Locatelli et al, Plant Cell Reports (2003) 21: 865-871].

Transgenic Plants

The binary vector pRCS2[QQR-TS*::GUS] previously described by Tovkach [Tovkach et. al. (2009), supra] was transferred to *Agrobacterium tumefaciens* which was then used to transform *Petunia hybrida* cv Burgundy and *Nicotiana tobaccum* cv. Samsung using the standard leaf disc transformation method [Guterman et al., Plant Mol. Biol. (2006) 60:555-563].

Identification of Non-Coding Genomic Sequences of *Petunia*

A genomic DNA of *Petunia* cv. Royal Blue was prepared using a standard protocol. Initial digestion of the genomic DNA with EcoRI and HindIII was carried out followed by agarose (1%) gel electrophoresis. Next, 1-1.5 Kbp fragments were extracted from the gel by a gel extraction kit (iNtRON Biotechnology, INC. LTD, KOREA). These fragments were ligated to pBS-SK (IRA Company) to form a semi-genomic library in *E. coli*. Sequences of 110 genomic fragments were generated by Macrogen Inc. (Seoul, Korea). Two BLAST analyses (nucleotide blast and tblastx) were performed with the generated genomic *petunia* sequences against nucleotide collection and non-human, non-mouse ESTs libraries, to allow elimination of all the putatively transcripted/translated DNAs. All sequences with a BLAST E value higher then 5 were further evaluated to identify those with the shortest ORF, for all six reading frames, and with minimum repetitive AAAA and TTTT regions. Finally two *Petunia* genomic DNA fragments were selected as non-coding, non repetitive sequences, P1-25 (1.2 Kbp, FIG. 2B) and P1-36 (1.175 Kbp, FIG. 3).

Within these sequences a target site for zinc finger nuclease (ZFN) was designed Zinc finger proteins are capable of recognizing virtually any 18 bp long target sequence, enough to specify a unique address within plant genome. The target sites (artificial-palindrome-like sequence targets, marked in blue in FIGS. 2-3) used were:

```
P1-25
                                        (SEQ ID NO: 10)
site 1: TCC-TCC-TGC (SEQ ID NO: 11)
site 2: GAG-GGG-GAA

P1-36
``` site 1: ACC-ACC-ATC (SEQ ID NO: 12)

site 2: GGT-TGA-GAG (SEQ ID NO: 13)

Identification of PDS and FHT Sequences as ZFN Target Sites in *Petunia*

The sequence of phytoene desaturase (PDS) exon from *Petunia hybrida* RB was confirmed by resequencing (based on GenBank accession no AY593974.1, SEQ ID NO: 131) and utilized as target sites for ZFNs. The highlighted sequences (FIG. 28A) were utilized as the target sites of PDS-ZFN proteins (SEQ ID NOs: 71 and 73).

The sequence of flavanone 3 beta-hydroxylase (FHT) exon from *Petunia hybrida* RB (GenBank accession no AF022142.1, SEQ ID NO: 133) was identified and utilized as target sites for ZFNs. The sequence was confirmed by resequencing. The highlighted sequences (FIG. 29) were utilized as the target sites of FHT-ZFN proteins (SEQ ID NOs: 75 and 77).

Design of Zinc Finger Nucleases (ZFNs)

The zinc finger proteins coding regions were designed based on a zinc-finger-framework consensus sequence formerly developed by Desjarlais and Berg [Desjarlais and Berg, Proc. Natl. Acad. Sci. USA (1993) 90: 2256-2260]. For example, expression of zinc finger endonuclease with the expected affinity to the gagggggaa sequence on P1-25 *Petunia* random DNA fragment (site 2, SEQ ID NO: 11) the zinc finger 262 bp domain was assembled by PFU polymerase (Invitrogen) in a PCR reaction from the set of the following overlapping oligos: BBO1 (5'GAAAAACCTTA-CAAGTGTCCTGAATGTGGAAAGTCTTTTTCT, SEQ ID NO: 14), BBO2M (5'CAGCGAACACACACAGGT-GAGAAGCCATATAAATGCCCAGAATGTGGTA AAT-CATTCAG, SEQ ID NO: 15), BBO3M (5'CAACGGAC-CCACACCGGGGAGAAGCCATTTAAATGCCCTGAGTGCGGGA-AGAGTTTTT, SEQ ID NO: 16), FtsH2-Z1.1-GAA (SEQ ID NO: 17), P1-25-ZFN2.2 GGG (SEQ ID NO: 18) and P1-25-ZFN2.3 GAG (SEQ ID NO: 19) followed by PCR amplification using the BBO1-XhoI-F (SEQ ID NO: 20) and SDO3-SpeI-R (SEQ ID NO: 21) primers producing the DNA binding domain P1-25-ZFN2bd.

In each PCR reaction, the BBOs and SDOs were mixed at 0.005 pM concentration and amplified for 35 cycles with PFU polymerase (Invitrogen). Similar strategies, only using different oligos (see Table 2, below) have been employed for the assembly of the P1-25-ZFN1bd, P1-36-ZFN1bd and P1-36-ZFN2bd DNA binding domains. An outline of the PCR procedure for assembly of ZF binding domains used in this work is illustrated in FIG. 4.

TABLE 2

Sequences of overlapping oligos used for generation of DNA binding domains P1-25-ZFN1bd, P1-36-ZFN1bd and P1-36-ZFN2bd

| | | P1-25-ZFN1bd |
|---|---|---|
| 41 | P1-25-ZFN1.1 GGA | ACCTGTGTGTGTTCGCTGGTGACGTTCAAGATG AGCACGCTGAGAAAAAGACTTTCCACA (SEQ ID NO: 22) |
| 42 | P1-25-ZFN1.2 GGA | CCCGGTGTGGGTCCGTTGGTGACGTTCAAGAT GAGCACGCTGACTGAATGATTTACCACA (SEQ ID NO: 23) |

TABLE 2-continued

Sequences of overlapping oligos used for generation of DNA binding domains P1-25-ZFN1bd, P1-36-ZFN1bd and P1-36-ZFN2bd

| 24 | ZFN-IV-Mod SDO3 GCA | TCCAGTATGAGTACGTTGATGACGACGCAAA TCTCCAGACTGTGAAAAACTCTTCCCGCAC (SEQ ID NO: 24) |
|---|---|---|
| | | P1-25-ZFN2bd |
| 25 | FtsH2-Z1.1-GAA | ACCTGTGTGTGTTCGCTGGTGCTTCTGA AGGTTGCTAGACTGAGAAAAAGACTTTCCACA (SEQ ID NO: 17) |
| 43 | P1-25-ZFN2.2 GGG | CCCGGTGTGGGTCCGTTGGTGACGA ACCAACTTATCAGAACGACTGAATGATTTACCA CA (SEQ ID NO: 18) |
| 44 | P1-25-ZFN2.3 GAG | TCCAGTATGAGTACGTTGATGACGAACCAA ATTATCAGAACGTGAAAAACTCTTCCCGCAC (SEQ ID NO: 19) |
| | | P1-36-ZFN1bd |
| 45 | P1-36-ZFN1.1 GGT | ACCTGTGTGTGTTCGCTGGTGACGAA CAAGATGTCCAGAAGTAGAAAAAGACTTTCCA CA (SEQ ID NO: 25) |
| 29 | FtsH2-Z3.2-GGT | CCCGGTGTGGGTCCGTTGGTGACGAACAAG ATGTCCAGAAGTACTGAATGATTTACCACA (SEQ ID NO: 26) |
| 35 | FtsH2-Z1a.3 GAT | TCCAGTATGAGTACGTTGATGACGAACCAAA TTTCCAGAAGTTGAAAAACTCTTCCCGCAC (SEQ ID NO: 27) |
| | | P1-36-ZFN2bd |
| 46 | P1-36-ZFN2.1 GAG | ACCTGTGTGTGTTCGCTGGTGACGAACCAAATT ATCAGAACGAGAAAAAGACTTTCCACA (SEQ ID NO: 28) |
| 47 | P1-36-ZFN2.2 TGA | CCCGGTGTGGGTCCGTTGGTGAGAAGCCAAAT GTCCAGCCTGACTGAATGATTTACCACA (SEQ ID NO: 29) |
| 48 | P1-36-ZFN2.3 GGT | TCCAGTATGAGTACGTTGATGACGAACAAGATG TCCAGAAGTTGAAAAACTCTTCCCGCAC (SEQ ID NO: 30) |

Amplified DNA binding domains were cloned as an XhoI-SpeI fragment into the same sites of pSAT6-NLS-FokI, producing the pSAT6-NLS-P1-25-ZFN1 (SEQ ID NO: 31), pSAT6-NLS-P1-25-ZFN2 (SEQ ID NO: 32), pSAT6-NLS-P1-36-ZFN1 (SEQ ID NO: 33) and pSAT6-NLS-P1-36-ZFN2 (SEQ ID NO: 34) expression vectors (FIGS. 5A-D). pSAT6-NLS-FokI consists of pSAT vector [GeneBank AY818383, Tzfira et al., Plant Mol Biol (2005) 57: 503-516], 30 b of the NLS (nuclear localization signal, SEQ ID NO: 46) cloned into NcoI-XhoI sites and a 584 bp fragment of FokI endonuclease (nucleotides 1164 to 1748; GeneBank J04623) cloned into SpeI-BamHI sites of pSAT6.

For expression of His tagged zinc finger endonucleases in *E. coli* cells, the NLS-P1-25-ZFN1, NLS-P1-25-ZFN2, NLS-P1-36-ZFN1 and NLS-P1-36-ZFN2 fragments were cloned as NcoI-BamHI inserts from their corresponding plasmids into the same sites of a modified pET28 (pET28.SX, FIG. 5E), producing pET28.SX-NLS-P1-36-ZFN1, pET28.SX-NLS-P1-36-ZFN2, pET28.SX-NLS-P1-25-ZFN1 and pET28.SX-NLS-P1-25-ZFN2. In pET28.SX, assembled ZFNs are cloned downstream of T7 promoter of pET28 vector (Novagen). Complete ZFN constructs also contained a sequence coding for 6xHis-tag at the C terminus of the protein.

Expression of pET28.SX-NLS-P1-36-ZFN1, pET28.SX-NLS-P1-36-ZFN2, pET28.SX-NLS-P1-25-ZFN1 and pET28.SX-NLS-P1-25-ZFN2 was performed in BL21 GOLD (DE3) PlyS cells (Stratagene). Cell cultures were grown in 100 ml LB medium complemented with Kan (50 ug/ml) and 100 µM $ZnCl_2$ at 22° C. until $OD_{600}$ was 0.6 and then cells were induced with 0.7 mM IPTG for 3 hours. Cells were harvested by centrifugation, resuspended in 35 ml mixture containing 25 mM Tris-HCl (pH 7.5), 300 mM NaCl, 5% glycerol and 100 µM $ZnCl_2$, and lysed twice through a French Press. The protein was loaded on 0.5 ml Ni-NTA agarose beads (Qiagen) and eluted with 1 ml buffer containing 500 mM imidazole. Eluted protein was stored at −20° C. in 50% glycerol.

Various quantities of E. coli and Ni-NTA purified ZFNs were mixed with 0.5 µg of target DNA for in vitro digestion using NEB4 buffer and digested DNA substrates were separated by agarose gel electrophoresis.

Cloning of pTRV2 Viral Vectors Allowing Expression of ZFNs

ZFN inserts in pSAT constructs (pSAT6-P1-36-ZFN1, pSAT6-P1-36-ZFN2, pSAT6-PDS-ZFN1, pSAT6-PDS-ZFN2, pSAT6-FHT-ZFN1, pSAT6-FHT-ZFN2) start and end with nonspecific domains, NLS and FokI respectively. To generate pTRV2 suitable for delivery and expression of different ZFNs in plant cells, inventors amplified ZFNs using the forward primer R and the reverse primers L (for pSAT6-P1-36-ZFN2, pSAT6-PDS-ZFN1, pSAT6-FHT-ZFN1) or T (for pSAT6-P1-36-ZFN1, pSAT6-PDS-ZFN2, pSAT6-FHT-ZFN2) (see Table 1, above). The resultant amplification products were digested with HpaI and SacI (for primer L) or SmaI (for primer T), blunt ended (in case of SacI) and inserted into HpaI-SmaI sites of pTRV2-Δ2b-sgP. This lead to the generation of pTRV2-Δ2b-sgP-PDS-ZFN1 (FIG. 31A, SEQ ID NO: 70), pTRV2-Δ2b-sgP-PDS-ZFN2 (FIG. 31B, SEQ ID NO: 72); pTRV2-Δ2b-sgP-FHT-ZFN1 (FIG. 32A, SEQ ID NO: 74), pTRV2-Δ2b-sgP-FHT-ZFN2 (FIG. 32B, SEQ ID NO: 76); pTRV2-Δ2b-sgP-P36-ZFN1 (SEQ ID NO: 33) and pTRV2-Δ2b-sgP-P36-ZFN2 (SEQ ID NO: 34).

To generate pTRV2-Δ2b-sgP-QEQ-ZFN (SEQ ID NO: 82), inventors first generated a PCR product using primers U and S (see Table 1, above) and pSAT4.hspP.QQR [Tovkach et al (2009), supra] as a template. The product was digested with XhoI and SpeI and inserted into XhoI and SpeI digested, ZF lacking, plasmid pTRV2-Δ2b-sgP-P36-ZFN2 (FIG. 33).

To generate a construct containing two ZFNs linked with T2A (pTRV2-Δ2b-sgP-P36-ZFN2-T2A-P36-ZFN1, SEQ ID NO: 84), the BamHI fragment from pTRV2-Δ2b-sgP-P36-ZFN2 containing the sgP-NLS-P1-36-ZFN2 was cloned into the unique BamHI site in pBS-T2A-NLS-36-ZFN1. This generated pBS-sgP-P36-ZFN2-T2A-P36-ZFN1. This plasmid was digested with SacI and the released fragment containing sgP-P36-ZFN2-T2A-P36-ZFN1 was cloned into pTRV2-Δ2b linearized with SacI to generate pTRV2-Δ2b-sgP-P36-ZFN2-T2A-P36-ZFN1.

To generate pTRV2-Δ2b-sgP-PDS-ZFN1-T2A-PDS-ZFN2 (SEQ ID NO: 86) and pTRV2-Δ2b-sgP-FHT-ZFN1-T2A-FHT-ZFN2 (SEQ ID NO: 88), inventors first digested pBS-T2A-NLS-36-ZFN1, pSAT6-FHT-ZFN2 and pSAT6-PDS-ZFN2 with XhoI & SpeI (flanking ZF sequences). Inventors then ligated fragments released from the latter two plasmids into digested pBS-T2A-NLS-36-ZFN1 to create pBS-T2A-NLS-PDS-ZFN2 and pBS-T2A-NLS-FHT-ZFN2. Plasmids pTRV2-Δ2b-sgP-PDS-ZFN1 and pTRV2-Δ2b-sgP-FHT-ZFN1 were digested with BamHI to release sgP-PDS-ZFN1 and sgP-FHT-ZFN1, which were then ligated into BamHI digested pBS-T2A-NLS-PDS-ZFN2 and pBS-T2A-NLS-FHT-ZFN2, respectively. These plasmids were digested with SacI and the released fragments were cloned into unique SacI site of the MCS in pTRV2-Δ2b yielding pTRV2-Δ2b-sgP-PDS-ZFN1-T2A-PDS-ZFN2 and pTRV2-Δ2b-sgP-FHT-ZFN1-T2A-FHT-ZFN2, respectively.

Example 2

Expression of Foreign Genes by pTRV2-Δ2b Vectors

The RNA2-2b fragment (300 bp of SEQ ID NO: 43 depicted in SEQ ID NO: 50) was entirely removed from pTRV2 (GenBank accession No. AF406991) to generate the pTRV2-Δ2b (see Example 1 hereinabove and FIGS. 6A-B). Inventors were interested in the expression of the reporter genes in the meristematic tissues and hence reporter gene expression was evaluated in these tissues. Petunia plants were inoculated with pTRV2-Δ2b-GUS and pTRV2-GUS and the efficiency of foreign gene expression (i.e. GUS) by these vectors was compared. GUS expression was evaluated a week to two month following infection and percent of meristems expressing GUS out of total number of analyzed meristems was presented (see Table 3, below). As clear from the results, pTRV2 without the 2b region was much more efficient in GUS expression in meristimatic tissues. Furthermore, no GUS staining was noticeable in petunia plants inoculated with TRV lacking GUS. Typical GUS expression in the meristems of inoculated plants is illustrated in FIGS. 7A-E. As clear from FIG. 7E, GUS staining in petunia plants following inoculation with pTRV2-Δ2b-GUS was noticeable even after numerous rounds of propagation (via axillary meristems) in tissue culture. Additional marker genes used to assay applicability of pTRV2 based vector for expression of foreign genes were GFP and PAP1. Inoculation of petunia and other plants (Capsicum annuum, Solanum pimpinellifolium, Nicotiana benthamiana, Arabidopsis thaliana, Artemisia annua, Spinacia olerace and Beta vulgaris) with these vectors led to expression of the reporter genes in meristems of all analyzed plants (FIGS. 8A-G).

TABLE 3

Expression of GUS in Petunia plants inoculated with pTRV2-Δ2b-GUS and pTRV2-GUS

| | Days post inoculation | | | | |
|---|---|---|---|---|---|
| | 7 | 13 | 21 | 37 | 48 |
| pTRV2-GUS | 50% | 40% | 11% | 7% | 0% |
| TRV2-Δ2b-GUS | 45% | 60% | 54% | 40% | 60% |

Example 3

Enhancement of Foreign Gene Expression by Ω Translational Enhancer

The 70 bp at the 5'UTR of TMV (Ω) is a non-coding sequence shown to be a translational enhancer (SEQ ID NO: 44) [Gallic et al., Nucl. Acid. Res. (1987) 15:8693-8710]. Ω was cloned upstream to the reporter gene in the pTRV2 viral vectors in order to evaluate whether it can promote expression levels of foreign genes (see FIGS. 6A, C). As illustrated in FIGS. 9A-B, inoculation of petunia plants with pTRV2-

Δ2b-Ω GUS vectors resulted in higher GUS activity levels as compared to that obtained using pTRV2-Δ2b-GUS vectors (lacking the Ω enhancer). It should be noted that the Ω fragment did not affect the percent of meristems expressing GUS out of total number of analyzed meristems.

Example 4

Co-Expression of Two Foreign Genes by pTRV2 Vectors

Two approaches were developed to allow co-expression of two coding sequences. First, a pTRV2 vector was generated that carries an additional subgenomic promoter (sgP) sequence, hence allowing co-expression of two coding sequences (see FIGS. 6A, D). Coat protein subgenomic promoter of PEBV was used to this end. To test vector activity, GFP reporter gene was cloned downstream to this subgenomic promoter to create pTRV2-Δ2b-sgP-GFP. Inoculation of N. benthamiana plants with this vector, led to expression of GFP in meristematic tissues (FIG. 10A).

In an alternative approach aiming to co-express two foreign genes, N. benthamiana plants were co-inoculated with pTRV2-Δ2b-GUS and pTRV2-Δ2b-GFP (FIGS. 10B-C). Co-expression of both reporter genes was revealed based on the analyses of GFP expression in the tissue followed by GUS staining of the same tissues.

Example 5

Expression of Foreign Genes by pTRV Vectors in a Wide Variety of Plants

Inoculation of different plants (e.g. N. benthamiana, N. tobaccum and Petunia hybrida) with pTRV1 and pTRV2-Δ2b-sgP-DsRed lead to a high expression level of the marker gene in cells of these plants (FIGS. 11A-F). Continuous (several months) strong expression, due to systemic infection, was easily detected in different parts of these plants (FIGS. 12A-H). Inoculation of various plants (e.g. Cucumis sativus, Solanum melongena, Gossypium hirsutum cv. Siv'on (cotton), Brassica napus (canola), Beta vulgaris (beet), Spinacia oleracea) with this vector lead to expression of the reporter genes in all analyzed plants (FIGS. 13A-K).

Example 6

Expression of Foreign Genes by TRV Vectors in Monocots

To assay the applicability of pTRV2 based vectors for expression of foreign genes in monocots (e.g. maize), seeds were incubated with sap generated from petunia plants infected with pTRV1 and pTRV2-Δ2b-sgP-DsRed (as depicted in detail in Example 1, hereinabove). FIGS. 14A-C show clear expression of DsRed in coleoptile.

Example 7

Mitochondrial & Chloroplast Plastids

TRV Vector-Mediated Plastid-Targeted Expression

As described in Example 1, hereinabove, inventors have constructed two vectors pTRV2-Δ2b-sgP-Rssu-EGFP and pTRV2-Δ2b-sgP-ATPβ-EGFP containing a chloroplast transit peptide and a mitochondrial signal peptide, respectively. Inventors agroinfiltrated both pTRV2-Δ2b-2sgP-tp-EGFP (tp here is stand for transit peptide and signal peptide) into Petunia hybrida cv RB and N. benthamiana. The EGFP expression was first analyzed by fluorescent stereomicroscope, then the fluorescent leaf zones were analyzed by confocal laser scanning microscope. The chloroplast size and auto fluorescence (excitation at 488 nm, emission more than 650 nm) enabled to localize the expression of EGFP (excitation at 488 nm, emission 505-530 nm) to the chloroplast (FIGS. 15A-G).

For mitochondrial identification, protoplasts were prepared and red fluorescent mitochondrial specific reagent (MitoTracker® Invitogen inc. USA) was employed. The use of excitation 545 nm and emission 585-615 nm allowed distinguishing the fluorescence of chloroplasts from that of MitoTracker. According to the size and location and mitotracker signal, inventors revealed that the expression of EGFP was localized to mitochondria (FIGS. 16A-K).

Example 8

Co-Expression of Two Reporter Genes in Various Plants

Several approaches were used to simultaneously express two genes in plant (Petunia hybrida, N. benthamiana or N. tabacum) cells. In one approach, plants were inoculated simultaneously with two TRV vectors, one carrying one marker gene and another carrying another marker gene. Specifically, plants were co-infection with pTRV1 and two pTRV2 vectors, pTRV2-Δ2b-sgP-DsRed and pTRV2-Δ2b-sgP-Rssu-EGFP. Results of confocal fluorescent scanning microscopy of in vitro Agroinfiltrated Nicotiana tabacum cv Xanthi plants showed co-expression of both EGFP and DsRed (FIGS. 17A-D).

The second and third approaches for co-expression of two genes were demonstrated using pTRV2 constructed with two reporter genes in tandem. The genes were either separated by T2A (FIGS. 18A-L) or were driven by separate double subgenomic promoters (FIGS. 19A-J). As depicted in FIGS. 18A-L, the co-expression of GFP and DsRed was clear following inoculation of plants with pTRV2-Δ2b-sgP-DsRed-T2A-NLS-EGFP. Similarly, as depicted in FIGS. 19A-J, the co-expression of GFP and DsRed was clear following inoculation of plants with pTRV2-Δ2b-sgP-GFP-sgP-DsRed.

Example 9

Generation of Specific Zinc Finger Nucleases (ZFNs)

Petunia non repetitive putatively non-coding genomic sequences were identified following sequencing of 110 genomic fragments (see Example 1, hereinabove). Two sets of ZFN, 25-ZFN-1, 25-ZFN-2 and 36-ZFN-1, 36-ZFN-2, were synthesized in order to form a double cut in the Petunia's specific DNA sequences, P1-25 and P1-36, respectively. To test nuclease activity of the generated ZFNs, PCR fragments were generated containing target sequences in a palindrome-like form and these fragments were incubated with the specific ZFNs. As illustrated in FIG. 20, PCR fragments were digested by each ZFN to the expected sizes.

To further verify ZFNs activities, pBS vectors carrying P1-36 sequences were generated. Incubation of 740 bp fragment of P1-36 carrying target sequences (generated by digestion of pBS-P1-36 with NcoI/BamHI*) with purified ZFNs, 36-ZFN1 and 36-ZFN2, yielded fragments of expected sizes (FIG. 21, depicted by arrows). Of note, BamHI as well as SmaI are part of the multiple cloning sites (MCS) of pBS, right upstream to the cloning site EcoRI. The NcoI site is part of the P1-36 sequence and 200 bp downstream to P1-36 site2. Furthermore, as expected, 36-ZFN1 and 36-ZFN2 individually did not yield digestion products. Moreover, as illustrated in FIG. 22, the combination of 36-ZFN-1 and 36-ZFN-2 successfully digests the target sequence P1-36 carried by pBS-P1-36.

Furthermore, *Petunia* phytoene desaturase (PDS) genomic sequences were identified following sequencing of genomic fragments (see FIG. 28A). Sets of ZFN, PDS-ZFN1 and PDS-ZFN2, were synthesized (as depicted in detail in Example 1, hereinabove) in order to form a double cut in the *Petunia's* specific PDS DNA sequences. To test nuclease activity of the generated ZFNs, plasmids were constructed to carry semi-palindromic target sequences and these plasmids were incubated with the specific ZFNs. As illustrated in FIG. 23, digestion of plasmids carrying artificial target sites PDS1 and PDS2 (PDS-TS1 and PDS-TS2, respectively) by specific ZFNs was carried out. Plasmids were digested by AgeI and PDS-ZFN1 or PDS-ZFN2 to the expected sizes.

In conclusion, the results conclusively show that foreign genes can be expressed in plants meristems, including *petunia* meristems. Additionally, these results show the specific digestion in vitro of *petunia* DNA by ZFNs.

Example 10

Generation of Viral Expression Vectors Comprising ZFNs

The expression of ZFNs by pTRV expression vectors is underway to determine the best approach to co-express ZFNs in *petunia*. Three approaches are being tested each of which is first tested with two fluorescent reporter genes (GFP and DsRFP) as depicted in detail above. These fluorescent reporter genes are delivered to *Petunia* plants and their co-expression within meristematic cells are examined using fluorescent microscopy. Based on these results, ZFNs expression vectors will be generated.

In the first approach, each gene is cloned separately into the pTRV2-Δ2b-Ω into the SalI-SacI site. Plants are then co-infected with the two plasmids of pTRV2 (one carrying GFP and the other carrying DsRFP) simultaneously.

In the second approach genes are both introduced into the same pTRV2 (pTRV2-Δ2b-Ω), each gene with a different sub-genomic promoter (sg-P). Plants are then infected with the pTRV2 plasmid.

The third approach is based on a '2A like' protein that is able to cleave itself at the C termini [(Donnelly et al., J. Gen. Virol. (2001) 82: 1027-1041; Osborn et al., Molecu. Therapy (2005) 12: 569-574]. The '2A-like' protein sequence, EGRGSLLTCGDVEENPGP (SEQ ID NO: 41, T2A) of insect virus *Thosea asigna* mediates an efficient co-translational cleavage event resulting in the release of each individual protein product. The C-termini Pro is the only amino acid that remains with the downstream protein following the self-cleavage. An oligomer was synthesized that encodes these 18 amino acids of the '2A-like' protein (T2A). The nucleotide sequence was designed based on the *Petunia* codon usage (Codon Usage Database wwwdotkazusadotordotjp/codon). To co-translationally express GFP and DsRFP, they are cloned in frame into pTRV2-Δ2b-Ω separated by the T2A 18 amino acids. To deliver ZFNs proteins to the nucleus via this approach, nuclear localization signal (NLS) sequences that start with Pro, are fused to their 5' ends. Hence, Pro are shared by NLS and T2A, i.e. the last 3' Pro of the T2A represents the first amino acid of the NLS. This eliminated the need to introduce additional foreign sequences 5' to NLS. The final insert is KpnI-Ω-NLS-ZFN2-T2A-NLS-ZFN1—SacI. For example, using pTRV2-Δ2b-sgP-CP-PEBV (FIGS. 24A-B) carrying DsRFP and GFP, separated by T2A, *petunia* tissues co-expressing both reporter genes were generated.

An optional modification to the third approach is to clone one of the ZFNs with the T2A at the N termini (T2A-NLS-ZFN1 fragment) downstream and in frame with TRV1 16 K gene (FIG. 6E). In this case the Agro infection of *Petunia* plants is performed with modified pTRV1 and pTRV2, each carrying only one foreign ZFN gene.

Example 11 pTRV-Vector-Mediated Activation of Gus Expression in Plants

Inventors have utilized the zinc finger based transgene repair tool that was previously described by Tovkach et al. [Tovkach et al. (2009), supra] in order to generate *petunia* and tobacco transgenic plants carrying a mutated uidA (GUS) gene. The mutated uidA gene was engineered to carry the TGA (stop) codon within the 6-bp spacer of the QEQ-ZFN target site (see FIG. 25A), leading to premature termination of uidA translation in plant cells. Thus, no GUS expression was detectable in the transgenic plants (FIG. 26I). Digestion of the DNA at the spacer between the ZFNs target site (by the use of specific ZFNs) and its successive repair typically lead to deletion and/or mutation of the stop codon and to the consequent activation of the uidA reporter gene (FIG. 25B). To this end, QEQ-ZFN specific for the mutated uidA gene was cloned into pTRV2-Δ2b-2sgP viral vector (as depicted in detail in Example 1, hereinabove) and the resultant pTRV2-Δ2b-sgP-QEQ-ZFN was used for inoculation of plants transgenic for mutated uidA gene. As clear from the results (FIGS. 26A-J), TRV-driven expression of the QEQ-ZFN in somatic and meristematic tissues lead to activation of GUS expression.

Example 12

Molecular Analysis of Transgenic Tobacco and *Petunia* Plants with Activated

GUS expression following inoculation with pTRV2-Δ2b-sgP-QEQ-ZFN Total plant DNA was extracted from leaves of GUS transgenic *petunia* and tobacco plants (carrying a mutated uidA (GUS) gene) before or 7-30 days after inoculation with pTRV1 and pTRV2-Δ2b-sgP-QEQ-ZFN using the phenol-chloroform method. Total DNA was digested with DdeI for 3 hours and the region surrounding the ZFN target site was PCR-amplified using primers 5'-CTATCCT-TCGCAAGACCCTTCC-3' (35S-F, SEQ ID NO: 90) and 5'-GTCTGCCAGTTCAGTTCGTTGTTC-3' (GUS-R-401, SEQ ID NO: 91). The resulting PCR fragment was redigested with DdeI, and its undigested fraction was reamplified and TA cloned into pGEM-T-easy (Promega inc., WI, USA). Randomly selected colonies were then selected and the DNA fragments sequenced.

FIG. 27 shows the changes in the GUS sequence following activation by QEQ-ZFN, as compared to the original GUS sequence in the transgenic *N. tabacum* or *Petunia* plants.

Example 13

Molecular Analysis of Modified PDS in *Petunia* Plants Following Inoculation with Specific ZFNs As depicted in detail in Example 1, hereinabove, inventors of the present invention have generated ZFNs which specifically cleave the PDS gene of *petunia* plants. To analyze the molecular modifications made to the PDS gene following inoculation with pTRV2-Δ2b-sgP-PDS-ZFN1-T2A-PDS-ZFN2, total plant DNA was extracted from leaves of wild type (WT) or pTRV1 and pTRV2-Δ2b-sgP-PDS-ZFN1-T2A-PDS-ZFN2 treated *Petunia hybrida* plants using the phenol-chloroform method. The region surrounding the ZFN target site (TS) was PCR-amplified using primers 5'-TATTGAGTCAAAAGGTGGCCAAGTC-3' (phPDS-F 208, SEQ ID NO: 117) and 5'-GCAGATGATCATATGTGT-TCTTCAG-3' (phPDS-R-487, SEQ ID NO: 118). The PCR product was digested with MfeI overnight and the resulting undigested fraction was reamplified and TA cloned into pGEM-T-easy (Promega inc., WI, USA). Inserts from randomly selected colonies were then sequenced. FIG. 28B depicts the changes in the PDS sequence following modification by the specific PDS-ZFNs, as compared to the original PDS sequence in *Petunia* plants.

Example 14

Directly Infecting Floral Organs, Especially the Gametes, Inside the Ovary and the Anther Floral infection with *Agrobacterium* was done by plant infiltration or using a floral dip transformation protocol, previously described for *Arabidopsis* [Mang et al., Nat Protoc (2006) 1: 641-646, incorporated herein by reference], both described in detail in Example 1, above.

The present inventors demonstrated expression of DsRed in different floral organs following infection of plants such as *Capsicum annuum* and *Petunia hybrida* with pTRV1 and pTRV2-Δ2b-sgP-DsRed (FIG. 35A-J). Expression of DsRed was also evident in *Petunia* flowers infected with pTRV1 and pTRV2-Δ2b-sgP-DsRed via floral infection (FIG. 36A-H). These results provide clear support that nucleases can be delivered into reproductive organs enabeling direct generation of genotipically modified gametes.

Inventors further prepared transgenic *Arabidopsis thaliana* (similar to that described above for transgenic *Petunia*) caring the QEQ-ZFN target sites with the stop codon upstream to the coding sequence of uidA (the GUS gene) (as described in further detail in Example 11, above). The transgenic *A. thaliana* plants with defective GUS were used to demonstrate pTRV-vector-mediated transient delivery of nucleases into the flower's reproductive organs. Transgenic plants carrying the defective GUS were inoculated, via the flower dip transformation method (described in Example 1, above) with the binary plasmid (described in detail in Examples 1 and 11, above).

As shown in FIGS. 37A-C, once endonucleases reached and became active in gamete producing cells or gametes, its expression led to DNA breaks within the GUS gene (in between the nuclease recognition sites) and activation of GUS occurred. Seeds formed from such gametes were also genetically modified, i.e. with reactivated uidA gene (as shown in FIGS. 38A-B). These GUS expressing seedlings prove the capability of viral vectors to inducegenome modification in gametes. The advantage in direct transformation of plant reproductive organs as described herein is significant.

For example, TRV based vectors can deliver the endonucleases into meristematic tissue of a plant. Meristematic tissues can relatively easily develop into a new plant. If the meristem cells were modified at the DNA level, the grown mature plant, developing from these modified cells, will comprise a modified genotype. This modified genotype can be efficiently propagated vegetatively. Furthermore, some of the seeds developing in these plants will inherit the modified genome. The latter process of transferring the new genotype to new generations of plants hence has certain limitations: it may depend on the availability of the tissue culture protocols for conversion of meristems into mature ex-vitro grown plants, in many cases it will demand long propagation/culture period/time; since in some plants, as for example trees, it may take years for meristems to become mature plants and then to generate seeds. Thus, the present teachings, which enable direct and indirect modification of plant gametes (in anthers and in ovaries), may be used for crosses with the aim of speeding up and improving breeding programs. Furthermore, in plants that don't support a viral systemic infection, direct infection of the flower/reproductive organs will allow to directly generate gametes with modified genotypes.

In other words, especially for seed propagating plants, but not merely, the present teachings demonstrate for the first time that viral vector can now be used to deliver nucleases into the flower's reproductive organs and introduce genetic variations. Gamete-producing-organs/cells or gametes themselves, which express endonuclease or various endonucleases, are modified. These modified gametes, following fertilization, will generate genotypically modified seeds. The described process extremely facilitates and shortens the procedure for genetic modification of plant.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

<160> NUMBER OF SEQ ID NOS: 145

<210> SEQ ID NO 1
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 1
tggagttgaa gagttattac cgaacg                                          26

<210> SEQ ID NO 2
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 2
aagaattcga aactcaaatg ctaccaa                                         27

<210> SEQ ID NO 3
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 3
tagaattctc gttaactcgg gtaagtga                                        28

<210> SEQ ID NO 4
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 4
aaactcgaga tggaacgagc tatacaagga a                                    31

<210> SEQ ID NO 5
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 5
aaacccggga gagtctgtct tactcgcctt ct                                   32

<210> SEQ ID NO 6
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 6
aagagctcga gcatcttgtt ctggggtt                                        28

<210> SEQ ID NO 7
<211> LENGTH: 32
<212> TYPE: DNA
<213> ORGANISM: Artificial sequence

```
<220> FEATURE:
<223> OTHER INFORMATION: Single strand DNA oligonucleotide

<400> SEQUENCE: 7
acccgggtta tttgtagagt tcatccatgc ca                                         32

<210> SEQ ID NO 8
<211> LENGTH: 1203
<212> TYPE: DNA
<213> ORGANISM: Petunia x hybrida
<220> FEATURE:
<221> NAME/KEY: misc_feature
<223> OTHER INFORMATION: P1-25 Petunia RB random DNA fragment

<400> SEQUENCE: 8
gaattcggac atgtgccaaa tggatagagt ggaatcctcc tactttgggg cggaatcctc           60
ctaccctcaa tatgatgcga ggagcggaat cctcctactc ctagggcgga atcctcatac          120
cctcaatatg atgcaaggag cggaatcctc ctactcctag ggtggaatcc tcctaccctc          180
aatatgatgc aaggagtgga atcctcctac cctcattatg atgcaaggag cagaatcctc          240
ctgctcctag gacggaatcc tcttaccctc aatatgatgt aaggagcgga atcctcctgc          300
tccgaggggg aatcctcctg cctgcaatat aatataaagt tgaggcgaaa tactcctata          360
atcataatat ggcatagcag cccataacca aaaaatataa tacatatgaa tgcggtatga          420
tacaataaca acccttcacc ggtgcgggac ccttatcggt tgccaaaaag tatatgtcaa          480
gctcagaacc agagtacaat gctcagatgc tcaatataat accaacaaca ggacataaca          540
tataatatac aatataaatc caaagctaag gcgtaatgag tacgcctatc ggtagctaca          600
cacgtaagga acacgtggta gaatatccac aaggccaagg gcctccaaag aaatggatat          660
aatcacttac cttattccaa agtgctactc aacaaccgct tgtcctttg ggttcactgc           720 caaacgatcc cactctattc aataagcaga aaaatatatc aaataaggct aaaggcttca          780
ttccttacat cctagaacaa ttcgggtagg aacccaacac ccattttgaa tagacaatac          840
gcggtccagg cctatgtata tggttcaaaa tcacataatc aaaccctaaa taaattacat          900
ttacggggtc caattaacga atatataatc aattccatta tcggggtcca attacccctt          960
gaaactatca atttaactta ttaaaacgat ttttaatatc ccaatttcta ccgtcaaaat         1020
atattcaaac acatgtaata gactaaaata atgaattaac atccttacct ggatgtttcg         1080
ggttgaaaaa tctatttttt tcctgctcct tttcctttct attctctctt tcttgccttt         1140
ttttctcgtt gcgtcctcaa ttgtttcgtt tctgtttctg tttccatttg caaatgtaag         1200
ctt                                                                      1203

<210> SEQ ID NO 9
<211> LENGTH: 1175
<212> TYPE: DNA
<213> ORGANISM: Petunia x hybrida
<220> FEATURE:
<221> NAME/KEY: misc_feature
<223> OTHER INFORMATION: P1-36 Petunia RB random DNA fragment

<400> SEQUENCE: 9
gaattctata gaatggctga ctatgcacta gaactagtcc atgaaccttc cgagaatgtt           60
caaagattta ttgatgacct ttcttttttc tagagatccc agatggctcg agagattgac          120
gtcgggattt catttgatgt tgttgtttat attgcccgaa ggtacgaggc atatcataag          180
ttagagcggg aagagttaga gcaggagagc aagagatccc gtggccctag tgggcaaccg          240
```

```
tggtacctca tttggaggta agagttctgg ttattttggg aggtcacctt ccaggttatc    300
tcagcttgtg tcatgtgatt cttagagtgc gcgggtagtt catcaagatt agactcagct    360
ttctctttgt agctttcaac aatctgtcca gctcccatat tcagcgaaaa ggtgttatca    420
ttctctttgt agctttcaac aatctgtcct gctcagttgt aagggatttc atttagatct    480
taatcagcaa aagaaatacc accatccaat agaggttgag agtgtggtgg cagtggttct    540
ccagaaagtg attgccaggg tagtggctca gctcagctgc agaggcagtt ttatgaactg    600
ccagtctggc aggatgttga ggtatctgat gtagtacatc catgtatttc ttcttccatt    660
atatgtgagt aaattttcat tcttctgatc ggtctggact tcatttattt taccatgttt    720
ccatggtctc tttggatatt gtttctatta agaattgatt gcggtagagg ggtgagcttc    780
tagtatgatt tattcaagga atttgtgaga ccctattaat ttatctggtc taaatatgag    840
agatttgaca atgagtgtcg ttattgtctg cctggcatct tgttgtgcca ccttctatta    900
ttatatcaaa ttagtttacc tctcttctcg gaattccgtg ttggttggat tatgggattc    960
tagttcatca ccataaggga gtgtcatggt ttcttccagt gtaaagtgat tagtaagtaa   1020
tagtcgatct acgtatctcc tcttggttca aaacgctagt aaagtcatgt gatcgtatga   1080
gcttgtctgg attataaaag ggttttctgg taaattgtta gagtttcctt attattggga   1140
gattaaattg gcatggaagt tgttccataa agctt                              1175
```

```
<210> SEQ ID NO 10
<211> LENGTH: 9
<212> TYPE: DNA
<213> ORGANISM: Petunia x hybrida
<220> FEATURE:
<221> NAME/KEY: misc_feature
<223> OTHER INFORMATION: Zinc finger protein DNA binding motif P1-25TS1

<400> SEQUENCE: 10 tcctcctgc                                                              9

<210> SEQ ID NO 11
<211> LENGTH: 9
<212> TYPE: DNA
<213> ORGANISM: Petunia x hybrida
<220> FEATURE:
<221> NAME/KEY: misc_feature
<223> OTHER INFORMATION: Zinc finger protein DNA binding motif P1-25TS2

<400> SEQUENCE: 11 gaggggga                                                               9

<210> SEQ ID NO 12
<211> LENGTH: 9
<212> TYPE: DNA
<213> ORGANISM: Petunia x hybrida
<220> FEATURE:
<221> NAME/KEY: misc_feature
<223> OTHER INFORMATION: Zinc finger protein DNA binding motif P1-36TS1

<400> SEQUENCE: 12 accaccatc                                                              9

<210> SEQ ID NO 13
<211> LENGTH: 9
<212> TYPE: DNA
<213> ORGANISM: Petunia x hybrida
<220> FEATURE:
<221> NAME/KEY: misc_feature
<223> OTHER INFORMATION: Zinc finger protein DNA binding motif P1-36TS2
```

<400> SEQUENCE: 13 ggttgagag                                                                9

<210> SEQ ID NO 14
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 14
gaaaaacctt acaagtgtcc tgaatgtgga aagtcttttt ct                           42

<210> SEQ ID NO 15
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 15
cagcgaacac acacaggtga gaagccatat aaatgcccag aatgtggtaa atcattcag         59

<210> SEQ ID NO 16
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 16
caacggaccc acaccgggga gaagccattt aaatgccctg agtgcgggaa gagttttt          58

<210> SEQ ID NO 17
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 17
acctgtgtgt gttcgctggt gcttctgaag gttgctagac tgagaaaaag actttccaca       60

<210> SEQ ID NO 18
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 18
cccggtgtgg gtccgttggt gacgaaccaa cttatcagaa cgactgaatg atttaccaca       60

<210> SEQ ID NO 19
<211> LENGTH: 61
<212> TYPE: DNA
<213> ORGANISM: Artificial sequence
<220> FEATURE:
<223> OTHER INFORMATION: Single strand DNA oligonucleotide

<400> SEQUENCE: 19
tccagtatga gtacgttgat gacgaaccaa attatcagaa cgtgaaaaac tcttcccgca       60
c                                                                       61

```
<210> SEQ ID NO 20
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 20
ccgctcgagc tgaaaaacct tacaagtgtc c                              31

<210> SEQ ID NO 21
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 21
ggactagtcc tccagtatga gtacgttgat g                              31

<210> SEQ ID NO 22
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 22
acctgtgtgt gttcgctggt gacgttcaag atgagcacgc tgagaaaaag actttccaca    60

<210> SEQ ID NO 23
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 23
cccggtgtgg gtccgttggt gacgttcaag atgagcacgc tgactgaatg atttaccaca    60

<210> SEQ ID NO 24
<211> LENGTH: 61
<212> TYPE: DNA
<213> ORGANISM: Artificial sequence
<220> FEATURE:
<223> OTHER INFORMATION: Single strand DNA oligonucleotide

<400> SEQUENCE: 24
tccagtatga gtacgttgat gacgacgcaa atctccagac tgtgaaaaac tcttcccgca    60
c                                                                   61

<210> SEQ ID NO 25
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 25
acctgtgtgt gttcgctggt gacgaacaag atgtccagaa gtagaaaaag actttccaca    60

<210> SEQ ID NO 26
<211> LENGTH: 60
<212> TYPE: DNA
<213> ORGANISM: Artificial sequence
```

```
<220> FEATURE:
<223> OTHER INFORMATION: Single strand DNA oligonucleotide

<400> SEQUENCE: 26
cccggtgtgg gtccgttggt gacgaacaag atgtccagaa gtactgaatg atttaccaca      60

<210> SEQ ID NO 27
<211> LENGTH: 61
<212> TYPE: DNA
<213> ORGANISM: Artificial sequence
<220> FEATURE:
<223> OTHER INFORMATION: Single strand DNA oligonucleotide

<400> SEQUENCE: 27
tccagtatga gtacgttgat gacgaaccaa atttccagaa gttgaaaaac tcttcccgca      60
c                                                                     61

<210> SEQ ID NO 28
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 28
acctgtgtgt gttcgctggt gacgaaccaa attatcagaa cgagaaaaag actttccaca      60

<210> SEQ ID NO 29
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 29
cccggtgtgg gtccgttggt gagaagccaa atgtccagcc tgactgaatg atttaccaca      60

<210> SEQ ID NO 30
<211> LENGTH: 61
<212> TYPE: DNA
<213> ORGANISM: Artificial sequence
<220> FEATURE:
<223> OTHER INFORMATION: Single strand DNA oligonucleotide

<400> SEQUENCE: 30
tccagtatga gtacgttgat gacgaacaag atgtccagaa gttgaaaaac tcttcccgca      60
c                                                                     61

<210> SEQ ID NO 31
<211> LENGTH: 894
<212> TYPE: DNA
<213> ORGANISM: Artificial sequence
<220> FEATURE:
<223> OTHER INFORMATION: NLS-P1-25-ZFN1 expression cassette

<400> SEQUENCE: 31
atggtgccaa aaagaagag aaaggtagaa gaccctctc gagctgaaaa accttacaag       60
tgtcctgaat gtggaaagtc ttttctcag cgtgctcatc ttgaacgtca ccagcgaaca     120
cacacaggtg agaagccata taatgccca gaatgtggta atcattcag tcagcgtgct     180 catcttgaac gtcaccaacg gacccacacc ggggagaagc catttaaatg ccctgagtgc    240
gggaagagtt tttcacagtc tggagatttg cgtcgtcatc aacgtactca tactggagga    300
```

```
ctagtcaaaa gtgaactgga ggagaagaaa tctgaacttc gtcataaatt gaaatatgtg      360
cctcatgaat atattgaatt aattgaaatt gccagaaatt ccactcagga tagaattctt      420
gaaatgaagg taatggaatt ttttatgaaa gtttatggat atagaggtaa acatttgggt      480
ggatcaagga aaccggacgg agcaatttat actgtcggat ctcctattga ttacggtgtg      540
atcgtggata ctaaagctta tagcggaggt tataatctgc caattggcca agcagatgaa      600
atgcaacgat atgtcgaaga aaatcaaaca cgaaacaaac atatcaaccc taatgaatgg      660
tggaaagtct atccatcttc tgtaacggaa tttaagtttt tatttgtgag tggtcacttt      720
aaaggaaact acaaagctca gcttacacga ttaaatcata tcactaattg taatggagct      780
gttcttagtg tagaagagct tttaattggt ggagaaatga ttaaagccgg cacattaacc      840
ttagaggaag tgagacggaa atttaataac ggcgagataa actttggatc ctaa            894

<210> SEQ ID NO 32
<211> LENGTH: 894
<212> TYPE: DNA
<213> ORGANISM: Artificial sequence
<220> FEATURE:
<223> OTHER INFORMATION: NLS-P1-25-ZFN2 expression cassette

<400> SEQUENCE: 32
atggtgccaa aaagaagag aaaggtagaa gacccctctc gagctgaaaa accttacaag       60
tgtcctgaat gtggaaagtc ttttttctcag tctagcaacc tgcagaagca ccagcgaaca     120
cacacaggtg agaagccata taatgcccca gaatgtggta atcattcag tcgttctgat      180 aagttggttc gtcaccaacg gacccacacc ggggagaagc catttaaatg ccctgagtgc     240
gggaagagtt tttcacgttc tgataatttg gttcgtcatc aacgtactca tactggagga    300
ctagtcaaaa gtgaactgga ggagaagaaa tctgaacttc gtcataaatt gaaatatgtg      360
cctcatgaat atattgaatt aattgaaatt gccagaaatt ccactcagga tagaattctt      420
gaaatgaagg taatggaatt ttttatgaaa gtttatggat atagaggtaa acatttgggt      480
ggatcaagga aaccggacgg agcaatttat actgtcggat ctcctattga ttacggtgtg      540
atcgtggata ctaaagctta tagcggaggt tataatctgc caattggcca agcagatgaa      600
atgcaacgat atgtcgaaga aaatcaaaca cgaaacaaac atatcaaccc taatgaatgg      660
tggaaagtct atccatcttc tgtaacggaa tttaagtttt tatttgtgag tggtcacttt      720
aaaggaaact acaaagctca gcttacacga ttaaatcata tcactaattg taatggagct      780
gttcttagtg tagaagagct tttaattggt ggagaaatga ttaaagccgg cacattaacc      840
ttagaggaag tgagacggaa atttaataac ggcgagataa actttggatc ctaa            894

<210> SEQ ID NO 33
<211> LENGTH: 894
<212> TYPE: DNA
<213> ORGANISM: Artificial sequence
<220> FEATURE:
<223> OTHER INFORMATION: NLS-P1-36-ZFN1 expression cassette

<400> SEQUENCE: 33
atggtgccaa aaagaagag aaaggtagaa gacccctctc gagctgaaaa accttacaag       60
tgtcctgaat gtggaaagtc ttttttctact tctggacatc ttgttcgtca ccagcgaaca    120
cacacaggtg agaagccata taatgcccca gaatgtggta atcattcag tacttctgga     180 catcttgttc gtcaccaacg gacccacacc ggggagaagc catttaaatg ccctgagtgc     240
gggaagagtt tttcaacttc tggaaatttg gttcgtcatc aacgtactca tactggagga    300
```

```
ctagtcaaaa gtgaactgga ggagaagaaa tctgaacttc gtcataaatt gaaatatgtg    360
cctcatgaat atattgaatt aattgaaatt gccagaaatt ccactcagga tagaattctt    420
gaaatgaagg taatggaatt ttttatgaaa gtttatggat atagaggtaa acatttgggt    480
ggatcaagga aaccggacgg agcaatttat actgtcggat ctcctattga ttacggtgtg    540
atcgtggata ctaaagctta tagcggaggt tataatctgc caattggcca agcagatgaa    600
atgcaacgat atgtcgaaga aaatcaaaca cgaaacaaac atatcaaccc taatgaatgg    660
tggaaagtct atccatcttc tgtaacggaa tttaagtttt tatttgtgag tggtcacttt    720
aaaggaaact acaaagctca gcttacacga ttaaatcata tcactaattg taatggagct    780
gttcttagtg tagaagagct tttaattggt ggagaaatga ttaaagccgg cacattaacc    840
ttagaggaag tgagacggaa atttaataac ggcgagataa actttggatc ctaa           894
```

<210> SEQ ID NO 34
<211> LENGTH: 894
<212> TYPE: DNA
<213> ORGANISM: Artificial sequence
<220> FEATURE:
<223> OTHER INFORMATION: NLS-P1-36-ZFN2 expression cassette

<400> SEQUENCE: 34

```
atggtgccaa aaagaagag aaaggtagaa gaccccctctc gagctgaaaa accttacaag     60
tgtcctgaat gtggaaagtc ttttctcgt tctgataatt tggttcgtca ccagcgaaca    120
cacacaggtg agaagccata taatgccca gaatgtggta atcattcag tcaggctgga    180 catttggctt ctcaccaacg gacccacacc ggggagaagc catttaaatg ccctgagtgc    240
gggaagagtt tttcaacttc tggacatctt gttcgtcatc aacgtactca tactggagga    300
ctagtcaaaa gtgaactgga ggagaagaaa tctgaacttc gtcataaatt gaaatatgtg    360
cctcatgaat atattgaatt aattgaaatt gccagaaatt ccactcagga tagaattctt    420
gaaatgaagg taatggaatt ttttatgaaa gtttatggat atagaggtaa acatttgggt    480
ggatcaagga aaccggacgg agcaatttat actgtcggat ctcctattga ttacggtgtg    540
atcgtggata ctaaagctta tagcggaggt tataatctgc caattggcca agcagatgaa    600
atgcaacgat atgtcgaaga aaatcaaaca cgaaacaaac atatcaaccc taatgaatgg    660
tggaaagtct atccatcttc tgtaacggaa tttaagtttt tatttgtgag tggtcacttt    720
aaaggaaact acaaagctca gcttacacga ttaaatcata tcactaattg taatggagct    780
gttcttagtg tagaagagct tttaattggt ggagaaatga ttaaagccgg cacattaacc    840
ttagaggaag tgagacggaa atttaataac ggcgagataa actttggatc ctaa           894
```

<210> SEQ ID NO 35
<211> LENGTH: 297
<212> TYPE: PRT
<213> ORGANISM: Artificial sequence
<220> FEATURE:
<223> OTHER INFORMATION: NLS-P1-25-ZFN1 expressed polypeptide

<400> SEQUENCE: 35

Met Val Pro Lys Lys Arg Lys Val Glu Asp Pro Ser Arg Ala Glu
1               5                   10                  15

Lys Pro Tyr Lys Cys Pro Glu Cys Gly Lys Ser Phe Ser Gln Arg Ala
            20                  25                  30

His Leu Glu Arg His Gln Arg Thr His Thr Gly Glu Lys Pro Tyr Lys
        35                  40                  45

-continued

Cys Pro Glu Cys Gly Lys Ser Phe Ser Gln Arg Ala His Leu Glu Arg
 50                  55                  60

His Gln Arg Thr His Thr Gly Glu Lys Pro Phe Lys Cys Pro Glu Cys
 65                  70                  75                  80

Gly Lys Ser Phe Ser Gln Ser Gly Asp Leu Arg Arg His Gln Arg Thr
                 85                  90                  95

His Thr Gly Gly Leu Val Lys Ser Glu Leu Glu Glu Lys Lys Ser Glu
                100                 105                 110

Leu Arg His Lys Leu Lys Tyr Val Pro His Glu Tyr Ile Glu Leu Ile
            115                 120                 125

Glu Ile Ala Arg Asn Ser Thr Gln Asp Arg Ile Leu Glu Met Lys Val
        130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
                180                 185                 190

Leu Pro Ile Gly Gln Ala Asp Glu Met Gln Arg Tyr Val Glu Glu Asn
            195                 200                 205

Gln Thr Arg Asn Lys His Ile Asn Pro Asn Glu Trp Trp Lys Val Tyr
        210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
                260                 265                 270

Met Ile Lys Ala Gly Thr Leu Thr Leu Glu Glu Val Arg Arg Lys Phe
            275                 280                 285

Asn Asn Gly Glu Ile Asn Phe Gly Ser
        290                 295

<210> SEQ ID NO 36
<211> LENGTH: 297
<212> TYPE: PRT
<213> ORGANISM: Artificial sequence
<220> FEATURE:
<223> OTHER INFORMATION: NLS-P1-25-ZFN2 expressed polypeptide

<400> SEQUENCE: 36

Met Val Pro Lys Lys Lys Arg Lys Val Glu Asp Pro Ser Arg Ala Glu
 1                   5                  10                  15

Lys Pro Tyr Lys Cys Pro Glu Cys Gly Lys Ser Phe Ser Gln Ser Ser
                 20                  25                  30

Asn Leu Gln Lys His Gln Arg Thr His Thr Gly Glu Lys Pro Tyr Lys
             35                  40                  45

Cys Pro Glu Cys Gly Lys Ser Phe Ser Arg Ser Asp Lys Leu Val Arg
 50                  55                  60

His Gln Arg Thr His Thr Gly Glu Lys Pro Phe Lys Cys Pro Glu Cys
 65                  70                  75                  80

Gly Lys Ser Phe Ser Arg Ser Asp Asn Leu Val Arg His Gln Arg Thr
                 85                  90                  95

His Thr Gly Gly Leu Val Lys Ser Glu Leu Glu Glu Lys Lys Ser Glu
                100                 105                 110

Leu Arg His Lys Leu Lys Tyr Val Pro His Glu Tyr Ile Glu Leu Ile
            115                 120                 125

Glu Ile Ala Arg Asn Ser Thr Gln Asp Arg Ile Leu Glu Met Lys Val
        130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser
    290                 295

<210> SEQ ID NO 37
<211> LENGTH: 297
<212> TYPE: PRT
<213> ORGANISM: Artificial sequence
<220> FEATURE:
<223> OTHER INFORMATION: NLS-P1-36-ZFN1 expressed polypeptide

<400> SEQUENCE: 37

Met Val Pro Lys Lys Lys Arg Lys Val Glu Asp Pro Ser Arg Ala Glu
1               5                   10                  15

Lys Pro Tyr Lys Cys Pro Glu Cys Gly Lys Ser Phe Ser Thr Ser Gly
            20                  25                  30

His Leu Val Arg His Gln Arg Thr His Thr Gly Glu Lys Pro Tyr Lys
        35                  40                  45

Cys Pro Glu Cys Gly Lys Ser Phe Ser Thr Ser Gly His Leu Val Arg
    50                  55                  60

His Gln Arg Thr His Thr Gly Glu Lys Pro Phe Lys Cys Pro Glu Cys
65                  70                  75                  80

Gly Lys Ser Phe Ser Thr Ser Gly Asn Leu Val Arg His Gln Arg Thr
                85                  90                  95

His Thr Gly Gly Leu Val Lys Ser Glu Leu Glu Glu Lys Lys Ser Glu
            100                 105                 110

Leu Arg His Lys Leu Lys Tyr Val Pro His Glu Tyr Ile Glu Leu Ile
        115                 120                 125

Glu Ile Ala Arg Asn Ser Thr Gln Asp Arg Ile Leu Glu Met Lys Val
    130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

```
Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser
    290                 295

<210> SEQ ID NO 38
<211> LENGTH: 297
<212> TYPE: PRT
<213> ORGANISM: Artificial sequence
<220> FEATURE:
<223> OTHER INFORMATION: NLS-P1-36-ZFN2 expressed polypeptide

<400> SEQUENCE: 38

Met Val Pro Lys Lys Lys Arg Lys Val Glu Asp Pro Ser Arg Ala Glu
1               5                   10                  15

Lys Pro Tyr Lys Cys Pro Glu Cys Gly Lys Ser Phe Ser Arg Ser Asp
            20                  25                  30

Asn Leu Val Arg His Gln Arg Thr His Thr Gly Glu Lys Pro Tyr Lys
        35                  40                  45

Cys Pro Glu Cys Gly Lys Ser Phe Ser Gln Ala Gly His Leu Ala Ser
    50                  55                  60

His Gln Arg Thr His Thr Gly Glu Lys Pro Phe Lys Cys Pro Glu Cys
65                  70                  75                  80

Gly Lys Ser Phe Ser Thr Ser Gly His Leu Val Arg His Gln Arg Thr
                85                  90                  95

His Thr Gly Gly Leu Val Lys Ser Glu Leu Glu Glu Lys Lys Ser Glu
            100                 105                 110

Leu Arg His Lys Leu Lys Tyr Val Pro His Glu Tyr Ile Glu Leu Ile
        115                 120                 125

Glu Ile Ala Arg Asn Ser Thr Gln Asp Arg Ile Leu Glu Met Lys Val
    130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240
```

Lys Gly Asn Tyr Lys Ala Gln Leu Thr Arg Leu Asn His Ile Thr Asn
            245                 250                 255

Cys Asn Gly Ala Val Leu Ser Val Glu Leu Leu Ile Gly Gly Glu
        260                 265                 270

Met Ile Lys Ala Gly Thr Leu Thr Leu Glu Glu Val Arg Arg Lys Phe
    275                 280                 285

Asn Asn Gly Glu Ile Asn Phe Gly Ser
    290                 295

<210> SEQ ID NO 39
<211> LENGTH: 65
<212> TYPE: DNA
<213> ORGANISM: Artificial sequence
<220> FEATURE:
<223> OTHER INFORMATION: pET28 vector MCS

<400> SEQUENCE: 39
tcggatccga attcgagctc cgtcgacaag cttgcggccg cactcgagca ccaccaccac     60
cacca                                                                65

<210> SEQ ID NO 40
<211> LENGTH: 54
<212> TYPE: DNA
<213> ORGANISM: Artificial sequence
<220> FEATURE:
<223> OTHER INFORMATION: Thosea asigna insect virus derived T2A
      nucleotide sequence

<400> SEQUENCE: 40
gaaggaagag gatctcttct tacttgtggt gatgttgaag agaatcctgg acca           54

<210> SEQ ID NO 41
<211> LENGTH: 18
<212> TYPE: PRT
<213> ORGANISM: Artificial sequence
<220> FEATURE:
<223> OTHER INFORMATION: Thosea asigna insect virus derived T2A
      polypeptide

<400> SEQUENCE: 41

Glu Gly Arg Gly Ser Leu Leu Thr Cys Gly Asp Val Glu Glu Asn Pro
1               5                   10                  15

Gly Pro

<210> SEQ ID NO 42
<211> LENGTH: 9
<212> TYPE: DNA
<213> ORGANISM: Artificial sequence
<220> FEATURE:
<223> OTHER INFORMATION: Zinc finger target sequence

<400> SEQUENCE: 42 ggggaagaa                                                             9

<210> SEQ ID NO 43
<211> LENGTH: 1065
<212> TYPE: DNA
<213> ORGANISM: Artificial sequence
<220> FEATURE:
<223> OTHER INFORMATION: Tobacco rattle virus gene for coat protein 2b

<400> SEQUENCE: 43
atgcacgaat tacttaggaa gtggcttgac gacactaatg tgttattgtt agataatggt     60

```
ttggtggtca aggtacgtag tagagtccca catattcgca cgtatgaagt aattggaaag      120
ttgtcagttt ttgataattc actgggagat gatacgctgt tgagggaaa agtagagaac       180 gtatttgttt ttatgttcag gcggttcttg tgtgtcaaca agatggaca ttgttactca       240 aggaagcacg atgagcttta ttattacgga cgagtggact tagattctgt gagtaaggtt     300
acctcagggt acgagaaact ctttattcac agagaacttt atatcttaac agatttaatt    360
gagagagtga gtaagttctt taacttagct caggatgtgg tagaagcaag ttttgagtat    420
gccaaggttg aagagaggtt aggtcacgtc agaaacgtgt tgcaactggc gggtggaaaa    480
tccacgaatg ccgatttgac aattaagatt tctgacgatg tcgaacaact gcttggaaaa    540
cgtggtggat tcttgaaggt tgtgaacggt atcttgagca agaatggtag tgacgtagtc    600
actaacgaca atgagcttat tcatgcaatt aaccaaaatc tggtaccaga taaagtcatg    660
tctgtgtcga acgtaatgaa agagactggg tttctgcagt ttccaaagtt tttatctaag    720
ttggaaggac aggtaccgaa aggaacaaaa tttctagaca aacacgttcc tgattttact    780
tggatacaag ctcttgaaga aagagtgaat attcggagag agaatcggg acttcagact     840 ctattagctg atatcgttcc gaggaatgct attgctgctc agaaattgac aatgctaggt   900
tacatcgagt atcacgacta tgtggtgatc gtctgtcagt ctggagtatt tagtgacgat   960
tgggcgacat gtagaatgct ttgggcagca ctatctagtg ctcaactata tacctatgtt  1020
gacgccagta gaatcggtcc aatcgtttac ggttggttat tgtga                   1065

<210> SEQ ID NO 44
<211> LENGTH: 70
<212> TYPE: DNA
<213> ORGANISM: Artificial sequence
<220> FEATURE:
<223> OTHER INFORMATION: TMV derived Omega translational enhancer

<400> SEQUENCE: 44
gtatttttac aacaattacc aacaacaaca acaacagac aacattacaa ttactattta       60
caattacaat                                                             70

<210> SEQ ID NO 45
<211> LENGTH: 188
<212> TYPE: DNA
<213> ORGANISM: Artificial sequence
<220> FEATURE:
<223> OTHER INFORMATION: sgP-CP-PEBV sequence

<400> SEQUENCE: 45
gagcatcttg ttctgggggtt tcacactatc tttagagaaa gtgttaagtt aattaagtta      60
tcttaattaa gagcataatt atactgatttt gtctctcgtt gatagagtct atcattctgt    120
tactaaaaat ttgacaactc ggtttgctga cctactggtt actgtatcac ttacccgagt    180
taacgaga                                                             188

<210> SEQ ID NO 46
<211> LENGTH: 30
<212> TYPE: DNA
<213> ORGANISM: Artificial sequence
<220> FEATURE:
<223> OTHER INFORMATION: Nuclear localization signal (NLS)

<400> SEQUENCE: 46
ccaaaaaaga agagaaaggt agaagacccc                                       30
```

<210> SEQ ID NO 47
<211> LENGTH: 131
<212> TYPE: DNA
<213> ORGANISM: Artificial sequence
<220> FEATURE:
<223> OTHER INFORMATION: Tobacco etch virus derived 5'-UTR Omega
      translational enhancer

<400> SEQUENCE: 47
tctcaacaca acatatacaa aacaaacgaa tctcaagcaa tcaagcattc tacttctatt     60
gcagcaattt aaatcatttc ttttaaagca aaagcaattt tctgaaaatt ttcaccattt    120
acgaacgata g                                                         131

<210> SEQ ID NO 48
<211> LENGTH: 168
<212> TYPE: DNA
<213> ORGANISM: Artificial sequence
<220> FEATURE:
<223> OTHER INFORMATION: sgP-2b-TRV2 sequence

<400> SEQUENCE: 48
ggatttaagg acgtgaactc tgttgagatc tctgtgaaat tcagagggtg ggtgatacca     60
tattcactga tgccattagc gacatctaaa tagggctaat tgtgactaat tgagggaat    120 ttcctttacc attgacgtca gtgtcgttgg tagcatttga gtttcgca                 168

<210> SEQ ID NO 49
<211> LENGTH: 44
<212> TYPE: DNA
<213> ORGANISM: Artificial sequence
<220> FEATURE:
<223> OTHER INFORMATION: pET28c.SX vector modified MCS

<400> SEQUENCE: 49
tcggatccga attcgagctc cgtcgagcac caccaccacc acca                      44

<210> SEQ ID NO 50
<211> LENGTH: 300
<212> TYPE: DNA
<213> ORGANISM: Artificial sequence
<220> FEATURE:
<223> OTHER INFORMATION: Viral helper protein encoded by the RNA2-2b
      gene

<400> SEQUENCE: 50
atgcacgaat tacttaggaa gtggcttgac gacactaatg tgttattgtt agataatggt     60
ttggtggtca aggtacgtag tagagtccca catattcgca cgtatgaagt aattggaaag    120
ttgtcagttt ttgataattc actgggagat gatacgctgt tgagggaaa agtagagaac    180 gtatttgttt ttatgttcag gcggttcttg tgtgtcaaca aagatggaca ttgttactca    240
aggaagcacg atgagcttta ttattacgga cgagtggact tagattctgt gagtaaggtt    300

<210> SEQ ID NO 51
<211> LENGTH: 54
<212> TYPE: DNA
<213> ORGANISM: Thosea asigna virus
<220> FEATURE:
<221> NAME/KEY: misc_feature
<223> OTHER INFORMATION: Tav-T2A

<400> SEQUENCE: 51
gagggcaggg gaagtcttct aacatgcggg gacgtggagg aaaatcccgg cccc           54

<210> SEQ ID NO 52
<211> LENGTH: 54
<212> TYPE: DNA
<213> ORGANISM: Artificial sequence
<220> FEATURE:
<223> OTHER INFORMATION: Modified Tav-T2A sequence according to the
      codon usage of Petunia

<400> SEQUENCE: 52
gaaggaagag gatctcttct tacttgtggt gatgttgaag agaatcctgg acca                54

<210> SEQ ID NO 53
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 53
agttaacgag atggcctcct ccgaga                                               26

<210> SEQ ID NO 54
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 54
tagagctctc acaggaacag gtggtggc                                             28

<210> SEQ ID NO 55
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 55
tttggatccg aaggaagagg atctcttctt acttgtggtg atgttgaaga g                   51

<210> SEQ ID NO 56
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 56
ttacttgtgg tgatgttgaa gagaatcctg gaccaaaaaa gaagagaaag                     50

<210> SEQ ID NO 57
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 57
aagagctctt aggatccaaa gtttatctc                                            29

<210> SEQ ID NO 58
<211> LENGTH: 24
<212> TYPE: DNA
<213> ORGANISM: Artificial sequence
<220> FEATURE:

<223> OTHER INFORMATION: Single strand DNA oligonucleotide

<400> SEQUENCE: 58
aggatcccag gaacaggtgg tggc                                      24

<210> SEQ ID NO 59
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 59
atctcgagtg agcaagggcg a                                         21

<210> SEQ ID NO 60
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 60
agagctctac ttgtacagct cgtccatg                                  28

<210> SEQ ID NO 61
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 61
atggtgccaa aaagaagag aaaggtagaa gaccctctc gag                   43

<210> SEQ ID NO 62
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 62
cccgggattt aaggacgtga actctgt                                   27

<210> SEQ ID NO 63
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 63
cccgggtcac aggaacaggt ggt                                       23

<210> SEQ ID NO 64
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 64
agttaacgag atgccaaaaa agaagagaaa ggt                            33

```
<210> SEQ ID NO 65
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 65
aagagctctt aagatccaaa gtttatctc                                    29

<210> SEQ ID NO 66
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 66
acccgggtta tccaaagttt atctcgccgt                                   30

<210> SEQ ID NO 67
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 67
aactcgagaa aaactgcgga acgga                                        25

<210> SEQ ID NO 68
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 68
agttaacgag atggcttcta tgatatcctc t                                 31

<210> SEQ ID NO 69
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 69
agttaacgag atggcttctc ggagg                                        25

<210> SEQ ID NO 70
<211> LENGTH: 894
<212> TYPE: DNA
<213> ORGANISM: Artificial sequence
<220> FEATURE:
<223> OTHER INFORMATION: PDS-ZFN1 polynucleotide sequence

<400> SEQUENCE: 70
atggtgccaa aaagaagag aaaggtagaa gaccctctc gagctgaaaa accttacaag    60
tgtcctgaat gtggaaagtc tttttctcag tctggagatt gcgtcgtca ccagcgaaca   120 cacacaggtg agaagccata taatgccca gaatgtggta atcattcag tacttctgga   180 aatttggttc gtcaccaacg gacccacacc ggggagaagc catttaaatg ccctgagtgc  240
gggaagagtt tttcacagcg cgcgcatctg gaacgccatc aacgtactca tactggagga  300
```

-continued

```
ctagtcaaaa gtgaactgga ggagaagaaa tctgaacttc gtcataaatt gaaatatgtg    360
cctcatgaat atattgaatt aattgaaatt gccagaaatt ccactcagga tagaattctt    420
gaaatgaagg taatggaatt ttttatgaaa gtttatggat atagaggtaa acatttgggt    480
ggatcaagga aaccggacgg agcaatttat actgtcggat ctcctattga ttacggtgtg    540
atcgtggata ctaaagctta tagcggaggt tataatctgc caattggcca agcagatgaa    600
atgcaacgat atgtcgaaga aaatcaaaca cgaaacaaac atatcaaccc taatgaatgg    660
tggaaagtct atccatcttc tgtaacggaa tttaagtttt tatttgtgag tggtcacttt    720
aaaggaaact acaaagctca gcttacacga ttaaatcata tcactaattg taatggagct    780
gttcttagtg tagaagagct tttaattggt ggagaaatga ttaaagccgg cacattaacc    840
ttagaggaag tgagacggaa atttaataac ggcgagataa actttggatc ctaa          894
```

<210> SEQ ID NO 71
<211> LENGTH: 297
<212> TYPE: PRT
<213> ORGANISM: Artificial sequence
<220> FEATURE:
<223> OTHER INFORMATION: PDS-ZFN1 polypeptide sequence

<400> SEQUENCE: 71

```
Met Val Pro Lys Lys Lys Arg Lys Val Glu Asp Pro Ser Arg Ala Glu
1               5                   10                  15

Lys Pro Tyr Lys Cys Pro Glu Cys Gly Lys Ser Phe Ser Gln Ser Gly
            20                  25                  30

Asp Leu Arg Arg His Gln Arg Thr His Thr Gly Glu Lys Pro Tyr Lys
        35                  40                  45

Cys Pro Glu Cys Gly Lys Ser Phe Ser Thr Ser Gly Asn Leu Val Arg
    50                  55                  60

His Gln Arg Thr His Thr Gly Glu Lys Pro Phe Lys Cys Pro Glu Cys
65                  70                  75                  80

Gly Lys Ser Phe Ser Gln Arg Ala His Leu Glu Arg His Gln Arg Thr
                85                  90                  95

His Thr Gly Gly Leu Val Lys Ser Glu Leu Glu Glu Lys Lys Ser Glu
            100                 105                 110

Leu Arg His Lys Leu Lys Tyr Val Pro His Glu Tyr Ile Glu Leu Ile
        115                 120                 125

Glu Ile Ala Arg Asn Ser Thr Gln Asp Arg Ile Leu Glu Met Lys Val
    130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
```

```
               260                 265                 270
Met Ile Lys Ala Gly Thr Leu Thr Leu Glu Glu Val Arg Arg Lys Phe
               275                 280                 285

Asn Asn Gly Glu Ile Asn Phe Gly Ser
               290                 295

<210> SEQ ID NO 72
<211> LENGTH: 894
<212> TYPE: DNA
<213> ORGANISM: Artificial sequence
<220> FEATURE:
<223> OTHER INFORMATION: PDS-ZFN2 polynucleotide sequence

<400> SEQUENCE: 72
atggtgccaa aaagaagag aaaggtagaa gacccctctc gagctgaaaa accttacaag     60
tgtcctgaat gtggaaagtc tttttctcgc agcgatgaac tggtgcgcca ccagcgaaca   120
cacacaggtg agaagccata taatgccca gaatgtggta aatcattcag tcagtctagc    180
aacctggtta gacaccaacg gacccacacc ggggagaagc catttaaatg ccctgagtgc   240
gggaagagtt tttcacataa aaacgcgctg cagaaccatc aacgtactca tactggagga   300
ctagtcaaaa gtgaactgga ggagaagaaa tctgaacttc gtcataaatt gaaatatgtg   360
cctcatgaat atattgaatt aattgaaatt gccagaaatt ccactcagga tagaattctt   420
gaaatgaagg taatggaatt ttttatgaaa gtttatggat atagaggtaa acatttgggt   480
ggatcaagga aaccggacgg agcaatttat actgtcggat ctcctattga ttacggtgtg   540
atcgtggata ctaaagctta tagcggaggt tataatctgc caattggcca agcagatgaa   600
atgcaacgat atgtcgaaga aaatcaaaca cgaaacaaac atatcaaccc taatgaatgg   660
tggaaagtct atccatcttc tgtaacggaa tttaagtttt tatttgtgag tggtcacttt   720
aaaggaaact acaaagctca gcttacacga ttaaatcata tcactaattg taatggagct   780
gttcttagtg tagaagagct tttaattggt ggagaaatga ttaaagccgg cacattaacc   840
ttagaggaag tgagacggaa atttaataac ggcgagataa actttggatc ctaa         894

<210> SEQ ID NO 73
<211> LENGTH: 297
<212> TYPE: PRT
<213> ORGANISM: Artificial sequence
<220> FEATURE:
<223> OTHER INFORMATION: PDS-ZFN2 polypeptide sequence

<400> SEQUENCE: 73

Met Val Pro Lys Lys Arg Lys Val Glu Asp Pro Ser Arg Ala Glu
1               5                   10                  15

Lys Pro Tyr Lys Cys Pro Glu Cys Gly Lys Ser Phe Ser Arg Ser Asp
                20                  25                  30

Glu Leu Val Arg His Gln Arg Thr His Thr Gly Glu Lys Pro Tyr Lys
            35                  40                  45

Cys Pro Glu Cys Gly Lys Ser Phe Ser Gln Ser Ser Asn Leu Val Arg
        50                  55                  60

His Gln Arg Thr His Thr Gly Glu Lys Pro Phe Lys Cys Pro Glu Cys
65                  70                  75                  80

Gly Lys Ser Phe Ser His Lys Asn Ala Leu Gln Asn His Gln Arg Thr
                85                  90                  95

His Thr Gly Gly Leu Val Lys Ser Glu Leu Glu Glu Lys Lys Ser Glu
            100                 105                 110
```

Leu Arg His Lys Leu Lys Tyr Val Pro His Glu Tyr Ile Glu Leu Ile
            115                 120                 125

Glu Ile Ala Arg Asn Ser Thr Gln Asp Arg Ile Leu Glu Met Lys Val
        130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser
        290                 295

<210> SEQ ID NO 74
<211> LENGTH: 894
<212> TYPE: DNA
<213> ORGANISM: Artificial sequence
<220> FEATURE:
<223> OTHER INFORMATION: FHT-ZFN1 polynucleotide sequence

<400> SEQUENCE: 74
atggtgccaa aaagaagag aaaggtagaa gacccctctc gagctgaaaa accttacaag      60
tgtcctgaat gtggaaagtc tttttctact tctggagaat tggttcgtca ccagcgaaca    120
cacacaggtg agaagccata taatgccca gaatgtggta atcattcag tacttctgga     180 catcttgttc gtcaccaacg gacccacacc ggggagaagc catttaaatg ccctgagtgc    240
gggaagagtt tttcacagag cagcaacctg gtgcgccatc aacgtactca tactggagga    300
ctagtcaaaa gtgaactgga ggagaagaaa tctgaacttc gtcataaatt gaaatatgtg    360
cctcatgaat atattgaatt aattgaaatt gccagaaatt ccactcagga tagaattctt    420
gaaatgaagg taatggaatt tttttatgaaa gtttatggat atagaggtaa acatttgggt    480
ggatcaagga aaccggacgg agcaatttat actgtcggat ctcctattga ttacggtgtg    540
atcgtggata ctaaagctta tagcggaggt tataatctgc caattggcca agcagatgaa    600
atgcaacgat atgtcgaaga aaatcaaaca cgaaacaaac atatcaaccc taatgaatgg    660
tggaaagtct atccatcttc tgtaacggaa tttaagtttt tatttgtgag tggtcacttt    720
aaaggaaact acaaagctca gcttacacga ttaaatcata tcactaattg taatggagct    780
gttcttagtg tagaagagct tttaattggt ggagaaatga ttaaagccgg cacattaacc    840
ttagaggaag tgagacggaa atttaataac ggcgagataa actttggatc ctaa          894

<210> SEQ ID NO 75
<211> LENGTH: 297

<212> TYPE: PRT
<213> ORGANISM: Artificial sequence
<220> FEATURE:
<223> OTHER INFORMATION: FHT-ZFN1 polypeptide sequence

<400> SEQUENCE: 75

Met Val Pro Lys Lys Arg Lys Val Glu Asp Pro Ser Arg Ala Glu
1               5                   10                  15

Lys Pro Tyr Lys Cys Pro Glu Cys Gly Lys Ser Phe Ser Thr Ser Gly
            20                  25                  30

Glu Leu Val Arg His Gln Arg Thr His Thr Gly Glu Lys Pro Tyr Lys
        35                  40                  45

Cys Pro Glu Cys Gly Lys Ser Phe Ser Thr Ser Gly His Leu Val Arg
    50                  55                  60

His Gln Arg Thr His Thr Gly Glu Lys Pro Phe Lys Cys Pro Glu Cys
65                  70                  75                  80

Gly Lys Ser Phe Ser Gln Ser Ser Asn Leu Val Arg His Gln Arg Thr
                85                  90                  95

His Thr Gly Gly Leu Val Lys Ser Glu Leu Glu Lys Lys Ser Glu
            100                 105                 110

Leu Arg His Lys Leu Lys Tyr Val Pro His Glu Tyr Ile Glu Leu Ile
        115                 120                 125

Glu Ile Ala Arg Asn Ser Thr Gln Asp Arg Ile Leu Glu Met Lys Val
    130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser
    290                 295

<210> SEQ ID NO 76
<211> LENGTH: 894
<212> TYPE: DNA
<213> ORGANISM: Artificial sequence
<220> FEATURE:
<223> OTHER INFORMATION: FHT-ZFN2 polynucleotide sequence

<400> SEQUENCE: 76
atggtgccaa aaagaagag aaaggtagaa gaccccctctc gagctgaaaa accttacaag    60
tgtcctgaat gtggaaagtc ttttctctcgc gcggataacc tgaccgaaca ccagcgaaca   120
cacacaggtg agaagccata taatgcccca gaatgtggta atcattcag tcagtctagc    180

-continued

```
aacctggtta gacaccaacg gacccacacc ggggagaagc catttaaatg ccctgagtgc      240
gggaagagtt tttcaacttc tggagaattg gttcgtcatc aacgtactca tactggagga      300
ctagtcaaaa gtgaactgga ggagaagaaa tctgaacttc gtcataaatt gaaatatgtg      360
cctcatgaat atattgaatt aattgaaatt gccagaaatt ccactcagga tagaattctt      420
gaaatgaagg taatggaatt ttttatgaaa gtttatggat atagaggtaa acatttgggt      480
ggatcaagga aaccggacgg agcaatttat actgtcggat ctcctattga ttacggtgtg      540
atcgtggata ctaaagctta tagcggaggt tataatctgc caattggcca agcagatgaa      600
atgcaacgat atgtcgaaga aaatcaaaca cgaaacaaac atatcaaccc taatgaatgg      660
tggaaagtct atccatcttc tgtaacggaa tttaagtttt tatttgtgag tggtcacttt      720
aaaggaaact acaaagctca gcttacacga ttaaatcata tcactaattg taatggagct      780
gttcttagtg tagaagagct tttaattggt ggagaaatga ttaaagccgg cacattaacc      840
ttagaggaag tgagacggaa atttaataac ggcgagataa actttggatc ctaa            894
```

```
<210> SEQ ID NO 77
<211> LENGTH: 297
<212> TYPE: PRT
<213> ORGANISM: Artificial sequence
<220> FEATURE:
<223> OTHER INFORMATION: FHT-ZFN2 polypeptide sequence

<400> SEQUENCE: 77
```

```
Met Val Pro Lys Lys Arg Lys Val Glu Asp Pro Ser Arg Ala Glu
1               5                  10                  15

Lys Pro Tyr Lys Cys Pro Glu Cys Gly Lys Ser Phe Ser Arg Ala Asp
            20                  25                  30

Asn Leu Thr Glu His Gln Arg Thr His Thr Gly Glu Lys Pro Tyr Lys
        35                  40                  45

Cys Pro Glu Cys Gly Lys Ser Phe Ser Gln Ser Ser Asn Leu Val Arg
    50                  55                  60

His Gln Arg Thr His Thr Gly Glu Lys Pro Phe Lys Cys Pro Glu Cys
65                  70                  75                  80

Gly Lys Ser Phe Ser Thr Ser Gly Glu Leu Val Arg His Gln Arg Thr
                85                  90                  95

His Thr Gly Gly Leu Val Lys Ser Glu Leu Glu Glu Lys Lys Ser Glu
            100                 105                 110

Leu Arg His Lys Leu Lys Tyr Val Pro His Glu Tyr Ile Glu Leu Ile
        115                 120                 125

Glu Ile Ala Arg Asn Ser Thr Gln Asp Arg Ile Leu Glu Met Lys Val
    130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240
```

```
Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser
        290                 295
```

<210> SEQ ID NO 78
<211> LENGTH: 420
<212> TYPE: DNA
<213> ORGANISM: Artificial sequence
<220> FEATURE:
<223> OTHER INFORMATION: Sequence lacking 40 nucleotides from 2b-sgP
      (pTRV2- 2b-2bsgP-sgP)

<400> SEQUENCE: 78
cagctgctag ttcatctgca ccgcctccag cgagtggagg tccgatacgt cctaatccct     60
agggatttaa ggacgtgaac tctgttgaga tctctgtgaa attcagaggg tgggtgatac    120
catattcact gatgccatta gcgacatcta aatagggcta attgtgacta atttgaggga    180
atttccttta ccattctaga aggcctccat ggggatccgg taccgagctc gagcatcttg    240
ttctggggtt tcacactatc tttagagaaa gtgttaagtt aattaagtta tcttaattaa    300
gagcataatt atactgattt gtctctcgtt gatagagtct atcattctgt tactaaaaat    360
ttgacaactc ggtttgctga cctactggtt actgtatcac ttacccgagt tgttaacgag    420

<210> SEQ ID NO 79
<211> LENGTH: 469
<212> TYPE: DNA
<213> ORGANISM: Artificial sequence
<220> FEATURE:
<223> OTHER INFORMATION: Sequence of pTRV2 containing 2b and PEBV
      subgenomic promoters (sgP) region

<400> SEQUENCE: 79
tttggtggag cagctgctag ttcatctgca ccgcctccag cgagtggagg tccgatacgt     60
cctaatccct agggatttaa ggacgtgaac tctgttgaga tctctgtgaa attcagaggg    120
tgggtgatac catattcact gatgccatta gcgacatcta aatagggcta attgtgacta    180
atttgaggga atttccttta ccattgacgt cagtgtcgtt ggtagcattt gagtttcgaa    240
ttctctagaa ggcctccatg gggatccggt accgagctcg agcatcttgt tctggggttt    300
cacactatct ttagagaaag tgttaagtta attaagttat cttaattaag agcataatta    360
tactgatttg tctctcgttg atagagtcta tcattctgtt actaaaaatt tgacaactcg    420
gtttgctgac ctactggtta ctgtatcact tacccgagtt gttaacgag                469

<210> SEQ ID NO 80
<211> LENGTH: 420
<212> TYPE: DNA
<213> ORGANISM: Artificial sequence
<220> FEATURE:
<223> OTHER INFORMATION: Consensus Sequence of comparison between
      Sequence lacking 40 nucleotides from 2b-sgP and pTRV2 containing
      2b and PEBV subgenomic promoters (sgP) region

<400> SEQUENCE: 80
cagctgctag ttcatctgca ccgcctccag cgagtggagg tccgatacgt cctaatccct     60

-continued

| | |
|---|---|
| agggatttaa ggacgtgaac tctgttgaga tctctgtgaa attcagaggg tgggtgatac | 120 |
| catattcact gatgccatta gcgacatcta aatagggcta attgtgacta atttgaggga | 180 |
| atttccttta ccattctaga aggcctccat ggggatccgg taccgagctc gagcatcttg | 240 |
| ttctggggtt tcacactatc tttagagaaa gtgttaagtt aattaagtta tcttaattaa | 300 |
| gagcataatt atactgattt gtctctcgtt gatagagtct atcattctgt tactaaaaat | 360 |
| ttgacaactc ggtttgctga cctactggtt actgtatcac ttacccgagt tgttaacgag | 420 |

<210> SEQ ID NO 81
<211> LENGTH: 54
<212> TYPE: DNA
<213> ORGANISM: Thosea asigna virus
<220> FEATURE:
<221> NAME/KEY: misc_feature
<223> OTHER INFORMATION: A 2A-like 54 nucleotide sequence

<400> SEQUENCE: 81
gagggcaggg gaagtcttct aacatgcggg gacgtggagg aaaatcccgg cccc    54

<210> SEQ ID NO 82
<211> LENGTH: 933
<212> TYPE: DNA
<213> ORGANISM: Artificial sequence
<220> FEATURE:
<223> OTHER INFORMATION: NLS-QEQ-ZFN nucleic acid sequence

<400> SEQUENCE: 82

| | |
|---|---|
| atggtgccaa aaagaagag aaaggtagaa gacccctctc gagaaaaact gcggaacgga | 60 |
| tccggggacc ctggcaaaaa gaaacagcac gcgtgtccgg aatgcggcaa gtcctttagt | 120 |
| cagtctagca acctgcagaa gcatcaacgt acgcataccg gggaaaaacc ttacaaatgt | 180 |
| ccggaatgcg gcaagtcctt tagtcagtct agcaacctgc agaagcatca acgtacgcat | 240 |
| accggggaaa aaccttacaa atgtccggaa tgcggcaaga gctttagtag aagtgatcat | 300 |
| ctgtcaagac atcaacgtac gcatcagaat aagaagcaac tagtcaaaag tgaactggag | 360 |
| gagaagaaat ctgaacttcg tcataaattg aaatatgtgc tcatgaata tattgaatta | 420 |
| attgaaattg ccagaaattc cactcaggat agaattcttg aaatgaaggt aatggaattt | 480 |
| tttatgaaag tttatggata tagaggtaaa catttgggtg gatcaaggaa accggacgga | 540 |
| gcaatttata ctgtcggatc tcctattgat tacggtgtga tcgtggatac taaagcttat | 600 |
| agcggaggtt ataatctgcc aattggccaa gcagatgaaa tgcaacgata tgtcgaagaa | 660 |
| aatcaaacac gaaacaaaca tatcaaccct aatgaatggt ggaaagtcta tccatcttct | 720 |
| gtaacggaat ttaagttttt atttgtgagt ggtcacttta aggaaaacta caaagctcag | 780 |
| cttacacgat taaatcatat cactaattgt aatggagctg ttcttagtgt agaagagctt | 840 |
| ttaattggtg gagaaatgat taaagccggc acattaacct tagaggaagt gagacggaaa | 900 |
| tttaataacg gcgagataaa ctttggatct taa | 933 |

<210> SEQ ID NO 83
<211> LENGTH: 310
<212> TYPE: PRT
<213> ORGANISM: Artificial sequence
<220> FEATURE:
<223> OTHER INFORMATION: NLS-QEQ-ZFN polypeptide sequence

<400> SEQUENCE: 83

Met Val Pro Lys Lys Lys Arg Lys Val Glu Asp Pro Ser Arg Glu Lys
1               5                   10                  15

```
Leu Arg Asn Gly Ser Gly Asp Pro Gly Lys Lys Gln His Ala Cys
            20                  25                  30

Pro Glu Cys Gly Lys Ser Phe Ser Gln Ser Ser Asn Leu Gln Lys His
        35                  40                  45

Gln Arg Thr His Thr Gly Glu Lys Pro Tyr Lys Cys Pro Glu Cys Gly
    50                  55                  60

Lys Ser Phe Ser Gln Ser Ser Asn Leu Gln Lys His Gln Arg Thr His
65                  70                  75                  80

Thr Gly Glu Lys Pro Tyr Lys Cys Pro Glu Cys Gly Lys Ser Phe Ser
                85                  90                  95

Arg Ser Asp His Leu Ser Arg His Gln Arg Thr His Asn Lys Lys
            100                 105                 110

Gln Leu Val Lys Ser Glu Leu Glu Lys Lys Ser Glu Leu Arg His
        115                 120                 125

Lys Leu Lys Tyr Val Pro His Glu Tyr Ile Glu Leu Glu Ile Ala
130                 135                 140

Arg Asn Ser Thr Gln Asp Arg Ile Leu Glu Met Lys Val Met Glu Phe
145                 150                 155                 160

Phe Met Lys Val Tyr Gly Tyr Arg Gly Lys His Leu Gly Gly Ser Arg
                165                 170                 175

Lys Pro Asp Gly Ala Ile Tyr Thr Val Gly Ser Pro Ile Asp Tyr Gly
            180                 185                 190

Val Ile Val Asp Thr Lys Ala Tyr Ser Gly Gly Tyr Asn Leu Pro Ile
        195                 200                 205

Gly Gln Ala Asp Glu Met Gln Arg Tyr Val Glu Glu Asn Gln Thr Arg
    210                 215                 220

Asn Lys His Ile Asn Pro Asn Glu Trp Trp Lys Val Tyr Pro Ser Ser
225                 230                 235                 240

Val Thr Glu Phe Lys Phe Leu Phe Val Ser Gly His Phe Lys Gly Asn
                245                 250                 255

Tyr Lys Ala Gln Leu Thr Arg Leu Asn His Ile Thr Asn Cys Asn Gly
            260                 265                 270

Ala Val Leu Ser Val Glu Glu Leu Leu Ile Gly Gly Glu Met Ile Lys
        275                 280                 285

Ala Gly Thr Leu Thr Leu Glu Glu Val Arg Arg Lys Phe Asn Asn Gly
    290                 295                 300

Glu Ile Asn Phe Gly Ser
305                 310

<210> SEQ ID NO 84
<211> LENGTH: 1830
<212> TYPE: DNA
<213> ORGANISM: Artificial sequence
<220> FEATURE:
<223> OTHER INFORMATION: P36-ZFN2-T2A-P36-ZFN1 polynucleotide sequence

<400> SEQUENCE: 84
atggtgccaa aaagaagag aaaggtagaa gaccctctc gagctgaaaa accttacaag      60
tgtcctgaat gtggaaagtc ttttctcgt tctgataatt tggttcgtca ccagcgaaca     120
cacacaggtg agaagccata taatgccca gaatgtggta atcattcag tcaggctgga     180 catttggctt ctcaccaacg acccacacc ggggagaagc catttaaatg ccctgagtgc    240
gggaagagtt tttcaacttc tggacatctt gttcgtcatc aacgtactca tactggagga   300
ctagtcaaaa gtgaactgga ggagaagaaa tctgaacttc gtcataaatt gaaatatgtg    360
```

```
cctcatgaat atattgaatt aattgaaatt gccagaaatt ccactcagga tagaattctt    420
gaaatgaagg taatggaatt ttttatgaaa gtttatggat atagaggtaa acatttgggt    480
ggatcaagga aaccggacgg agcaatttat actgtcggat ctcctattga ttacggtgtg    540
atcgtggata ctaaagctta tagcggaggt tataatctgc caattggcca agcagatgaa    600
atgcaacgat atgtcgaaga aaatcaaaca cgaaacaaac atatcaaccc taatgaatgg    660
tggaaagtct atccatcttc tgtaacggaa tttaagtttt tatttgtgag tggtcacttt    720
aaaggaaact acaaagctca gcttacacga ttaaatcata tcactaattg taatggagct    780
gttcttagtg tagaagagct tttaattggt ggagaaatga ttaaagccgg cacattaacc    840
ttagaggaag tgagacggaa atttaataac ggcgagataa actttggatc cgaaggaaga    900
ggatctcttc ttacttgtgg tgatgttgaa gagaatcctg gaccaaaaaa gaagagaaag    960
gtagaagacc cctctcgagc tgaaaaacct tataagtgtc ctgaatgtgg aaagtctttt   1020
tctacttctg gacatcttgt tcgtcaccag cgaacacaca caggtgagaa gccatataaa   1080
tgcccagaat gtggtaaatc attcagtact tctggacatc ttgttcgtca ccaacggacc   1140
cacaccgggg agaagccatt taatgccct gagtgcggga agagtttttc aacttctgga   1200
aatttggttc gtcatcaacg tactcatact ggaggactag tcaaaagtga actggaggag   1260
aagaaatctg aacttcgtca taaattgaaa tatgtgcctc atgaatatat tgaattaatt   1320
gaaattgcca gaaattccac tcaggataga attcttgaaa tgaaggtaat ggaattttt   1380 atgaaagttt atggatatag aggtaaacat ttgggtggat caaggaaacc ggacggagca   1440
atttatactg tcggatctcc tattgattac ggtgtgatcg tggatactaa agcttatagc   1500
ggaggttata atctgccaat tggccaagca gatgaaatgc aacgatatgt cgaagaaaat   1560
caaacacgaa acaaacatat caacactaat gaatggtgga agtctatcc atcttctgta   1620 acggaattta gttttttatt tgtgagtggt cactttaaag gaaactacaa agctcagctt   1680
acacgattaa atcatatcac taattgtaat ggagctgttc ttagtgtaga agagcttta   1740 attggtggag aaatgattaa agccggcaca ttaaccttag aggaagtgag acggaaattt   1800
aataacggcg agataaactt tggatcttaa                                    1830
```

<210> SEQ ID NO 85
<211> LENGTH: 609
<212> TYPE: PRT
<213> ORGANISM: Artificial sequence
<220> FEATURE:
<223> OTHER INFORMATION: P36-ZFN2-T2A-P36-ZFN1 polypeptide sequence

<400> SEQUENCE: 85

```
Met Val Pro Lys Lys Arg Lys Val Glu Asp Pro Ser Arg Ala Glu
1               5                   10                  15

Lys Pro Tyr Lys Cys Pro Glu Cys Gly Lys Ser Phe Ser Arg Ser Asp
                20                  25                  30

Asn Leu Val Arg His Gln Arg Thr His Thr Gly Glu Lys Pro Tyr Lys
            35                  40                  45

Cys Pro Glu Cys Gly Lys Ser Phe Ser Gln Ala Gly His Leu Ala Ser
        50                  55                  60

His Gln Arg Thr His Thr Gly Glu Lys Pro Phe Lys Cys Pro Glu Cys
65                  70                  75                  80

Gly Lys Ser Phe Ser Thr Ser Gly His Leu Val Arg His Gln Arg Thr
                85                  90                  95
```

-continued

```
His Thr Gly Gly Leu Val Lys Ser Glu Leu Glu Lys Lys Ser Glu
            100                 105                 110

Leu Arg His Lys Leu Lys Tyr Val Pro His Glu Tyr Ile Glu Leu Ile
        115                 120                 125

Glu Ile Ala Arg Asn Ser Thr Gln Asp Arg Ile Leu Glu Met Lys Val
    130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser Glu Gly Arg Gly Ser Leu Leu
    290                 295                 300

Thr Cys Gly Asp Val Glu Glu Asn Pro Gly Pro Lys Lys Arg Lys
305                 310                 315                 320

Val Glu Asp Pro Ser Arg Ala Glu Lys Pro Tyr Lys Cys Pro Glu Cys
                325                 330                 335

Gly Lys Ser Phe Ser Thr Ser Gly His Leu Val Arg His Gln Arg Thr
            340                 345                 350

His Thr Gly Glu Lys Pro Tyr Lys Cys Pro Glu Cys Gly Lys Ser Phe
        355                 360                 365

Ser Thr Ser Gly His Leu Val Arg His Gln Arg Thr His Thr Gly Glu
    370                 375                 380

Lys Pro Phe Lys Cys Pro Glu Cys Gly Lys Ser Phe Ser Thr Ser Gly
385                 390                 395                 400

Asn Leu Val Arg His Gln Arg Thr His Thr Gly Gly Leu Val Lys Ser
                405                 410                 415

Glu Leu Glu Glu Lys Lys Ser Glu Leu Arg His Lys Leu Lys Tyr Val
            420                 425                 430

Pro His Glu Tyr Ile Glu Leu Ile Glu Ile Ala Arg Asn Ser Thr Gln
        435                 440                 445

Asp Arg Ile Leu Glu Met Lys Val Met Glu Phe Phe Met Lys Val Tyr
    450                 455                 460

Gly Tyr Arg Gly Lys His Leu Gly Gly Ser Arg Lys Pro Asp Gly Ala
465                 470                 475                 480

Ile Tyr Thr Val Gly Ser Pro Ile Asp Tyr Gly Val Ile Val Asp Thr
                485                 490                 495

Lys Ala Tyr Ser Gly Gly Tyr Asn Leu Pro Ile Gly Gln Ala Asp Glu
            500                 505                 510

Met Gln Arg Tyr Val Glu Glu Asn Gln Thr Arg Asn Lys His Ile Asn
```

|     |     |     |     | 515 |     |     |     | 520 |     |     |     | 525 |     |
| --- | --- | --- | --- | --- | --- | --- | --- | --- | --- | --- | --- | --- | --- |
| Thr | Asn | Glu | Trp | Trp | Lys | Val | Tyr | Pro | Ser | Ser | Val | Thr | Glu | Phe | Lys |
|     | 530 |     |     |     |     | 535 |     |     |     |     | 540 |     |     |
| Phe | Leu | Phe | Val | Ser | Gly | His | Phe | Lys | Gly | Asn | Tyr | Lys | Ala | Gln | Leu |
| 545 |     |     |     |     | 550 |     |     |     |     | 555 |     |     |     |     | 560 |
| Thr | Arg | Leu | Asn | His | Ile | Thr | Asn | Cys | Asn | Gly | Ala | Val | Leu | Ser | Val |
|     |     |     |     |     | 565 |     |     |     |     | 570 |     |     |     |     | 575 |
| Glu | Glu | Leu | Leu | Ile | Gly | Gly | Glu | Met | Ile | Lys | Ala | Gly | Thr | Leu | Thr |
|     |     |     | 580 |     |     |     |     | 585 |     |     |     |     | 590 |
| Leu | Glu | Glu | Val | Arg | Arg | Lys | Phe | Asn | Asn | Gly | Glu | Ile | Asn | Phe | Gly |
|     |     | 595 |     |     |     |     | 600 |     |     |     |     | 605 |
| Ser |

<210> SEQ ID NO 86
<211> LENGTH: 1830
<212> TYPE: DNA
<213> ORGANISM: Artificial sequence
<220> FEATURE:
<223> OTHER INFORMATION: PDS-ZFN1-T2A-PDS-ZFN2 polynucleotide sequence

<400> SEQUENCE: 86

| atggtgccaa aaagaagag aaaggtagaa gacccctctc gagctgaaaa accttacaag | 60 |
| tgtcctgaat gtggaaagtc tttttctcag tctggagatt tgcgtcgtca ccagcgaaca | 120 |
| cacacaggtg agaagccata taaatgccca gaatgtggta atcattcag tacttctgga | 180 |
| aatttggttc gtcaccaacg gacccacacc ggggagaagc catttaaatg ccctgagtgc | 240 |
| gggaagagtt tttcacagcg cgcgcatctg gaacgccatc aacgtactca tactggagga | 300 |
| ctagtcaaaa gtgaactgga ggagaagaaa tctgaacttc gtcataaatt gaaatatgtg | 360 |
| cctcatgaat atattgaatt aattgaaatt gccagaaatt ccactcagga tagaattctt | 420 |
| gaaatgaagg taatggaatt ttttatgaaa gtttatggat atagaggtaa acatttgggt | 480 |
| ggatcaagga accggacgg agcaatttat actgtcggat ctcctattga ttacggtgtg | 540 |
| atcgtggata ctaaagctta tagcggaggt tataatctgc caattggcca agcagatgaa | 600 |
| atgcaacgat atgtcgaaga aaatcaaaca cgaaacaaac atatcaaccc taatgaatgg | 660 |
| tggaaagtct atccatcttc tgtaacggaa tttaagtttt tatttgtgag tggtcacttt | 720 |
| aaaggaaact acaaagctca gcttacacga ttaaatcata tcactaattg taatggagct | 780 |
| gttcttagtg tagaagagct tttaattggt ggagaaatga ttaaagccgg cacattaacc | 840 |
| ttagaggaag tgagacggaa atttaataac ggcgagataa actttggatc cgaaggaaga | 900 |
| ggatctcttc ttacttgtgg tgatgttgaa gagaatcctg accaaaaaaa gaagagaaag | 960 |
| gtagaagacc cctctcgagc tgaaaaacct tacaagtgtc ctgaatgtgg aaagtctttt | 1020 |
| tctcgcagcg atgaactggt gcgccaccag cgaacacaca caggtgagaa gccatataaa | 1080 |
| tgcccagaat gtgtaaaatc attcagtcag tctagcaacc tggttagaca ccaacggacc | 1140 |
| cacaccgggg agaagccatt taaatgccct gagtgcggga gagttttttc acataaaaac | 1200 |
| gcgctgcaga accatcaacg tactcatact ggaggactag tcaaaagtga actggaggag | 1260 |
| aagaaatctg aacttcgtca taaattgaaa tatgtgcctc atgaatatat tgaattaatt | 1320 |
| gaaattgcca gaaattccac tcaggataga attcttgaaa tgaaggtaat ggaatttttt | 1380 |
| atgaaagttt atggatatag aggtaaacat ttgggtggat caaggaaacc ggacggagca | 1440 |
| atttatactg tcggatctcc tattgattac ggtgtgatcg tggatactaa agcttatagc | 1500 |

```
ggaggttata atctgccaat tggccaagca gatgaaatgc aacgatatgt cgaagaaaat   1560
caaacacgaa acaaacatat caacactaat gaatggtgga aagtctatcc atcttctgta   1620
acggaattta agttttatt tgtgagtggt cactttaaag gaaactacaa agctcagctt   1680
acacgattaa atcatatcac taattgtaat ggagctgttc ttagtgtaga agagcttta   1740 attggtggag aaatgattaa agccggcaca ttaaccttag aggaagtgag acggaaattt   1800
aataacggcg agataaactt tggatcttaa                                    1830
```

<210> SEQ ID NO 87
<211> LENGTH: 609
<212> TYPE: PRT
<213> ORGANISM: Artificial sequence
<220> FEATURE:
<223> OTHER INFORMATION: PDS-ZFN1-T2A-PDS-ZFN2 polypeptide sequence

<400> SEQUENCE: 87

```
Met Val Pro Lys Lys Arg Lys Val Glu Asp Pro Ser Arg Ala Glu
1               5                   10                  15

Lys Pro Tyr Lys Cys Pro Glu Cys Gly Lys Ser Phe Ser Gln Ser Gly
            20                  25                  30

Asp Leu Arg Arg His Gln Arg Thr His Thr Gly Glu Lys Pro Tyr Lys
        35                  40                  45

Cys Pro Glu Cys Gly Lys Ser Phe Ser Thr Ser Gly Asn Leu Val Arg
    50                  55                  60

His Gln Arg Thr His Thr Gly Glu Lys Pro Phe Lys Cys Pro Glu Cys
65                  70                  75                  80

Gly Lys Ser Phe Ser Gln Arg Ala His Leu Glu Arg His Gln Arg Thr
                85                  90                  95

His Thr Gly Gly Leu Val Lys Ser Glu Leu Glu Glu Lys Lys Ser Glu
            100                 105                 110

Leu Arg His Lys Leu Lys Tyr Val Pro His Glu Tyr Ile Glu Leu Ile
        115                 120                 125

Glu Ile Ala Arg Asn Ser Thr Gln Asp Arg Ile Leu Glu Met Lys Val
    130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser Glu Gly Arg Gly Ser Leu Leu
    290                 295                 300
```

Thr Cys Gly Asp Val Glu Glu Asn Pro Gly Pro Lys Lys Lys Arg Lys
305                 310                 315                 320

Val Glu Asp Pro Ser Arg Ala Glu Lys Pro Tyr Lys Cys Pro Glu Cys
            325                 330                 335

Gly Lys Ser Phe Ser Arg Ser Asp Glu Leu Val Arg His Gln Arg Thr
            340                 345                 350

His Thr Gly Glu Lys Pro Tyr Lys Cys Pro Glu Cys Gly Lys Ser Phe
        355                 360                 365

Ser Gln Ser Ser Asn Leu Val Arg His Gln Arg Thr His Thr Gly Glu
    370                 375                 380

Lys Pro Phe Lys Cys Pro Glu Cys Gly Lys Ser Phe Ser His Lys Asn
385                 390                 395                 400

Ala Leu Gln Asn His Gln Arg Thr His Thr Gly Gly Leu Val Lys Ser
            405                 410                 415

Glu Leu Glu Glu Lys Lys Ser Glu Leu Arg His Lys Leu Lys Tyr Val
            420                 425                 430

Pro His Glu Tyr Ile Glu Leu Ile Glu Ile Ala Arg Asn Ser Thr Gln
        435                 440                 445

Asp Arg Ile Leu Glu Met Lys Val Met Glu Phe Phe Met Lys Val Tyr
450                 455                 460

Gly Tyr Arg Gly Lys His Leu Gly Gly Ser Arg Lys Pro Asp Gly Ala
465                 470                 475                 480

Ile Tyr Thr Val Gly Ser Pro Ile Asp Tyr Gly Val Ile Val Asp Thr
            485                 490                 495

Lys Ala Tyr Ser Gly Gly Tyr Asn Leu Pro Ile Gly Gln Ala Asp Glu
        500                 505                 510

Met Gln Arg Tyr Val Glu Glu Asn Gln Thr Arg Asn Lys His Ile Asn
    515                 520                 525

Thr Asn Glu Trp Trp Lys Val Tyr Pro Ser Ser Val Thr Glu Phe Lys
530                 535                 540

Phe Leu Phe Val Ser Gly His Phe Lys Gly Asn Tyr Lys Ala Gln Leu
545                 550                 555                 560

Thr Arg Leu Asn His Ile Thr Asn Cys Asn Gly Ala Val Leu Ser Val
            565                 570                 575

Glu Glu Leu Leu Ile Gly Gly Glu Met Ile Lys Ala Gly Thr Leu Thr
            580                 585                 590

Leu Glu Glu Val Arg Arg Lys Phe Asn Asn Gly Glu Ile Asn Phe Gly
        595                 600                 605

Ser

<210> SEQ ID NO 88
<211> LENGTH: 1830
<212> TYPE: DNA
<213> ORGANISM: Artificial sequence
<220> FEATURE:
<223> OTHER INFORMATION: FHT-ZFN1-T2A-FHT-ZFN2 polynucleotide sequence

<400> SEQUENCE: 88
atggtgccaa aaagaagag aaaggtagaa gacccctctc gagctgaaaa accttacaag      60
tgtcctgaat gtggaaagtc tttttctact tctggagaat tggttcgtca ccagcgaaca    120
cacacaggtg agaagccata taatgccca gaatgtggta atcattcag tacttctgga     180 catcttgttc gtcaccaacg gacccacacc ggggagaagc catttaaatg ccctgagtgc    240
gggaagagtt ttcacagag cagcaacctg gtgcgccatc aacgtactca tactggagga    300

```
ctagtcaaaa gtgaactgga ggagaagaaa tctgaacttc gtcataaatt gaaatatgtg    360
cctcatgaat atattgaatt aattgaaatt gccagaaatt ccactcagga tagaattctt    420
gaaatgaagg taatggaatt ttttatgaaa gtttatggat atagaggtaa acatttgggt    480
ggatcaagga aaccgacgg agcaatttat actgtcggat ctcctattga ttacggtgtg     540
atcgtggata ctaaagctta tagcggaggt tataatctgc caattggcca agcagatgaa    600
atgcaacgat atgtcgaaga aaatcaaaca cgaaacaaac atatcaaccc taatgaatgg    660
tggaaagtct atccatcttc tgtaacggaa tttaagtttt tatttgtgag tggtcacttt    720
aaaggaaact acaaagctca gcttacacga ttaaatcata tcactaattg taatggagct    780
gttcttagtg tagaagagct tttaattggt ggagaaatga ttaaagccgg cacattaacc    840
ttagaggaag tgagacggaa atttaataac ggcgagataa actttggatc cgaaggaaga    900
ggatctcttc ttacttgtgg tgatgttgaa gagaatcctg accaaaaaa gaagagaaag    960
gtagaagacc cctctcgagc tgaaaaacct tacaagtgtc ctgaatgtgg aaagtctttt    1020
tctcgcgcgg ataacctgac cgaacaccag cgaacacaca caggtgagaa gccatataaa    1080
tgcccagaat gtggtaaatc attcagtcag tctagcaacc tggttagaca ccaacggacc    1140
cacaccgggg agaagccatt taatgccct gagtgcggga gagttttttc aacttctgga     1200
gaattggttc gtcatcaacg tactcatact ggaggactag tcaaaagtga actggaggag    1260
aagaaatctg aacttcgtca taaattgaaa tatgtgcctc atgaatatat tgaattaatt    1320
gaaattgcca gaaattccac tcaggataga attcttgaaa tgaaggtaat ggattttttt    1380
atgaaagttt atggatatag aggtaaacat ttgggtggat caaggaaacc ggacggagca    1440
atttatactg tcggatctcc tattgattac ggtgtgatcg tggatactaa agcttatagc    1500
ggaggttata atctgccaat tggccaagca gatgaaatgc aacgatatgt cgaagaaaat    1560
caaacacgaa acaaacatat caacactaat gaatggtgga agtctatcc atcttctgta    1620
acggaattta gtttttatt tgtgagtggt cactttaaag gaaactacaa agctcagctt    1680
acacgattaa atcatatcac taattgtaat ggagctgttc ttagtgtaga agagctttta    1740
attggtggag aaatgattaa agccggcaca ttaaccttag aggaagtgag acggaaattt    1800
aataacggcg agataaactt tggatcttaa                                      1830
```

<210> SEQ ID NO 89
<211> LENGTH: 609
<212> TYPE: PRT
<213> ORGANISM: Artificial sequence
<220> FEATURE:
<223> OTHER INFORMATION: FHT-ZFN1-T2A-FHT-ZFN2 ploypeptide sequence

<400> SEQUENCE: 89

```
Met Val Pro Lys Lys Arg Lys Val Glu Asp Pro Ser Arg Ala Glu
1               5                   10                  15

Lys Pro Tyr Lys Cys Pro Glu Cys Gly Lys Ser Phe Ser Thr Ser Gly
            20                  25                  30

Glu Leu Val Arg His Gln Arg Thr His Thr Gly Glu Lys Pro Tyr Lys
        35                  40                  45

Cys Pro Glu Cys Gly Lys Ser Phe Ser Thr Ser Gly His Leu Val Arg
    50                  55                  60

His Gln Arg Thr His Thr Gly Glu Lys Pro Phe Lys Cys Pro Glu Cys
65                  70                  75                  80

Gly Lys Ser Phe Ser Gln Ser Ser Asn Leu Val Arg His Gln Arg Thr
                85                  90                  95
```

```
His Thr Gly Gly Leu Val Lys Ser Glu Leu Glu Glu Lys Lys Ser Glu
                100                 105                 110

Leu Arg His Lys Leu Lys Tyr Val Pro His Glu Tyr Ile Glu Leu Ile
            115                 120                 125

Glu Ile Ala Arg Asn Ser Thr Gln Asp Arg Ile Leu Glu Met Lys Val
        130                 135                 140

Met Glu Phe Phe Met Lys Val Tyr Gly Tyr Arg Gly Lys His Leu Gly
145                 150                 155                 160

Gly Ser Arg Lys Pro Asp Gly Ala Ile Tyr Thr Val Gly Ser Pro Ile
                165                 170                 175

Asp Tyr Gly Val Ile Val Asp Thr Lys Ala Tyr Ser Gly Gly Tyr Asn
            180                 185                 190

Leu Pro Ile Gly Gln Ala Asp Glu Met Gln Arg Tyr Val Glu Glu Asn
        195                 200                 205

Gln Thr Arg Asn Lys His Ile Asn Pro Asn Glu Trp Trp Lys Val Tyr
    210                 215                 220

Pro Ser Ser Val Thr Glu Phe Lys Phe Leu Phe Val Ser Gly His Phe
225                 230                 235                 240

Lys Gly Asn Tyr Lys Ala Gln Leu Thr Arg Leu Asn His Ile Thr Asn
                245                 250                 255

Cys Asn Gly Ala Val Leu Ser Val Glu Glu Leu Leu Ile Gly Gly Glu
            260                 265                 270

Met Ile Lys Ala Gly Thr Leu Thr Leu Glu Glu Val Arg Arg Lys Phe
        275                 280                 285

Asn Asn Gly Glu Ile Asn Phe Gly Ser Glu Gly Arg Gly Ser Leu Leu
    290                 295                 300

Thr Cys Gly Asp Val Glu Glu Asn Pro Gly Pro Lys Lys Lys Arg Lys
305                 310                 315                 320

Val Glu Asp Pro Ser Arg Ala Glu Lys Pro Tyr Lys Cys Pro Glu Cys
                325                 330                 335

Gly Lys Ser Phe Ser Arg Ala Asp Asn Leu Thr Glu His Gln Arg Thr
            340                 345                 350

His Thr Gly Glu Lys Pro Tyr Lys Cys Pro Glu Cys Gly Lys Ser Phe
        355                 360                 365

Ser Gln Ser Ser Asn Leu Val Arg His Gln Arg Thr His Thr Gly Glu
    370                 375                 380

Lys Pro Phe Lys Cys Pro Glu Cys Gly Lys Ser Phe Ser Thr Ser Gly
385                 390                 395                 400

Glu Leu Val Arg His Gln Arg Thr His Thr Gly Gly Leu Val Lys Ser
                405                 410                 415

Glu Leu Glu Glu Lys Lys Ser Glu Leu Arg His Lys Leu Lys Tyr Val
            420                 425                 430

Pro His Glu Tyr Ile Glu Leu Ile Glu Ile Ala Arg Asn Ser Thr Gln
        435                 440                 445

Asp Arg Ile Leu Glu Met Lys Val Met Glu Phe Phe Met Lys Val Tyr
    450                 455                 460

Gly Tyr Arg Gly Lys His Leu Gly Gly Ser Arg Lys Pro Asp Gly Ala
465                 470                 475                 480

Ile Tyr Thr Val Gly Ser Pro Ile Asp Tyr Gly Val Ile Val Asp Thr
                485                 490                 495

Lys Ala Tyr Ser Gly Gly Tyr Asn Leu Pro Ile Gly Gln Ala Asp Glu
            500                 505                 510
```

```
Met Gln Arg Tyr Val Glu Glu Asn Gln Thr Arg Asn Lys His Ile Asn
            515                 520                 525
Thr Asn Glu Trp Trp Lys Val Tyr Pro Ser Ser Val Thr Glu Phe Lys
        530                 535                 540
Phe Leu Phe Val Ser Gly His Phe Lys Gly Asn Tyr Lys Ala Gln Leu
545                 550                 555                 560
Thr Arg Leu Asn His Ile Thr Asn Cys Asn Gly Ala Val Leu Ser Val
                565                 570                 575
Glu Glu Leu Leu Ile Gly Gly Glu Met Ile Lys Ala Gly Thr Leu Thr
            580                 585                 590
Leu Glu Glu Val Arg Arg Lys Phe Asn Asn Gly Glu Ile Asn Phe Gly
        595                 600                 605
Ser

<210> SEQ ID NO 90
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 90
ctatccttcg caagacccttt cc                                              22

<210> SEQ ID NO 91
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 91
gtctgccagt tcagttcgtt gttc                                             24

<210> SEQ ID NO 92
<211> LENGTH: 30
<212> TYPE: DNA
<213> ORGANISM: Artificial sequence
<220> FEATURE:
<223> OTHER INFORMATION: uidA gene derived QEQ-ZFN target sequence

<400> SEQUENCE: 92
atgttcttcc cctcctgagg ggaagaatta                                       30

<210> SEQ ID NO 93
<211> LENGTH: 10
<212> TYPE: PRT
<213> ORGANISM: Artificial sequence
<220> FEATURE:
<223> OTHER INFORMATION: uidA gene derived QEQ-ZFN target deduced amino
      acid sequence
<220> FEATURE:
<221> NAME/KEY: misc_feature
<222> LOCATION: (6)..(6)
<223> OTHER INFORMATION: Stop codon "translated" sequence

<400> SEQUENCE: 93

Met Phe Phe Pro Ser Xaa Gly Glu Glu Leu
1               5                   10

<210> SEQ ID NO 94
<211> LENGTH: 27
<212> TYPE: DNA
<213> ORGANISM: Artificial sequence
```

```
<220> FEATURE:
<223> OTHER INFORMATION: uidA gene derived QEQ-ZFN target sequence after
      misrepairing the double strand break

<400> SEQUENCE: 94
atgttcttcc cctccgggga agaatta                                              27

<210> SEQ ID NO 95
<211> LENGTH: 9
<212> TYPE: PRT
<213> ORGANISM: Artificial sequence
<220> FEATURE:
<223> OTHER INFORMATION: Misrepaired uidA gene derived QEQ-ZFN target
      deduced amino acid sequence

<400> SEQUENCE: 95

Met Phe Phe Pro Ser Gly Glu Glu Leu
1               5

<210> SEQ ID NO 96
<211> LENGTH: 77
<212> TYPE: DNA
<213> ORGANISM: Artificial sequence
<220> FEATURE:
<223> OTHER INFORMATION: NT-GUS-stop

<400> SEQUENCE: 96
ctgcagtcga cggtaccatg ttcttcccct cctgagggga agaattacgt cctgtagaaa          60
ccccaacccg tgaaatc                                                        77

<210> SEQ ID NO 97
<211> LENGTH: 78
<212> TYPE: DNA
<213> ORGANISM: Artificial sequence
<220> FEATURE:
<223> OTHER INFORMATION: N-t7

<400> SEQUENCE: 97
ctgcagtcga cggtaccatg ttcttcccct cctggagggg aagaattacg tcctgtagaa          60
accccaaccc gtgaaatc                                                       78

<210> SEQ ID NO 98
<211> LENGTH: 78
<212> TYPE: DNA
<213> ORGANISM: Artificial sequence
<220> FEATURE:
<223> OTHER INFORMATION: Pet47

<400> SEQUENCE: 98
ctgcagtcga cggtaccatg ttcttcccct cctgaagggg aagaattacg tcctgtagaa          60
accccaaccc gtgaaatc                                                       78

<210> SEQ ID NO 99
<211> LENGTH: 79
<212> TYPE: DNA
<213> ORGANISM: Artificial sequence
<220> FEATURE:
<223> OTHER INFORMATION: Pet41

<400> SEQUENCE: 99
ctgcagtcga cggtaccatg ttcttcccct cctgtgaggg gaagaattac gtcctgtaga          60
aaccccaacc cgtgaaatc                                                      79
```

```
<210> SEQ ID NO 100
<211> LENGTH: 77
<212> TYPE: DNA
<213> ORGANISM: Artificial sequence
<220> FEATURE:
<223> OTHER INFORMATION: Pet30

<400> SEQUENCE: 100
ctgcagtcga cggtaccatg ttcttcccca cccgagggga agaattacgt cctgtagaaa      60
ccccaacccg tgaaatc                                                    77

<210> SEQ ID NO 101
<211> LENGTH: 77
<212> TYPE: DNA
<213> ORGANISM: Artificial sequence
<220> FEATURE:
<223> OTHER INFORMATION: Pet29

<400> SEQUENCE: 101
ctgcagtcga cggtaccatg ttcttcccct cttgagggga agaattacgt cctgtagaaa      60
ccccaacccg tgaaatc                                                    77

<210> SEQ ID NO 102
<211> LENGTH: 75
<212> TYPE: DNA
<213> ORGANISM: Artificial sequence
<220> FEATURE:
<223> OTHER INFORMATION: N-t115

<400> SEQUENCE: 102
ctgcagtcga cggtaccatg ttcttcccct cgaggggaag aattacgtcc tgtagaaacc      60
ccaacccgtg aaatc                                                      75

<210> SEQ ID NO 103
<211> LENGTH: 75
<212> TYPE: DNA
<213> ORGANISM: Artificial sequence
<220> FEATURE:
<223> OTHER INFORMATION: N-t11

<400> SEQUENCE: 103
ctgcagtcga cggtaccatg ttcttcccct tgaggggaag aattacgtcc tgtagaaacc      60
ccaacccgtg aaatc                                                      75

<210> SEQ ID NO 104
<211> LENGTH: 73
<212> TYPE: DNA
<213> ORGANISM: Artificial sequence
<220> FEATURE:
<223> OTHER INFORMATION: N-t6

<400> SEQUENCE: 104
ctgcagtcga cggtaccatg ttcttcccct aggggaagaa ttacgtcctg tagaaacccc      60
aacccgtgaa atc                                                        73

<210> SEQ ID NO 105
<211> LENGTH: 74
<212> TYPE: DNA
<213> ORGANISM: Artificial sequence
<220> FEATURE:
<223> OTHER INFORMATION: Pet62

<400> SEQUENCE: 105
```

```
ctgcagtcga cggtaccatg ttcttcccct gagggaaga attacgtcct gtagaaaccc      60
caacccgtga aatc                                                      74

<210> SEQ ID NO 106
<211> LENGTH: 72
<212> TYPE: DNA
<213> ORGANISM: Artificial sequence
<220> FEATURE:
<223> OTHER INFORMATION: N-t4

<400> SEQUENCE: 106
ctgcagtcga cggtaccatg ttcttcccct cgggaagaat tacgtcctgt agaaacccca      60
acccgtgaaa tc                                                         72

<210> SEQ ID NO 107
<211> LENGTH: 72
<212> TYPE: DNA
<213> ORGANISM: Artificial sequence
<220> FEATURE:
<223> OTHER INFORMATION: N-t114

<400> SEQUENCE: 107
ctgcagtcga cggtaccatg ttcttcccct ggggaagaat tacgtcctgt agaaacccca      60
acccgtgaaa tc                                                         72

<210> SEQ ID NO 108
<211> LENGTH: 72
<212> TYPE: DNA
<213> ORGANISM: Artificial sequence
<220> FEATURE:
<223> OTHER INFORMATION: N-t101

<400> SEQUENCE: 108
ctgcagtcga cggtaccatg ttcttcccca ggggaagaat tacgtcctgt agaaacccca      60
acccgtgaaa tc                                                         72

<210> SEQ ID NO 109
<211> LENGTH: 68
<212> TYPE: DNA
<213> ORGANISM: Artificial sequence
<220> FEATURE:
<223> OTHER INFORMATION: Pet26

<400> SEQUENCE: 109
ctgcagtcga cggtaccatg ttcttccggg aagaattacg tcctgtagaa accccaaccc      60
gtgaaatc                                                              68

<210> SEQ ID NO 110
<211> LENGTH: 60
<212> TYPE: DNA
<213> ORGANISM: Artificial sequence
<220> FEATURE:
<223> OTHER INFORMATION: Pet49

<400> SEQUENCE: 110
ctgcagtcga cggtaccatg ttcttcccct cgtcctgtag aaaccccaac ccgtgaaatc      60

<210> SEQ ID NO 111
<211> LENGTH: 58
<212> TYPE: DNA
<213> ORGANISM: Artificial sequence
<220> FEATURE:
<223> OTHER INFORMATION: Pet48
```

<400> SEQUENCE: 111
ctgcagtcga cggtaagggg aagaattacg tcctgtagaa accccaaccc gtgaaatc    58

<210> SEQ ID NO 112
<211> LENGTH: 54
<212> TYPE: DNA
<213> ORGANISM: Artificial sequence
<220> FEATURE:
<223> OTHER INFORMATION: N-t104

<400> SEQUENCE: 112
ctgcagtcga cggtaccatg tttacgtcct gtagaaaccc caacccgtga aatc    54

<210> SEQ ID NO 113
<211> LENGTH: 51
<212> TYPE: DNA
<213> ORGANISM: Artificial sequence
<220> FEATURE:
<223> OTHER INFORMATION: Pet51

<400> SEQUENCE: 113
ctgcagtcga cggtagaatt acgtcctgta gaaaccccaa cccgtgaaat c    51

<210> SEQ ID NO 114
<211> LENGTH: 49
<212> TYPE: DNA
<213> ORGANISM: Artificial sequence
<220> FEATURE:
<223> OTHER INFORMATION: N-t111

<400> SEQUENCE: 114
ctgcagtcga cggtaccatg ttcctgtaga aaccccaacc cgtgaaatc    49

<210> SEQ ID NO 115
<211> LENGTH: 42
<212> TYPE: DNA
<213> ORGANISM: Artificial sequence
<220> FEATURE:
<223> OTHER INFORMATION: Pet34

<400> SEQUENCE: 115
ctgcagtcga cggtaccatg ttcttcccca acccgtgaaa tc    42

<210> SEQ ID NO 116
<211> LENGTH: 28
<212> TYPE: DNA
<213> ORGANISM: Artificial sequence
<220> FEATURE:
<223> OTHER INFORMATION: Pet25

<400> SEQUENCE: 116
ctgcagtcga cccccaaccc gtgaaatc    28

<210> SEQ ID NO 117
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 117
tattgagtca aaaggtggcc aagtc    25

<210> SEQ ID NO 118

-continued

```
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 118
gcagatgatc atatgtgttc ttcag                                          25

<210> SEQ ID NO 119
<211> LENGTH: 155
<212> TYPE: DNA
<213> ORGANISM: Petunia x hybrida
<220> FEATURE:
<221> NAME/KEY: misc_feature
<223> OTHER INFORMATION: Native PDS sequence

<400> SEQUENCE: 119
tattgagtca aaaggtggcc aagtcagact aaactcacga ataagaaaga tcgagctgaa    60
cgaggatgga agtgtcaagt gttttatact gaataatggc acttcaattg agggagatgc   120
attcgtgttt gctgctccag gtataatatc catta                              155

<210> SEQ ID NO 120
<211> LENGTH: 155
<212> TYPE: DNA
<213> ORGANISM: Petunia x hybrida
<220> FEATURE:
<221> NAME/KEY: misc_feature
<223> OTHER INFORMATION: Native PDS sequence

<400> SEQUENCE: 120
tattgagtca aaaggtggcc aagtcagact aaactcacga ataagaaaga tcgagctgaa    60
cgaggatgga agtgtcaagt gttttatact gaataatggc acttcaattg agggagatgc   120
attcgtgttt gctgctccag gtataatatc catta                              155

<210> SEQ ID NO 121
<211> LENGTH: 155
<212> TYPE: DNA
<213> ORGANISM: Petunia x hybrida
<220> FEATURE:
<221> NAME/KEY: misc_feature
<223> OTHER INFORMATION: Native PDS sequence

<400> SEQUENCE: 121
tattgagtca aaaggtggcc aagtcagact aaactcacga ataagaaaga tcgagctgaa    60
cgaggatgga agtgtcaagt gttttatact gaataatggc acttcaattg agggagatgc   120
attcgtgttt gctgctccag gtataatatc catta                              155

<210> SEQ ID NO 122
<211> LENGTH: 155
<212> TYPE: DNA
<213> ORGANISM: Artificial sequence
<220> FEATURE:
<223> OTHER INFORMATION: YPDS6 - PDS muatant

<400> SEQUENCE: 122
tattgagtca aaaggtggcc aagtcagact aaactcacga ataagaaaga tcgagctgaa    60
cgaggatgga agtgtcaagt gttttatact gaataatggc acttcgattg agggagatgc   120
attcgtgttt gctgctccag gtataatatc catta                              155

<210> SEQ ID NO 123
```

```
<211> LENGTH: 155
<212> TYPE: DNA
<213> ORGANISM: Artificial sequence
<220> FEATURE:
<223> OTHER INFORMATION: Y12 - PDS muatant

<400> SEQUENCE: 123
tattgagtca aaaggtggcc aagtcagact aaactcacga ataagaaaga tcgagctgaa      60
cgaggatgga agtgtcaagt gttttatact gaataatggc acttcagttg agggagatgc     120
attcgtgttt gctgctccag gtataatatc catta                                155

<210> SEQ ID NO 124
<211> LENGTH: 155
<212> TYPE: DNA
<213> ORGANISM: Artificial sequence
<220> FEATURE:
<223> OTHER INFORMATION: G38 - PDS muatant

<400> SEQUENCE: 124
tattgagtca aaaggtggcc aagtcagact aaactcacga ataagaaaga tcgagctgaa      60
cgaggatgga agtgtcaagt gttttatact gaataatggc acttcaactg agggagatgc    120
attcgtgttt gctgctccag gtataatatc catta                                155

<210> SEQ ID NO 125
<211> LENGTH: 155
<212> TYPE: DNA
<213> ORGANISM: Artificial sequence
<220> FEATURE:
<223> OTHER INFORMATION: G29 - PDS muatant

<400> SEQUENCE: 125
tattgagtca aaaggtggcc aagtcagact aaactcacga ataagaaaga tcgagctgaa      60
cgaggatgga agtgtcaagt gttttatact gaataatggc acttcaatta agggagatgc    120
attcgtgttt gctgctccag gtataatatc catta                                155

<210> SEQ ID NO 126
<211> LENGTH: 155
<212> TYPE: DNA
<213> ORGANISM: Artificial sequence
<220> FEATURE:
<223> OTHER INFORMATION: Y19 - PDS muatant

<400> SEQUENCE: 126
tattgagtca aaaggtggcc aagtcagact aaactcacga ataagaaaga tcgagctgaa      60
cgaggatgga agtgtcaagt gttttatact gaataatggc actccaatcg agggagatgc    120
attcgtgttt gctgctccag gtataatatc catta                                155

<210> SEQ ID NO 127
<211> LENGTH: 155
<212> TYPE: DNA
<213> ORGANISM: Artificial sequence
<220> FEATURE:
<223> OTHER INFORMATION: Y22 - PDS muatant

<400> SEQUENCE: 127
tattgagtca aaaggtggcc aagtcagact aaactcacga ataagaaaga tcgagctgaa      60
cgaggatgga agtgtcaagt gttttatact gaataatggc acttcaatcg agggagatgc    120
attcgtgttt gctgctccag gtataatatc catta                                155
```

<210> SEQ ID NO 128
<211> LENGTH: 155
<212> TYPE: DNA
<213> ORGANISM: Artificial sequence
<220> FEATURE:
<223> OTHER INFORMATION: YPDS11 - PDS muatant

<400> SEQUENCE: 128

```
tattgagtca aaaggtggcc aagtcagact aaactcacga ataagaaaga tcgagctgaa      60
cgaggatgga agtgtcaagt gttttatact gaataatggc actttaattg agggagatgc     120
attcgtgttt gctgctccag gtataatatc catta                                155
```

<210> SEQ ID NO 129
<211> LENGTH: 678
<212> TYPE: DNA
<213> ORGANISM: Artificial sequence
<220> FEATURE:
<223> OTHER INFORMATION: DsRed2 coding sequence (GB accession no.
      AY818373 nucleotides 1395-2074)

<400> SEQUENCE: 129

```
atggcctcct ccgagaacgt catcaccgag ttcatgcgct tcaaggtgcg catggagggc      60
accgtgaacg gccacgagtt cgagatcgag ggcgagggcg agggccgccc ctacgagggc     120
cacaacaccg tgaagctgaa ggtgaccaag ggcggccccc tgcccttcgc ctgggacatc     180
ctgtcccccc agttccagta cggctccaag gtgtacgtga agcaccccgc cgacatcccc     240
gactacaaga agctgtcctt ccccgagggc ttcaagtggg agcgcgtgat gaacttcgag     300
gacggcggcg tggcgaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccgcg acggcgtgct gaagggcgag     480
acccacaagg ccctgaagct gaaggacggc ggccactacc tggtggagtt caagtccatc     540
tacatggcca agaagcccgt gcagctgccc ggctactact acgtggacgc caagctggac     600
atcacctccc acaacgagga ctacaccatc gtggagcagt acgagcgcac cgagggccgc     660
caccacctgt tcctgtga                                                   678
```

<210> SEQ ID NO 130
<211> LENGTH: 720
<212> TYPE: DNA
<213> ORGANISM: Artificial sequence
<220> FEATURE:
<223> OTHER INFORMATION: EGFP coding sequence

<400> SEQUENCE: 130

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
```

```
tacctgagca cccagtccgc cctgagcaaa gacccaacg agaagcgcga tcacatggtc      660
ctgctggagt tcgtgaccgc cgccgggatc actctcggca tggacgagct gtacaagtga      720
```

<210> SEQ ID NO 131
<211> LENGTH: 217
<212> TYPE: DNA
<213> ORGANISM: Petunia x hybrida
<220> FEATURE:
<221> NAME/KEY: misc_feature
<223> OTHER INFORMATION: PDS exon

<400> SEQUENCE: 131

```
caggagaaac atggttcaaa aatggccttt ttagatggta atcctcctga gagactttgc      60
atgccgattg ttgaacatat tgagtcaaaa ggtggccaag tcagactaaa ctcacgaata     120
agaaagatcg agctgaacga ggatggaagt gtcaagtgtt ttatactgaa taatggcact     180
tcaattgagg gagatgcatt cgtgtttgct gctccag                              217
```

<210> SEQ ID NO 132
<211> LENGTH: 22
<212> TYPE: DNA
<213> ORGANISM: Artificial sequence
<220> FEATURE:
<223> OTHER INFORMATION: A complementary short fragment of the PDS exon
      of Petunia X Hibrida

<400> SEQUENCE: 132

```
gtgaagttaa ctccctctac gt                                               22
```

<210> SEQ ID NO 133
<211> LENGTH: 141
<212> TYPE: DNA
<213> ORGANISM: Petunia x hybrida
<220> FEATURE:
<221> NAME/KEY: misc_feature
<223> OTHER INFORMATION: FHT exon

<400> SEQUENCE: 133

```
cacactgatc caggaaccat cactctcttg ttacaagacc aagttggtgg gcttcaagct      60
actaaagata atggcaaaac ttggatcact gttcagcctg ttgaaggtgc ttttgttgtc     120
aatcttggtg accacggtca t                                               141
```

<210> SEQ ID NO 134
<211> LENGTH: 23
<212> TYPE: DNA
<213> ORGANISM: Artificial sequence
<220> FEATURE:
<223> OTHER INFORMATION: A complementary short fragment of the FHTexon
      of Petunia X Hibrida

<400> SEQUENCE: 134

```
gacaagtcgg acaacttcca cga                                              23
```

<210> SEQ ID NO 135
<211> LENGTH: 9
<212> TYPE: DNA
<213> ORGANISM: Artificial sequence
<220> FEATURE:
<223> OTHER INFORMATION: TS1 binding site for ZFNs in the PDS gene

<400> SEQUENCE: 135

```
ggagatgca                                                               9
```

<210> SEQ ID NO 136
<211> LENGTH: 9
<212> TYPE: DNA
<213> ORGANISM: Artificial sequence
<220> FEATURE:
<223> OTHER INFORMATION: TS2 binding site for ZFNs in the PDS gene

<400> SEQUENCE: 136 cacttcaat                                                                 9

<210> SEQ ID NO 137
<211> LENGTH: 6
<212> TYPE: DNA
<213> ORGANISM: Artificial sequence
<220> FEATURE:
<223> OTHER INFORMATION: MfeI site used for selection and isolation of
      ZFNs mediated PDS mutants

<400> SEQUENCE: 137 caattg                                                                    6

<210> SEQ ID NO 138
<211> LENGTH: 174
<212> TYPE: DNA
<213> ORGANISM: Pisum sativum
<220> FEATURE:
<221> NAME/KEY: misc_feature
<223> OTHER INFORMATION: RSSU sequence

<400> SEQUENCE: 138
atggcttcta tgatatcctc ttccgctgtg acaacagtca gccgtgcttc tagggtgcaa         60
tccgcggcag tggctccatt cggcggcctg aaatccatga ctggattccc agtgaagaag        120
gtcaacactg acattacttc cattacaagc aatggtggaa gagtaaagtg catg              174

<210> SEQ ID NO 139
<211> LENGTH: 156
<212> TYPE: DNA
<213> ORGANISM: Nicotiana sylvestris

<400> SEQUENCE: 139
cggcggcttc tcacctctct cctccgtcaa tcggctcaac gtggcggcgg tccaatttcc         60
cgatccttgg gaaactccat ccctaaatcc gctgcacgcg cctcttcacg cgcgtcccct        120
aagggattcc tcttaaaccg cgcgcccgta cagtac                                  156

<210> SEQ ID NO 140
<211> LENGTH: 9
<212> TYPE: DNA
<213> ORGANISM: Artificial sequence
<220> FEATURE:
<223> OTHER INFORMATION: PDS-ZFN1 target site sequence

<400> SEQUENCE: 140 ggagatgca                                                                 9

<210> SEQ ID NO 141
<211> LENGTH: 9
<212> TYPE: DNA
<213> ORGANISM: Artificial sequence
<220> FEATURE:
<223> OTHER INFORMATION: PDS-ZFN2 target site sequence

<400> SEQUENCE: 141 gtgaagtta                                                                 9

```
<210> SEQ ID NO 142
<211> LENGTH: 9
<212> TYPE: DNA
<213> ORGANISM: Artificial sequence
<220> FEATURE:
<223> OTHER INFORMATION: FHT-ZFN1 target site sequence

<400> SEQUENCE: 142 gaaggtgct                                                                 9

<210> SEQ ID NO 143
<211> LENGTH: 9
<212> TYPE: DNA
<213> ORGANISM: Artificial sequence
<220> FEATURE:
<223> OTHER INFORMATION: FHT-ZFN2 target site sequence

<400> SEQUENCE: 143 gacaagtcg                                                                 9

<210> SEQ ID NO 144
<211> LENGTH: 36
<212> TYPE: DNA
<213> ORGANISM: Artificial sequence
<220> FEATURE:
<223> OTHER INFORMATION: Zinc finger target sequence
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t
<220> FEATURE:
<221> NAME/KEY: misc_feature
<222> LOCATION: (29)..(36)
<223> OTHER INFORMATION: n is a, c, g, or t

<400> SEQUENCE: 144
nnnnnnggtg gaaagnnnng gggaagaann nnnnnn                                  36

<210> SEQ ID NO 145
<211> LENGTH: 39
<212> TYPE: DNA
<213> ORGANISM: Artificial sequence
<220> FEATURE:
<223> OTHER INFORMATION: Zinc finger target sequence with insertion
      mutations at the repair site
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (16)..(22)
<223> OTHER INFORMATION: n is a, c, g, or t
<220> FEATURE:
<221> NAME/KEY: misc_feature
<222> LOCATION: (32)..(39)
<223> OTHER INFORMATION: n is a, c, g, or t

<400> SEQUENCE: 145
nnnnnnggtg gaaagnnnnn nnggggaaga annnnnnnn                               39
```

What is claimed is:

1. A method of generating genotypic variation in a genome of a plant, the method comprising introducing into a gamete or a gamete producing tissue of the plant at least one Tobacco Rattle Virus (TRV) expression vector encoding at least one chimeric nuclease which comprises a meganuclease or a zinc finger binding domain, a nuclease and a localization signal to a DNA-containing organelle, wherein said meganuclease or said zinc finger binding domain mediates specific targeting of said nuclease to the genome of the plant, wherein said introducing is performed such that said gamete or gamete producing tissue expresses said chimeric nuclease but not all plant tissues express said chimeric nuclease, thereby generating genotypic variation in the genome of the plant.

2. A method of generating male sterility in a plant, the method comprising upregulating in the plant a structural or functional gene of a mitochondria or chloroplast associated with male sterility by introducing into a gamete or a gamete producing tissue of the plant at least one Tobacco Rattle Virus (TRV) expression vector encoding at least one chimeric nuclease which comprises a meganuclease or a zinc finger binding domain, a nuclease and a mitochondria or chloroplast localization signal and a nucleic acid expression construct which comprises at least one heterologous nucleic acid sequence which can upregulate said structural or functional gene of a mitochondria or chloroplast when targeted into the genome of said mitochondria or chloroplast, wherein said meganuclease or said zing finger binding domain mediates targeting of said heterologous nucleic acid sequence to the genome of the mitochondria or chloroplast, and wherein said introducing is performed such that said gamete or gamete producing tissue expresses said chimeric nuclease but not all plant tissues express said chimeric nuclease, thereby generating male sterility in the plant.

3. A method of generating a herbicide resistant plant, the method comprising introducing into a gamete or a gamete producing tissue of the plant at least one Tobacco Raffle Virus (TRV) expression vector encoding at least one chimeric nuclease which comprises a meganuclease or a zinc finger binding domain, a nuclease and a chloroplast localization signal, wherein said meganuclease or said zinc finger binding domain mediates targeting of said nuclease to a gene conferring sensitivity to herbicides, and wherein said introducing is performed such that said gamete or gamete producing tissue expresses said chimeric nuclease but not all plant tissues express said chimeric nuclease, thereby generating the herbicide resistant plant.

4. A method of generating a transgenic plant, the method comprising: introducing into one or more cells of a gamete or a gamete producing tissue of the plant at least one Tobacco Rattle Virus (TRV) expression vector encoding at least one chimeric nuclease which comprises a meganuclease or a zinc finger binding domain, a nuclease and a localization signal to a DNA-containing organelle, wherein said introducing is performed such that said gamete or gamete producing tissue expresses said chimeric nuclease but not all plant tissues express said chimeric nuclease.

5. The method of claim 1, wherein said introducing is performed directly into said gamete-producing tissue.

6. The method of claim 5, wherein said directly into said gamete-producing tissue is effected by flower infiltration or floral dip transformation.

7. The method of claim 5, wherein said directly into said gamete-producing tissue is effected without meristem infection.

8. The method of claim 1, wherein said plant comprises an adult plant.

9. The method of claim 1, wherein said plant comprises a *Petunia hybrida* or a *Nicotiana tabacum*.

10. The method of claim 1, wherein said plant in selected from the group consisting of an *Arabidopsis thaliana*, an *Artemisia* sp., a *Artemisia annua*, a *Beta vulgaris*, a *Solanum tuberosum*, a *Solanum pimpinellifolium*, a *Solanum lycopersicum*, a *Solanum melongena*, a *Spinacia oleracea*, a *Pisum sativum*, a *Capsicum annuum*, a *Cucumis sativus*, a *Nicotiana benthamiana*, a *Nicotiana tabacum*, a *Zea mays*, a *Brassica napus*, a *Gossypium hirsutum* cv. Siv'on, a *Oryza sativa* and a *Oryza glaberrima*.

11. The method of claim 1, wherein said TRV expression vector comprises a pTRV2 based expression vector.

12. The method of claim 1, wherein said zinc finger binding domain binds a 9 nucleotide sequence.

13. The method of claim 1, wherein said localization signal comprises a ribulose-1,5-bisphospate carboxylase small subunit (RSSU) sequence (SEQ ID NO: 138).

14. The method of claim 1, wherein said localization signal comprises an ATPase beta subunit (ATP-β) sequence (SEQ ID NO: 139).

* * * * *